US012611445B2

(12) United States Patent (10) Patent No.: US 12,611,445 B2
Piaggio et al. (45) Date of Patent: Apr. 28, 2026

(54) INTERLEUKIN-2 VARIANTS WITH MODIFIED BIOLOGICAL ACTIVITY

(71) Applicants: Institut Curie, Paris (FR); Institut National de la Sante et de la Recherche Medicale, Paris (FR); Institut Pasteur, Paris (FR); Centre National de la Recherche Scientifique, Paris (FR)

(72) Inventors: Eliane Piaggio, Paris (FR); Sebastian Amigorena, Paris (FR); Pamela Caudana, Paris (FR); Felix Rey, Gif sur Yvette (FR); Gleyder Roman-Sosa, Manhattan, KS (US); Pablo Guardado-Calvo, Paris (FR)

(73) Assignees: Institut Curie, Paris (FR); Institut National de la Sante et de la Recherche Medicale, Paris (FR); Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 1222 days.

(21) Appl. No.: 17/599,326

(22) PCT Filed: Mar. 27, 2020

(86) PCT No.: PCT/EP2020/058726
§ 371 (c)(1),
(2) Date: Sep. 28, 2021

(87) PCT Pub. No.: WO2020/201095
PCT Pub. Date: Oct. 8, 2020

(65) Prior Publication Data
US 2022/0193198 A1 Jun. 23, 2022

(30) Foreign Application Priority Data

Mar. 29, 2019 (EP) ..................................... 19305426
Oct. 28, 2019 (EP) ..................................... 19306402

(51) Int. Cl.
| | |
|---|---|
| A61K 38/20 | (2006.01) |
| A61K 47/68 | (2017.01) |
| A61P 35/00 | (2006.01) |
| A61P 37/04 | (2006.01) |
| A61P 37/06 | (2006.01) |

(52) U.S. Cl.
CPC ...... A61K 38/2013 (2013.01); A61K 47/6849 (2017.08); A61P 35/00 (2018.01); A61P 37/04 (2018.01); A61P 37/06 (2018.01)

(58) Field of Classification Search
CPC ...... A61K 38/2013; A61P 35/00; A61P 37/04; A61P 37/06; A61P 37/00; C07K 14/55; C07K 16/2866; C07K 2319/00; G01N 33/505
See application file for complete search history.

(56) References Cited

U.S. PATENT DOCUMENTS

2020/0024319 A1* 1/2020 Butz ....................... A61P 17/00

FOREIGN PATENT DOCUMENTS

| | | |
|---|---|---|
| JP | 2012-515778 A | 7/2012 |
| JP | 2016-514161 A | 5/2016 |
| WO | 01/27156 A1 | 4/2001 |
| WO | 2010/085495 A1 | 7/2010 |
| WO | 2014/153063 A1 | 9/2014 |
| WO | 2016/025385 A1 | 2/2016 |
| WO | 2018/234862 A1 | 12/2018 |
| WO | 2019/028425 A1 | 2/2019 |

OTHER PUBLICATIONS

Sharma et al. J Autoimmun. Mar. 2011 ; 36(2): 91-97. (Year: 2011).*
Mizui M. Clin Immunol. Sep. 2019;206:63-70. Epub Nov. 8, 2018. (Year: 2018).*
Ram et al. Bone Marrow Transplant. Apr. 2009;43(8):643-53. Epub Nov. 10, 2008. (Year: 2008).*
Carmenate et al. J Immunol. May 15, 2018;200(10):3475-3484. Epub Apr. 4, 2018. (Year: 2018).*
International Search Report issued in corresponding International Patent Application No. PCT/2020/058726 dated Jul. 15, 2020.
Rao et al., "High-affinity CD25-binding IL-2 mutants potently stimulate persistent T cell growth," Biochemistry, 44 (31): 10696-10701 (2005).
Liu et al., "Engineered Interleukin-2 Antagonists for the Inhibition of Regulatory T Cells," Journal of Immunotherapy, 32 (9): 887-894 (2009).
Levin et al., "Exploiting a natural conformational switch to engineer an interleukin-2 'superkine,'" Nature, 484 (7395): 529-535 (2012).
Caudana et al., "IL2/anti-IL2 complex combined with CTLA-4, but not PD-1, blockade rescues antitumor NK cell function by regulatory T-cell modulation," Cancer Immunology Research, 7 (3): 443-457 (2019).
Ward et al., "IL-2/CD25: A Long-Acting Fusion Protein That Promotes Immune Tolerance by Selectively Targeting the IL-2 Receptor on Regulatory T Cells," Journal of Immunology, 201 (9): 2579-2592 (2018).

(Continued)

*Primary Examiner* — Jeffrey Stucker
*Assistant Examiner* — Sarah Cooper Patterson
(74) *Attorney, Agent, or Firm* — Morgan, Lewis & Bockius LLP

(57) ABSTRACT

The invention relates to Interleukin-2 (IL-2) variants for the prevention or treatment of immune disorders, including with no limitations allergic, autoimmune, chronic or acute inflammatory and infectious diseases; graft-versus-host disease; graft rejection and cancer. The invention also relates to the use of said IL-2 variants for the screening of anti-IL-2 antibodies with pro-T-effector or pro-T-regulatory cell activity.

14 Claims, 16 Drawing Sheets

Specification includes a Sequence Listing.

(56)           References Cited

OTHER PUBLICATIONS

Leon et al., "Combining computational and experimental biology to develop therapeutically valuable IL2 muteins," Seminars in Oncology, 45 (1-2): 95-104 (2018).

"Extraordinary Superkines purge tumors and their immunosuppressive ecosystem," Medicenna Therapeutics Corporation B20 (2018).

Notice of Reasons for Rejection issued in Japanese Patent Application No. 2021-557787 dated Feb. 5, 2024.

Office Action issued in Australian Patent Application No. 2020252119 dated May 1, 2025.

Office Action issued in Korean Patent Application No. 10-2021-7035125 dated Apr. 28, 2025.

* cited by examiner

Figure 1:
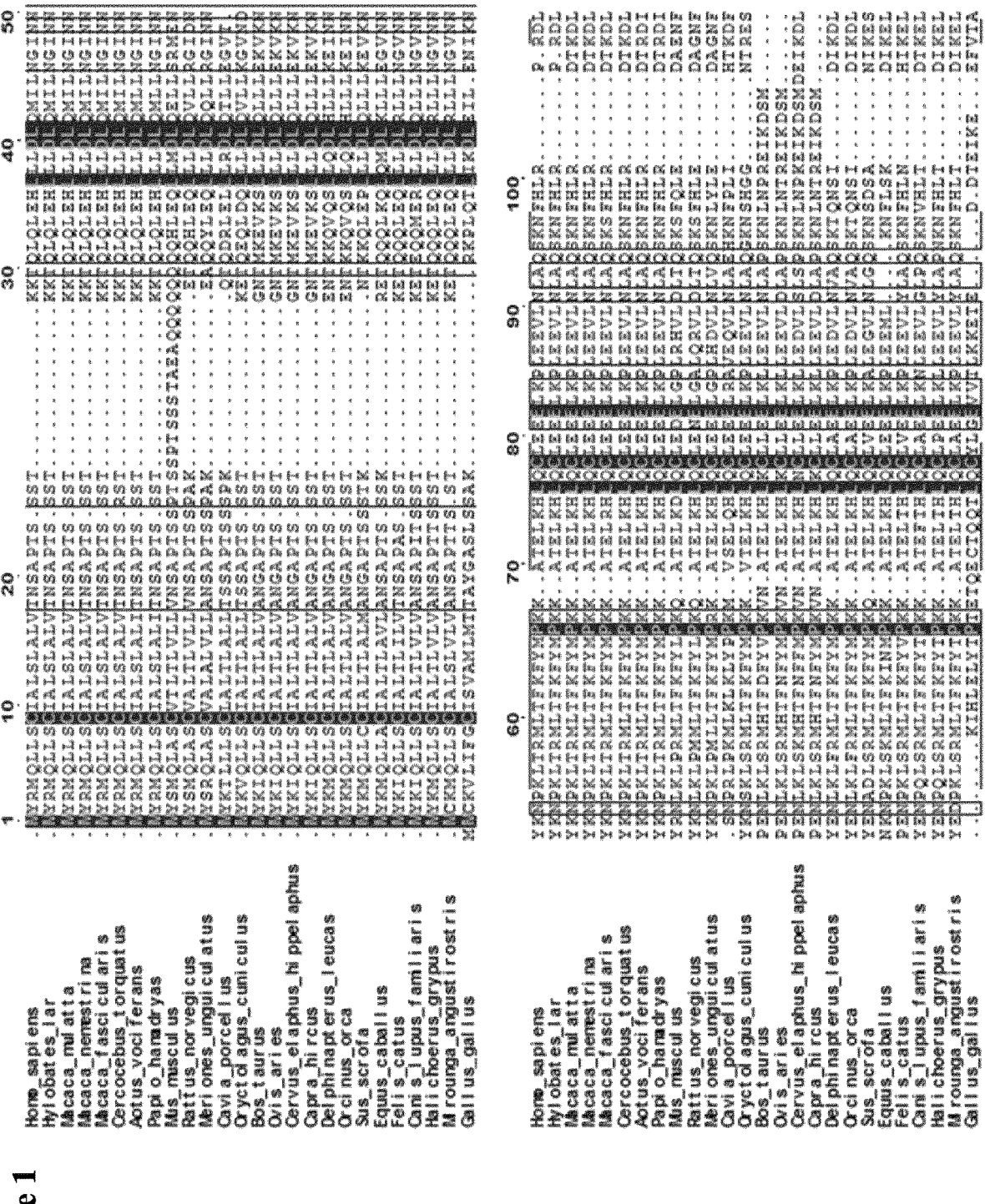

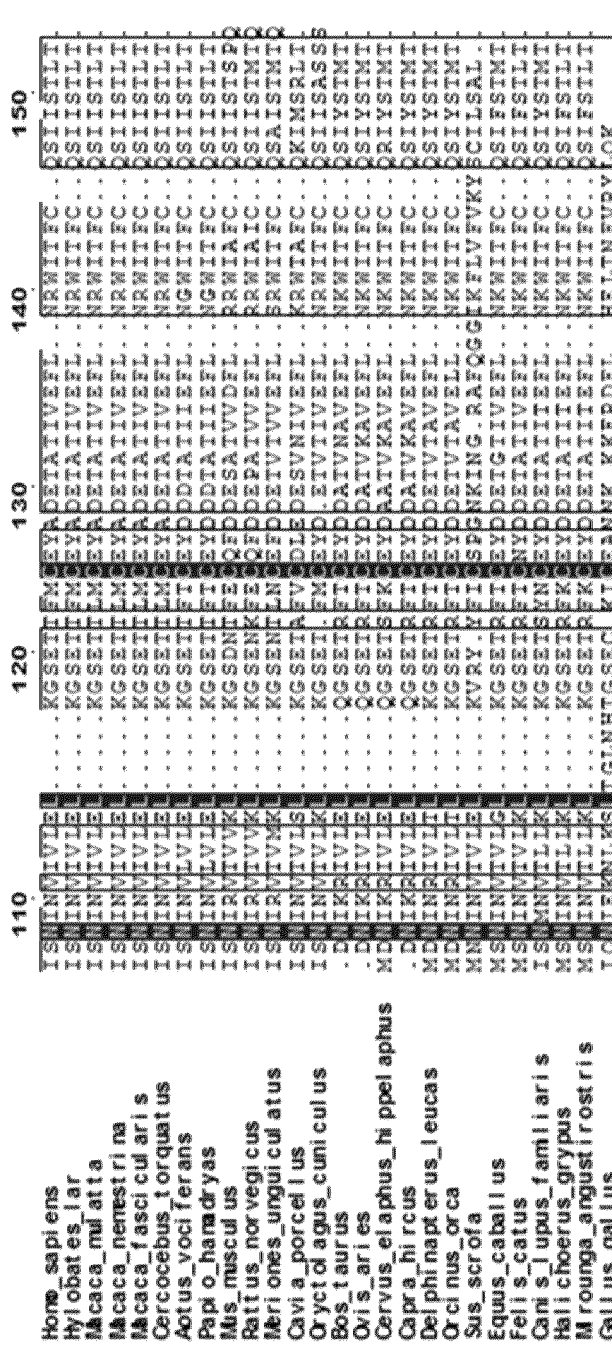
Figure 1(continuation)

Figure 3

A

B

A

B

Figure 8:
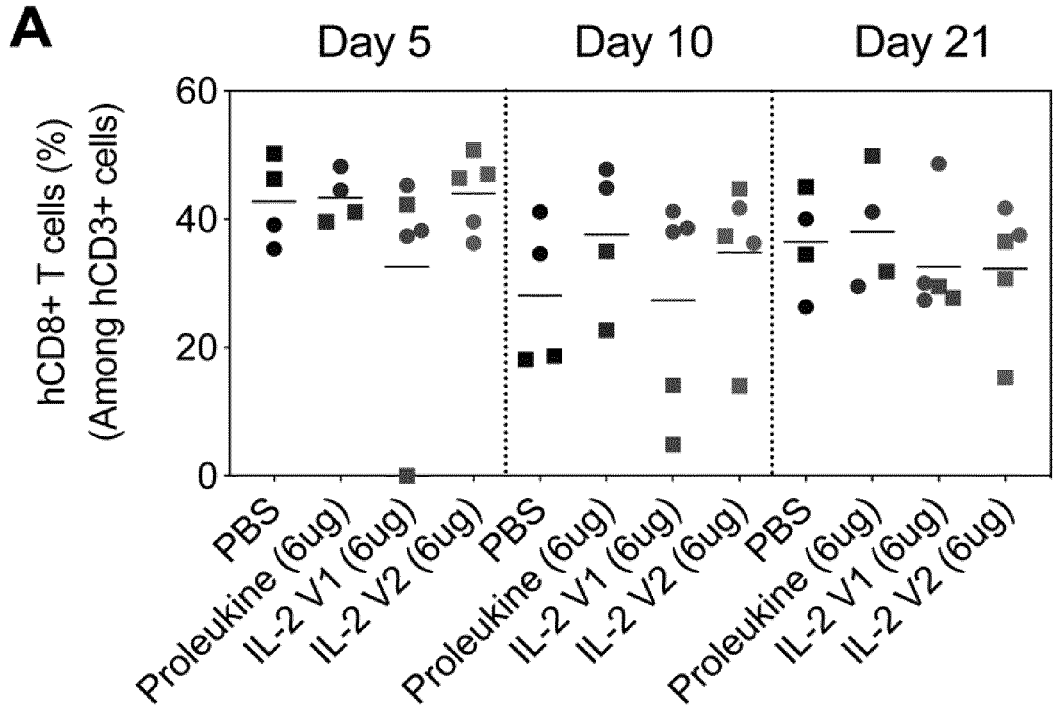
Figure 8:
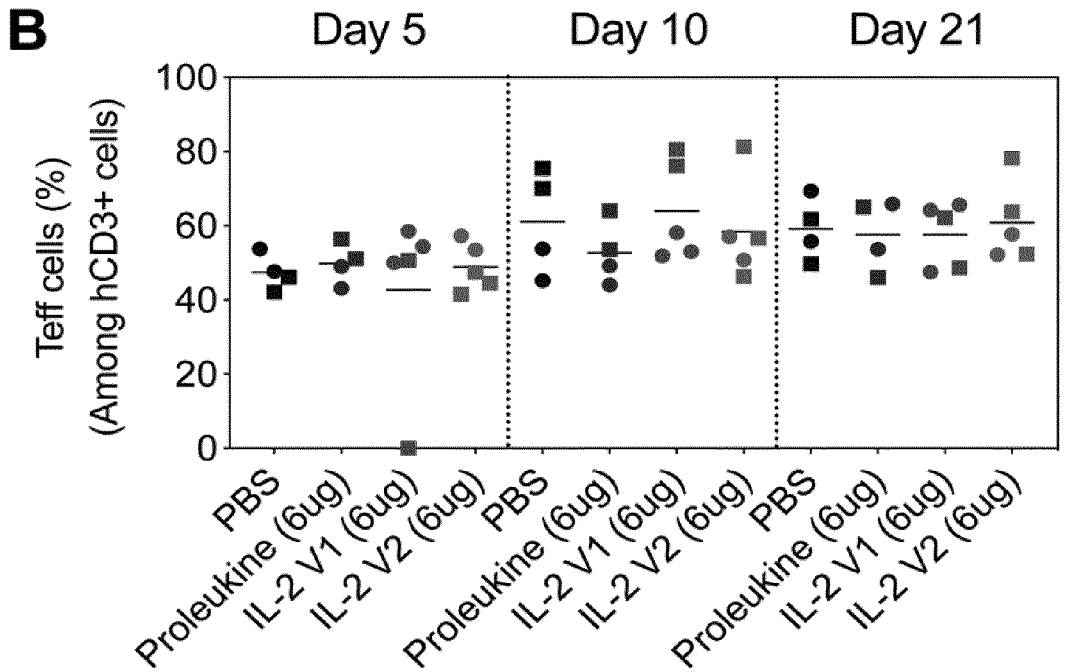

Figure 8 (continuation)
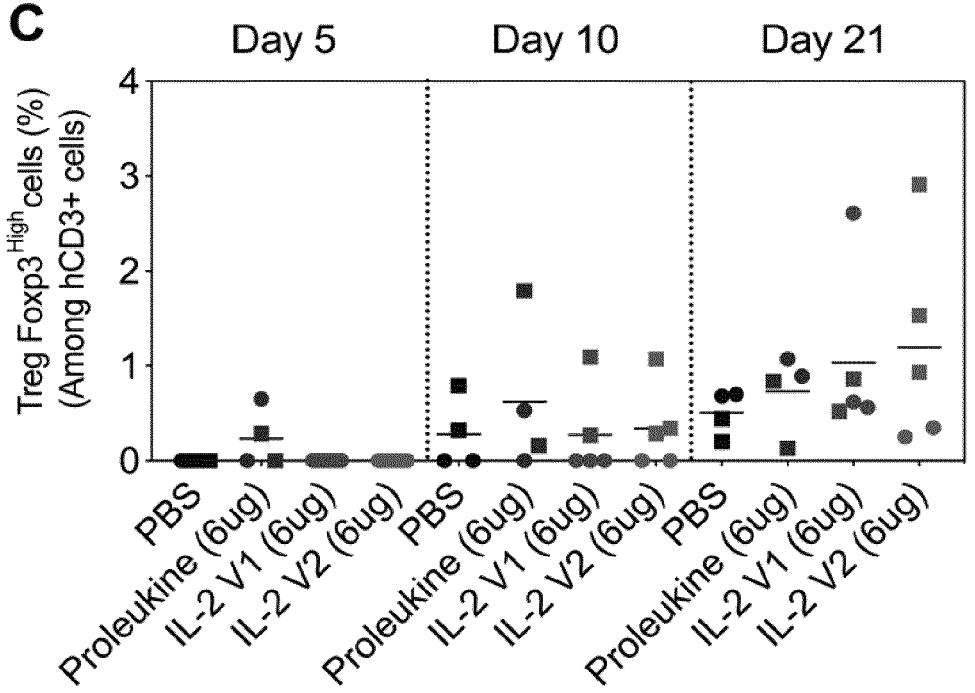
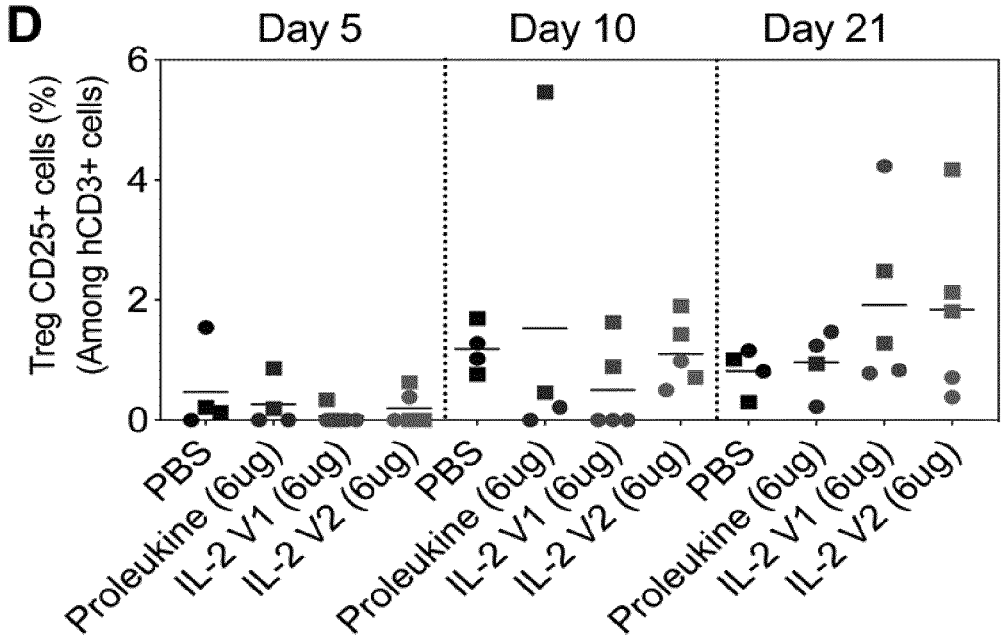

Figure 12:
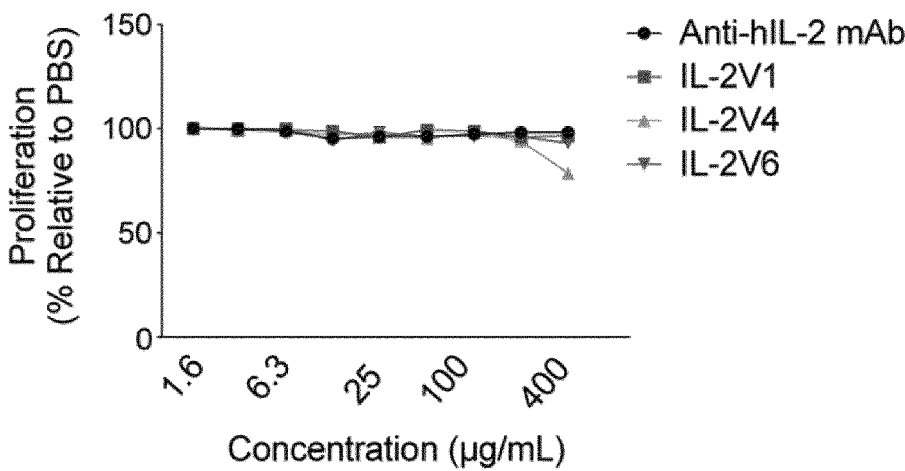
Figure 12:
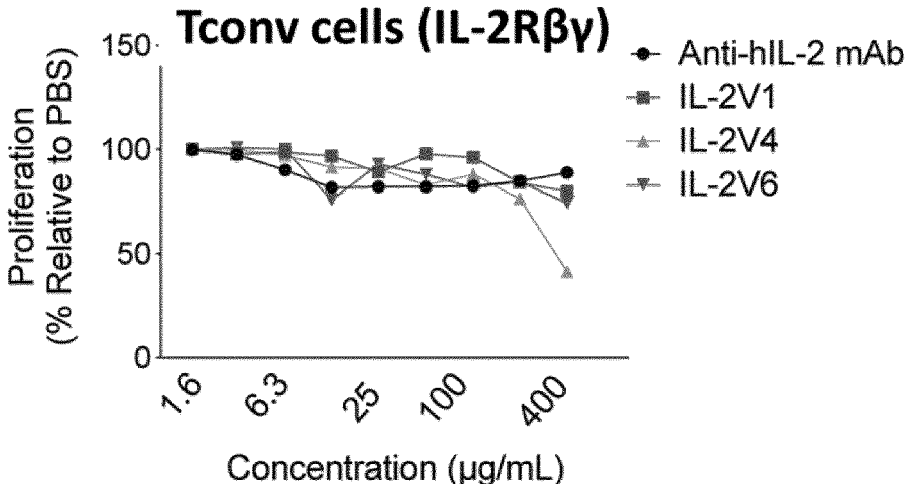
Figure 12:
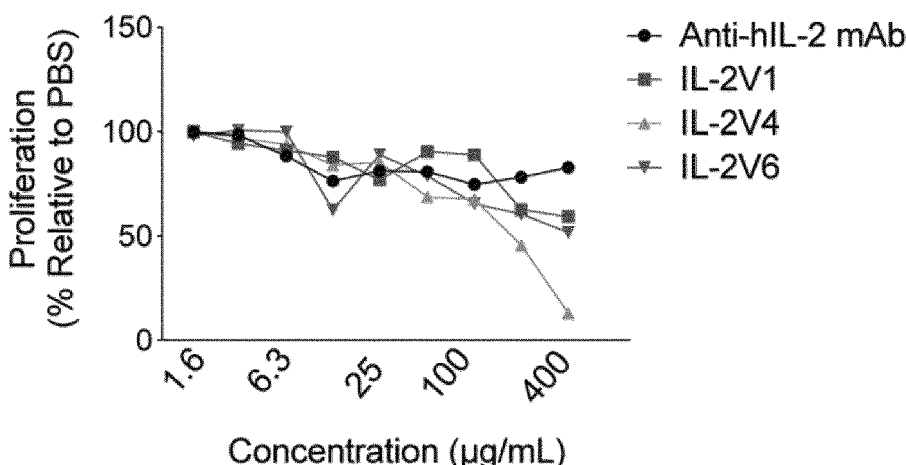

Figure 12 (continuation)
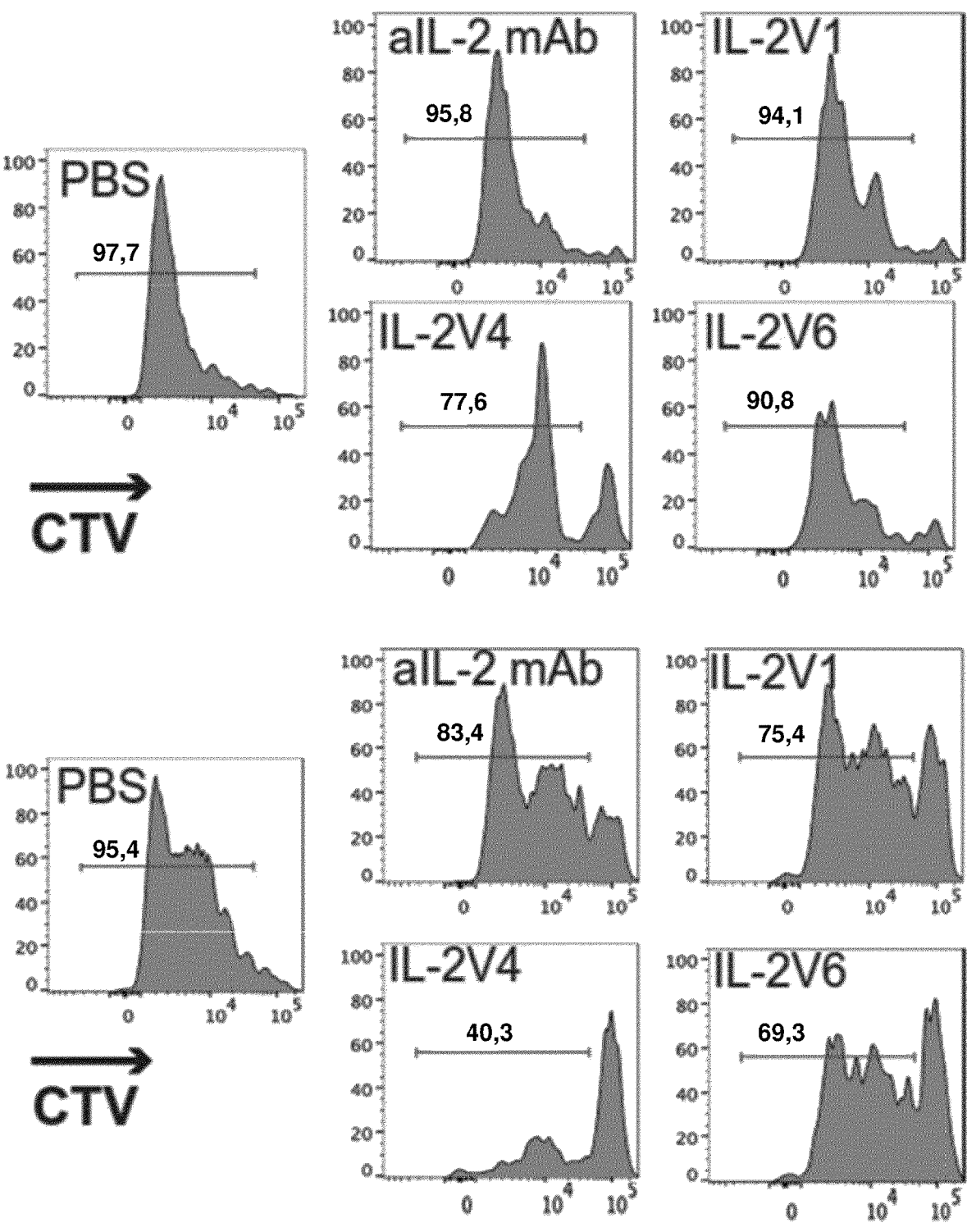

Figure 12 (continuation)
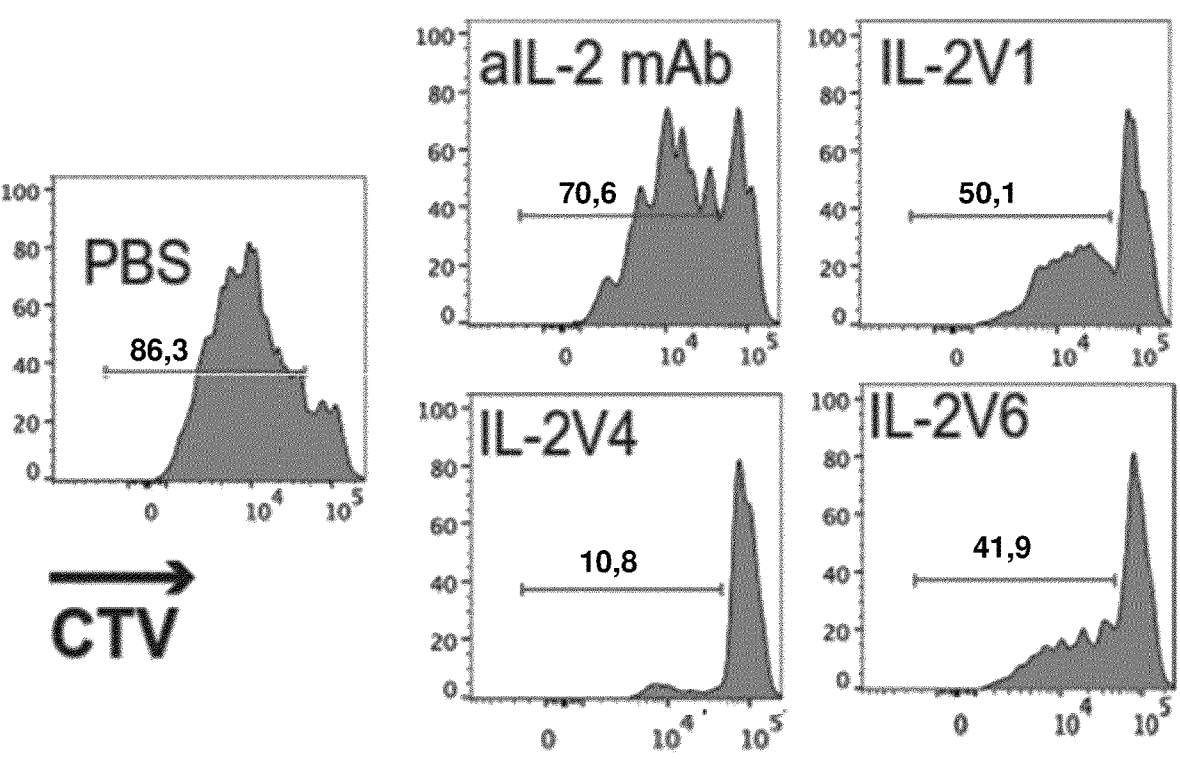

SEQUENCE LISTING

<160> NUMBER OF SEQ ID NOS: 39

<210> SEQ ID NO 1
<211> LENGTH: 133
<212> TYPE: PRT
<213> ORGANISM: homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45
```

-continued

```
Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Cys Gln Ser Ile
            115                 120                 125
```

```
Ile Ser Thr Leu Thr
    130
```

```
<210> SEQ ID NO 2
<211> LENGTH: 171
<212> TYPE: PRT
<213> ORGANISM: artificial sequence
<220> FEATURE:
<223> OTHER INFORMATION: synthetic polypeptide IL2-WT
```

```
<400> SEQUENCE: 2
```

```
Ala Pro Thr Ser Ser Thr Lys Lys Thr Gln Leu Gln Leu Glu His Leu
1               5                   10                  15
```

```
Leu Leu Asp Leu Gln Met Ile Leu Asn Gly Ile Asn Asn Tyr Lys Asn
                20                  25                  30
```

```
Pro Lys Leu Thr Arg Met Leu Thr Phe Lys Phe Tyr Met Pro Lys Lys
            35                  40                  45
```

```
Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
65                  70                  75                  80
```

```
Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
                100                 105                 110
```

```
Ile Val Glu Phe Leu Asn Arg Trp Ile Thr Phe Cys Gln Ser Ile Ile
            115                 120                 125
```

```
Ser Thr Leu Thr Gly Ala Leu Val Pro Arg Gly Ser Ser Ala Trp Ser
    130                 135                 140
```

```
His Pro Gln Phe Glu Lys Gly Gly Gly Ser Gly Gly Gly Ser Gly Gly
145                 150                 155                 160
```

```
Gly Ser Ala Trp Ser His Pro Gln Phe Glu Lys
                165                 170
```

```
<210> SEQ ID NO 3
<211> LENGTH: 171
<212> TYPE: PRT
<213> ORGANISM: artificial sequence
<220> FEATURE:
<223> OTHER INFORMATION: synthetic polypeptide IL2-V1
```

```
<400> SEQUENCE: 3
```

```
Ala Pro Thr Ser Ser Thr Lys Glu Thr Gln Glu Gln Leu Glu Arg Leu
1               5                   10                  15
```

```
Leu Arg Asp Leu Gln Leu Ile Leu Lys Gly Ile Asn Asn Tyr Lys Asn
                20                  25                  30
```

```
Pro Lys Leu Thr Arg Met Leu Thr Phe Lys Phe Tyr Met Pro Lys Lys
            35                  40                  45
```

-continued

```
Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Leu Arg
65              70              75              80

Pro Arg Asp Leu Ile Asn Asn Ile Asn Lys Ile Val Leu Lys Leu Lys
                85              90              95

Gly Ser Glu Thr Thr Phe Met Cys Glu Tyr Ala Asp Glu Thr Ala Thr
            100             105             110

Ile Val Glu Phe Leu Lys Arg Trp Ile Ala Phe Cys Gln Lys Ile Ile
        115             120             125

Ser Thr Leu Thr Gly Ala Leu Val Pro Arg Gly Ser Ser Ala Trp Ser
    130             135             140

His Pro Gln Phe Glu Lys Gly Gly Gly Ser Gly Gly Gly Ser Gly Gly
145             150             155             160

Gly Ser Ala Trp Ser His Pro Gln Phe Glu Lys
            165             170
```

<210> SEQ ID NO 4
<211> LENGTH: 171
<212> TYPE: PRT
<213> ORGANISM: artificial sequence
<220> FEATURE:
<223> OTHER INFORMATION: synthetic polypeptide IL2-V2

<400> SEQUENCE: 4

```
Ala Pro Thr Ser Ser Thr Lys Glu Thr Gln Glu Gln Leu Glu Arg Leu
1               5               10              15

Leu Arg Asp Leu Gln Leu Ile Leu Lys Gly Ile Asn Asn Pro Lys Asn
                20              25              30

Pro Lys Leu Thr Arg Met Leu Thr Phe Lys Phe Tyr Met Pro Lys Gln
        35              40              45

Ala Thr Ser Leu Lys His Leu Gln Cys Leu Glu Glu Glu Leu Lys Pro
    50              55              60

Leu Glu Glu Val Leu Asn Leu Ala Gln Ser Lys Asn Phe His Leu Glu
65              70              75              80

Pro Arg Asn Leu Ile Asn Asn Ile Asn Lys Ile Val Leu Lys Leu Lys
                85              90              95

Gly Ser Glu Thr Thr Phe Met Cys Glu Tyr Ala Asp Glu Thr Ala Thr
            100             105             110

Ile Val Glu Phe Leu Lys Arg Trp Ile Ala Phe Cys Gln Ser Ile Ile
        115             120             125

Ser Arg Ser Thr Gly Ala Leu Val Pro Arg Gly Ser Ser Ala Trp Ser
    130             135             140

His Pro Gln Phe Glu Lys Gly Gly Gly Ser Gly Gly Gly Ser Gly Gly
145             150             155             160

Gly Ser Ala Trp Ser His Pro Gln Phe Glu Lys
            165             170
```

<210> SEQ ID NO 5
<211> LENGTH: 171
<212> TYPE: PRT
<213> ORGANISM: artificial sequence
<220> FEATURE:
<223> OTHER INFORMATION: synthetic polypeptide IL2-V3

<400> SEQUENCE: 5

```
Ala Pro Thr Ser Ser Thr Lys Glu Thr Gln Glu Gln Leu Glu Arg Leu
```

-continued

```
1               5                   10                  15

Leu Arg Asp Leu Gln Leu Ile Leu Lys Gly Ile Asn Asn Pro Lys Asn
            20                  25                  30

Pro Lys Leu Thr Arg Met Leu Thr Phe Lys Phe Tyr Met Pro Lys Gln
        35                  40                  45

Ala Thr Ser Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Glu
65                  70                  75                  80

Pro Arg Asn Leu Ile Asn Asn Ile Asn Lys Ile Val Leu Lys Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
            115                 120                 125

Ser Arg Ser Thr Gly Ala Leu Val Pro Arg Gly Ser Ser Ala Trp Ser
    130                 135                 140

His Pro Gln Phe Glu Lys Gly Gly Gly Ser Gly Gly Gly Ser Gly Gly
145                 150                 155                 160

Gly Ser Ala Trp Ser His Pro Gln Phe Glu Lys
                165                 170
```

<210> SEQ ID NO 6
<211> LENGTH: 171
<212> TYPE: PRT
<213> ORGANISM: artificial sequence
<220> FEATURE:
<223> OTHER INFORMATION: synthetic polypeptide IL2-V4

<400> SEQUENCE: 6

```
Ala Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Pro Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
            115                 120                 125

Ser Thr Leu Thr Gly Ala Leu Val Pro Arg Gly Ser Ser Ala Trp Ser
    130                 135                 140

His Pro Gln Phe Glu Lys Gly Gly Gly Ser Gly Gly Gly Ser Gly Gly
145                 150                 155                 160

Gly Ser Ala Trp Ser His Pro Gln Phe Glu Lys
                165                 170
```

<210> SEQ ID NO 7
<211> LENGTH: 171
<212> TYPE: PRT

```
<213> ORGANISM: artificial sequence
<220> FEATURE:
<223> OTHER INFORMATION: synthetic polypeptide IL2-V5

<400> SEQUENCE: 7

Ala Pro Thr Ser Ser Thr Lys Glu Thr Gln Glu Gln Leu Glu Arg Leu
1               5                   10                  15

Leu Arg Asp Leu Gln Leu Ile Leu Lys Gly Ile Asn Asn Pro Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Asn Asn Ile Asn Lys Ile Val Leu Lys Leu Lys
                85                  90                  95

Gly Ser Glu Thr Thr Phe Met Cys Glu Tyr Ala Asp Glu Thr Ala Thr
            100                 105                 110

Ile Val Glu Phe Leu Lys Arg Trp Ile Ala Phe Cys Gln Lys Ile Ile
            115                 120                 125

Ser Thr Leu Thr Gly Ala Leu Val Pro Arg Gly Ser Ser Ala Trp Ser
        130                 135                 140

His Pro Gln Phe Glu Lys Gly Gly Gly Ser Gly Gly Gly Ser Gly Gly
145                 150                 155                 160

Gly Ser Ala Trp Ser His Pro Gln Phe Glu Lys
                165                 170

<210> SEQ ID NO 8
<211> LENGTH: 171
<212> TYPE: PRT
<213> ORGANISM: artificial sequence
<220> FEATURE:
<223> OTHER INFORMATION: synthetic polypeptide IL2-V6

<400> SEQUENCE: 8

Ala Pro Thr Ser Ser Thr Lys Glu Thr Gln Glu Gln Leu Glu Arg Leu
1               5                   10                  15

Leu Arg Asp Leu Gln Leu Ile Leu Lys Gly Ile Asn Asn Tyr Lys Asn
            20                  25                  30

Pro Lys Leu Thr Arg Met Leu Thr Phe Lys Phe Tyr Met Pro Lys Gln
            35                  40                  45

Ala Thr Ser Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Glu
65                  70                  75                  80

Pro Arg Asn Leu Ile Asn Asn Ile Asn Lys Ile Val Leu Lys Leu Lys
                85                  90                  95

Gly Ser Glu Thr Thr Phe Met Cys Glu Tyr Ala Asp Glu Thr Ala Thr
            100                 105                 110

Ile Val Glu Phe Leu Lys Arg Trp Ile Ala Phe Cys Gln Ser Ile Ile
            115                 120                 125

Ser Arg Ser Thr Gly Ala Leu Val Pro Arg Gly Ser Ser Ala Trp Ser
        130                 135                 140

His Pro Gln Phe Glu Lys Gly Gly Gly Ser Gly Gly Gly Ser Gly Gly
145                 150                 155                 160
```

-continued

Gly Ser Ala Trp Ser His Pro Gln Phe Glu Lys
            165                 170

<210> SEQ ID NO 9
<211> LENGTH: 531
<212> TYPE: DNA
<213> ORGANISM: artificial sequence
<220> FEATURE:
<223> OTHER INFORMATION: synthetic polynucleotide encoding IL2-v1

<400> SEQUENCE: 9
accggtgccc ccaccagctc cacaaaggag acccaggagc agctggagag gctgctgagg      60
gacctgcagc tgatcctgaa gggcatcaac aattacaaga acccaaagct gacacggatg     120
ctgaccttca gtttttatat gcccaagaag gccacagagc tgaagcacct gcagtgcctg     180
gaggaggagc tgaagcctct ggaggaggtg ctgaacctgg cccagtccaa gaatttccac     240
ctgcggccaa gagacctgat caacaatatc aataagatcg tgctgaagct gaagggctct     300
gagaccacct tcatgtgcga gtacgccgat gagaccgcca caatcgtgga gttcctgaag     360
cggtggatcg cctttttgtca gaagatcatc tctaccctga caggcgccct ggtgcccagg     420
ggctctagcg cctggagcca ccctcagttc gagaagggag aggaagcgg aggaggatcc     480 ggaggcggct ccgcctggtc tcaccctcag tttgagaagt agtaactcga g              531

<210> SEQ ID NO 10
<211> LENGTH: 531
<212> TYPE: DNA
<213> ORGANISM: artificial sequence
<220> FEATURE:
<223> OTHER INFORMATION: synthetic polynucleotide encoding IL2-v2

<400> SEQUENCE: 10
accggtgccc ccaccagctc cacaaaggag acccaggagc agctggagcg gctgctgaga      60
gacctgcagc tgatcctgaa gggcatcaac aatcccaaga accctaagct gacacggatg     120
ctgaccttca gtttttacat gcctaagcag gccacaagcc tgaagcacct gcagtgcctg     180
gaggaggagc tgaagcctct ggaggaggtg ctgaacctgg cccagtccaa gaatttccac     240
ctggagccac ggaacctgat caacaatatc aataagatcg tgctgaagct gaagggctct     300
gagaccacct tcatgtgcga gtatgccgat gagaccgcca caatcgtgga gttcctgaag     360
aggtggatcg cctttttgtca gtccatcatc tccaggtcta ccggcgccct ggtgccacgc     420
ggctctagcg cctggtctca cccacagttc gagaagggag aggatctgg aggaggaagc     480 ggaggcggca cgcctggtc ccacccccag tttgagaagt agtaactcga g              531

<210> SEQ ID NO 11
<211> LENGTH: 531
<212> TYPE: DNA
<213> ORGANISM: artificial sequence
<220> FEATURE:
<223> OTHER INFORMATION: synthetic polynucleotide encoding IL2-v3

<400> SEQUENCE: 11
accggtgccc ccaccagctc cacaaaggag acccaggagc agctggagcg gctgctgaga      60
gacctgcagc tgatcctgaa gggcatcaac aatcccaaga accctaagct gacacggatg     120
ctgaccttca gtttttacat gcctaagcag gccacaagcc tgaagcacct gcagtgcctg     180
gaggaggagc tgaagcctct ggaggaggtg ctgaacctgg cccagtccaa gaatttccac     240
ctggagccac ggaacctgat caacaatatc aataagatcg tgctgaagct gaagggctct     300

-continued

```
gagaccacct tcatgtgcga gtatgccgat gagaccgcca caatcgtgga gttcctgaac    360
aggtggatca ccttttgtca gtccatcatc tccaggtcta ccggcgccct ggtgccacgc    420
ggctctagcg cctggtctca cccacagttc gagaagggag gaggatctgg aggaggaagc    480
ggaggcggca gcgcctggtc ccaccccag tttgagaagt agtaactcga g    531
```

```
<210> SEQ ID NO 12
<211> LENGTH: 531
<212> TYPE: DNA
<213> ORGANISM: Artificial Sequence
<220> FEATURE:
<223> OTHER INFORMATION: synthetic polynucleotide encoding IL2-v4

<400> SEQUENCE: 12
```

```
accggtgccc ccaccagctc cacaaagaag acccagctgc agctggagca cctgctgctg     60
gacctgcaga tgatcctgaa cggcatcaac aatcccaaga atccaaagct gacacggatg    120
ctgaccttca gtttttatat gcccaagaag gccacagagc tgaagcacct gcagtgcctg    180
gaggaggagc tgaagcctct ggaggaggtg ctgaacctgg cccagtccaa gaatttccac    240
ctgcggccaa gagacctgat ctctaacatc aatgtgatcg tgctggagct gaagggcagc    300
gagaccacct tcatgtgcga gtacgccgat gagaccgcca caatcgtgga gttcctgaac    360
aggtggatca ccttttgtca gtccatcatc tctaccctga caggcgccct ggtgccccgc    420
ggctctagcg cctggtccca ccctcagttc gagaagggag gaggatctgg aggaggaagc    480
ggaggcggca gcgcctggag ccatcctcag tttgagaagt agtaactcga g    531
```

```
<210> SEQ ID NO 13
<211> LENGTH: 531
<212> TYPE: DNA
<213> ORGANISM: artificial sequence
<220> FEATURE:
<223> OTHER INFORMATION: synthetic polynucleotide encoding IL2-v5

<400> SEQUENCE: 13
```

```
accggtgccc ccaccagctc cacaaaggag acccaggagc agctggagag gctgctgagg     60
gacctgcagc tgatcctgaa gggcatcaac aatcccaaga acccaaagct gacacggatg    120
ctgaccttca gttttttatat gcccaagaag gccacagagc tgaagcacct gcagtgcctg    180
gaggaggagc tgaagcctct ggaggaggtg ctgaacctgg cccagtccaa gaatttccac    240
ctgcggccaa gagacctgat caacaatatc aataagatcg tgctgaagct gaagggctct    300
gagaccacct tcatgtgcga gtacgccgat gagaccgcca caatcgtgga gttcctgaag    360
cggtggatcg ccttttgtca gaagatcatc tctaccctga caggcgccct ggtgcccagg    420
ggctctagcg cctggagcca ccctcagttc gagaagggag gaggaagcgg aggaggatcc    480
ggaggcggct ccgcctggtc tcaccctcag tttgagaagt agtaactcga g    531
```

```
<210> SEQ ID NO 14
<211> LENGTH: 531
<212> TYPE: DNA
<213> ORGANISM: artificial sequence
<220> FEATURE:
<223> OTHER INFORMATION: synthetic polynucleotide encoding IL-2v6

<400> SEQUENCE: 14
```

```
accggtgccc ccaccagctc cacaaaggag acccaggagc agctggagcg gctgctgaga     60
gacctgcagc tgatcctgaa gggcatcaac aattacaaga accctaagct gacacggatg    120
ctgaccttca gttttttacat gcctaagcag gccacaagcc tgaagcacct gcagtgcctg    180
```

```
gaggaggagc tgaagcctct ggaggaggtg ctgaacctgg cccagtccaa gaatttccac      240
ctggagccac ggaacctgat caacaatatc aataagatcg tgctgaagct gaagggctct      300
gagaccacct tcatgtgcga gtatgccgat gagaccgcca caatcgtgga gttcctgaag      360
aggtggatcg cctttttgtca gtccatcatc tccaggtcta ccggcgccct ggtgccacgc      420
ggctctagcg cctggtctca cccacagttc gagaagggag gaggatctgg aggaggaagc      480
ggaggcggca gcgcctggtc ccaccccccag tttgagaagt agtaactcga g             531
```

```
<210> SEQ ID NO 15
<211> LENGTH: 153
<212> TYPE: PRT
<213> ORGANISM: Hylobates lar

<400> SEQUENCE: 15

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

```
<210> SEQ ID NO 16
<211> LENGTH: 154
<212> TYPE: PRT
<213> ORGANISM: Macaca mulatta

<400> SEQUENCE: 16

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Asp Thr Lys Asp Leu Ile Ser Asn Ile Asn Val
            100                 105                 110
```

-continued

```
Ile Val Leu Glu Leu Lys Gly Ser Glu Thr Thr Leu Met Cys Glu Tyr
        115                 120                 125

Ala Asp Glu Thr Ala Thr Ile Val Glu Phe Leu Asn Arg Trp Ile Thr
    130                 135                 140

Phe Cys Gln Ser Ile Ile Ser Thr Leu Thr
145                 150

<210> SEQ ID NO 17
<211> LENGTH: 154
<212> TYPE: PRT
<213> ORGANISM: Macaca nemestrina

<400> SEQUENCE: 17

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Asp Thr Lys Asp Leu Ile Ser Asn Ile Asn Val
            100                 105                 110

Ile Val Leu Glu Leu Lys Gly Ser Glu Thr Thr Leu Met Cys Glu Tyr
        115                 120                 125

Ala Asp Glu Thr Ala Thr Ile Val Glu Phe Leu Asn Arg Trp Ile Thr
    130                 135                 140

Phe Cys Gln Ser Ile Ile Ser Thr Leu Thr
145                 150

<210> SEQ ID NO 18
<211> LENGTH: 154
<212> TYPE: PRT
<213> ORGANISM: Macaca fascicularis

<400> SEQUENCE: 18

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Arg His Leu Gln Cys Leu Glu
65                  70                  75                  80

Glu Glu Leu Lys Pro Leu Glu Glu Val Leu Asn Leu Ala Gln Ser Lys
                85                  90                  95

Ser Phe His Leu Arg Asp Thr Lys Asp Leu Ile Ser Asn Ile Asn Val
            100                 105                 110

Ile Val Leu Glu Leu Lys Gly Ser Glu Thr Thr Leu Met Cys Glu Tyr
        115                 120                 125
```

-continued

```
Ala Asp Glu Thr Ala Thr Ile Val Glu Phe Leu Asn Arg Trp Ile Thr
    130                 135                 140

Phe Cys Gln Ser Ile Ile Ser Thr Leu Thr
145                 150

<210> SEQ ID NO 19
<211> LENGTH: 154
<212> TYPE: PRT
<213> ORGANISM: Cercocebus torquatus

<400> SEQUENCE: 19

Met Tyr Arg Met Gln Leu Leu Ser Cys Ile Ala Leu Ser Leu Ala Leu
1               5                   10                  15

Val Thr Asn Ser Ala Pro Thr Ser Arg Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Asp Thr Lys Asp Leu Ile Ser Asn Ile Asn Val
            100                 105                 110

Ile Val Leu Glu Leu Lys Gly Ser Glu Thr Thr Leu Met Cys Glu Tyr
        115                 120                 125

Ala Asp Glu Thr Ala Thr Ile Val Glu Phe Leu Asn Arg Trp Ile Thr
    130                 135                 140

Phe Cys Gln Ser Ile Ile Ser Thr Leu Thr
145                 150

<210> SEQ ID NO 20
<211> LENGTH: 154
<212> TYPE: PRT
<213> ORGANISM: Aotus vociferans

<400> SEQUENCE: 20

Met Tyr Arg Met Gln Leu Leu Ser Cys Ile Ala Leu Ser Leu Ala Leu
1               5                   10                  15

Ile Thr Asn Ser Ala Pro Thr Ser Ser Ser Thr Lys Lys Thr Gln Leu
                20                  25                  30

Gln Leu Glu His Leu Leu Leu Asp Leu Gln Met Leu Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Asp Thr Arg Asp Ile Ile Ser Asn Ile Asn Val
            100                 105                 110

Leu Val Leu Glu Leu Lys Gly Ser Glu Thr Thr Phe Thr Cys Glu Tyr
        115                 120                 125

Asp Asp Asp Thr Ala Thr Ile Ile Glu Phe Leu Asn Gly Trp Ile Thr
    130                 135                 140
```

-continued

```
Phe Cys Gln Ser Ile Ile Ser Thr Leu Thr
145                 150

<210> SEQ ID NO 21
<211> LENGTH: 154
<212> TYPE: PRT
<213> ORGANISM: Papio hamadryas

<400> SEQUENCE: 21

Met Tyr Arg Met Gln Leu Leu Ser Cys Ile Ala Leu Ser Leu Ala Leu
1               5                   10                  15

Ile Thr Asn Ser Ala Pro Thr Ser Ser Ser Thr Lys Lys Thr Gln Leu
            20                  25                  30

Gln Leu Glu His Leu Leu Leu Asp Leu Gln Met Leu Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Asp Thr Arg Asp Ile Ile Ser Asn Ile Asn Val
            100                 105                 110

Leu Val Leu Glu Leu Lys Gly Ser Glu Thr Thr Phe Thr Cys Glu Tyr
        115                 120                 125

Asp Asp Asp Thr Ala Thr Ile Ile Glu Phe Leu Asn Gly Trp Ile Thr
        130                 135                 140

Phe Cys Gln Ser Ile Ile Ser Thr Leu Thr
145                 150

<210> SEQ ID NO 22
<211> LENGTH: 169
<212> TYPE: PRT
<213> ORGANISM: Mus musculus

<400> SEQUENCE: 22

Met Tyr Ser Met Gln Leu Ala Ser Cys Val Thr Leu Thr Leu Val Leu
1               5                   10                  15

Leu Val Asn Ser Ala Pro Thr Ser Ser Pro Thr Ser Ser Pro Thr Ser
            20                  25                  30

Ser Ser Thr Ala Glu Ala Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
        130                 135                 140

Glu Ser Ala Thr Val Val Asp Phe Leu Arg Arg Trp Ile Ala Phe Cys
145                 150                 155                 160
```

-continued

Gln Ser Ile Ile Ser Thr Ser Pro Gln
                165

<210> SEQ ID NO 23
<211> LENGTH: 155
<212> TYPE: PRT
<213> ORGANISM: Rattus norvegicus

<400> SEQUENCE: 23

Met Tyr Ser Met Gln Leu Ala Ser Cys Val Ala Leu Thr Leu Val Leu
1               5                   10                  15

Leu Val Asn Ser Ala Pro Thr Ser Ser Pro Ala Lys Glu Thr Gln Gln
            20                  25                  30

His Leu Glu Gln Leu Leu Leu Asp Leu Gln Val Leu Leu Arg Gly Ile
        35                  40                  45

Asp Asn Tyr Lys Asn Leu Lys Leu Pro Met Met Leu Thr Phe Lys Phe
    50                  55                  60

Tyr Leu Pro Lys Gln Ala Thr Glu Leu Lys His Leu Gln Cys Leu Glu
65                  70                  75                  80

Asn Glu Leu Gly Ala Leu Gln Arg Val Leu Asp Leu Thr Gln Ser Lys
                85                  90                  95

Ser Phe His Leu Glu Asp Ala Gly Asn Phe Ile Ser Asn Ile Arg Val
            100                 105                 110

Thr Val Val Lys Leu Lys Gly Ser Glu Asn Lys Phe Glu Cys Gln Phe
            115                 120                 125

Asp Asp Glu Pro Ala Thr Val Val Glu Phe Leu Arg Arg Trp Ile Ala
        130                 135                 140

Ile Cys Gln Ser Ile Ile Ser Thr Met Thr Gln
145                 150                 155

<210> SEQ ID NO 24
<211> LENGTH: 155
<212> TYPE: PRT
<213> ORGANISM: Meriones unguiculatus

<400> SEQUENCE: 24

Met Tyr Ser Arg Gln Leu Ala Ser Cys Val Ala Leu Ala Leu Val Leu
1               5                   10                  15

Leu Ala Asn Ser Ala Pro Thr Ser Ser Pro Ala Lys Glu Ala Gln Gln
            20                  25                  30

Tyr Leu Glu Gln Leu Leu Leu Asp Leu Gln Gln Leu Leu Arg Gly Ile
        35                  40                  45

Asn Asn Tyr Lys Asn Pro Lys Leu Pro Met Leu Leu Thr Phe Lys Phe
    50                  55                  60

Tyr Met Pro Arg Lys Ala Thr Glu Leu Lys His Leu Gln Cys Leu Glu
65                  70                  75                  80

Glu Glu Leu Gly Pro Leu His Asp Val Leu Asn Leu Val Gln Ser Lys
                85                  90                  95

Asn Leu Tyr Leu Glu Asp Ala Gly Asn Phe Ile Ser Asn Ile Arg Val
            100                 105                 110

Thr Val Met Lys Leu Lys Gly Ser Glu Asn Thr Leu Asn Cys Glu Phe
            115                 120                 125

Asp Asp Glu Thr Val Thr Val Val Glu Phe Leu Ser Arg Trp Ile Thr
        130                 135                 140

Phe Cys Gln Ser Ala Ile Ser Thr Met Thr Gln
145                 150                 155

-continued

<210> SEQ ID NO 25
<211> LENGTH: 152
<212> TYPE: PRT
<213> ORGANISM: Cavia porcellus

<400> SEQUENCE: 25

Met Tyr Lys Thr Leu Leu Leu Ser Cys Leu Ala Leu Thr Leu Ala Leu
1               5                   10                  15

Leu Thr Ser Ser Ala Pro Thr Ser Ser Ser Pro Lys Gln Thr Gln Asp
                20                  25                  30

Arg Leu Glu Leu Leu Leu Arg Asp Leu Gln Thr Leu Leu Glu Gly Val
            35                  40                  45

Thr Ser Asn Pro Arg Leu Pro Lys Met Leu Lys Leu Lys Leu Tyr Pro
        50                  55                  60

Pro Lys Met Val Ser Glu Leu Gln His Leu Gln Cys Leu Glu Glu Glu
65                  70                  75                  80

Leu Arg Ala Val Glu Gln Val Leu Asn Leu Ala Glu His Lys Asn Phe
                85                  90                  95

Pro Leu Ile His Thr Lys Asp Phe Ile Ser Asn Ile Asn Val Thr Val
            100                 105                 110

Leu Ser Leu Lys Gly Ser Glu Thr Ala Phe Val Cys Asp Leu Glu Asp
        115                 120                 125

Glu Ser Val Asn Ile Val Glu Phe Leu Lys Arg Trp Thr Ala Phe Cys
    130                 135                 140

Gln Lys Ile Met Ser Arg Leu Thr
145                 150

<210> SEQ ID NO 26
<211> LENGTH: 153
<212> TYPE: PRT
<213> ORGANISM: Oryctolagus cuniculus

<400> SEQUENCE: 26

Met Tyr Lys Val Gln Leu Leu Ser Cys Ile Ala Leu Thr Leu Ala Leu
1               5                   10                  15

Leu Thr Ser Ser Ala Pro Thr Ser Ser Ser Thr Lys Glu Thr Gln Glu
                20                  25                  30

Gln Leu Asp Gln Leu Leu Leu Asp Leu Gln Val Leu Leu Lys Gly Val
            35                  40                  45

Asn Asp Tyr Lys Asn Ser Lys Leu Ser Arg Met Leu Thr Phe Lys Phe
        50                  55                  60

Tyr Met Pro Lys Lys Val Thr Glu Leu Lys His Leu Gln Cys Leu Glu
65                  70                  75                  80

Glu Glu Leu Lys Pro Leu Glu Glu Val Leu Asn Leu Ala Gln Gly Lys
                85                  90                  95

Asn Ser His Gly Gly Asn Thr Arg Glu Ser Ile Ser Asn Ile Asn Val
            100                 105                 110

Thr Val Leu Lys Leu Lys Gly Ser Glu Thr Phe Met Cys Glu Tyr Asp
        115                 120                 125

Glu Thr Val Thr Ile Val Glu Phe Leu Asn Arg Trp Ile Thr Phe Cys
    130                 135                 140

Gln Ser Ile Ile Ser Ala Ser Ser Ser
145                 150

<210> SEQ ID NO 27

```
<211> LENGTH: 155
<212> TYPE: PRT
<213> ORGANISM: Bos taurus

<400> SEQUENCE: 27

Met Tyr Lys Ile Gln Leu Leu Ser Cys Ile Ala Leu Thr Leu Ala Leu
1               5                   10                  15

Val Ala Asn Gly Ala Pro Thr Ser Ser Ser Thr Gly Asn Thr Met Lys
                20                  25                  30

Glu Val Lys Ser Leu Leu Leu Asp Leu Gln Leu Leu Leu Glu Lys Val
                35                  40                  45

Lys Asn Pro Glu Asn Leu Lys Leu Ser Arg Met His Thr Phe Asp Phe
        50                  55                  60

Tyr Val Pro Lys Val Asn Ala Thr Glu Leu Lys His Leu Lys Cys Leu
65                  70                  75                  80

Leu Glu Glu Leu Lys Leu Leu Glu Glu Val Leu Asn Leu Ala Pro Ser
                85                  90                  95

Lys Asn Leu Asn Pro Arg Glu Ile Lys Asp Ser Met Asp Asn Ile Lys
                100                 105                 110

Arg Ile Val Leu Glu Leu Gln Gly Ser Glu Thr Arg Phe Thr Cys Glu
                115                 120                 125

Tyr Asp Asp Ala Thr Val Asn Ala Val Glu Phe Leu Asn Lys Trp Ile
        130                 135                 140

Thr Phe Cys Gln Ser Ile Tyr Ser Thr Met Thr
145                 150                 155

<210> SEQ ID NO 28
<211> LENGTH: 155
<212> TYPE: PRT
<213> ORGANISM: Ovis aries

<400> SEQUENCE: 28

Met Tyr Lys Ile Gln Leu Leu Ser Cys Ile Ala Leu Thr Leu Ala Leu
1               5                   10                  15

Val Ala Asn Gly Ala Pro Thr Ser Ser Ser Thr Gly Asn Thr Met Lys
                20                  25                  30

Glu Val Lys Ser Leu Leu Leu Asp Leu Gln Leu Leu Leu Glu Lys Val
                35                  40                  45

Lys Asn Pro Glu Asn Leu Lys Leu Ser Arg Met His Thr Phe Asn Phe
        50                  55                  60

Tyr Met Pro Lys Val Asn Ala Thr Glu Leu Lys His Leu Lys Cys Leu
65                  70                  75                  80

Leu Glu Glu Leu Lys Leu Leu Glu Glu Val Leu Asp Leu Ala Pro Ser
                85                  90                  95

Lys Asn Leu Asn Thr Arg Glu Ile Lys Asp Ser Met Asp Asn Ile Lys
                100                 105                 110

Arg Ile Val Leu Glu Leu Gln Gly Ser Glu Thr Arg Phe Thr Cys Glu
                115                 120                 125

Tyr Asp Asp Ala Thr Val Lys Ala Val Glu Phe Leu Asn Lys Trp Ile
        130                 135                 140

Thr Phe Cys Gln Ser Ile Tyr Ser Thr Met Thr
145                 150                 155

<210> SEQ ID NO 29
<211> LENGTH: 162
<212> TYPE: PRT
<213> ORGANISM: Cervus elaphus
```

-continued

```
<400> SEQUENCE: 29

Met Tyr Lys Ile Gln Leu Leu Ser Cys Ile Ala Leu Thr Leu Ala Leu
1               5                   10                  15

Val Ala Asn Gly Ala Pro Thr Ser Ser Ser Thr Gly Asn Thr Met Lys
                20                  25                  30

Glu Val Lys Ser Leu Leu Leu Asp Leu Gln Leu Leu Leu Glu Lys Val
            35                  40                  45

Lys Asn Pro Glu Asn Leu Lys Leu Ser Lys Met His Thr Phe Asn Phe
        50                  55                  60

Phe Met Pro Lys Val Asn Ala Thr Glu Leu Lys His Leu Asn Cys Leu
65                  70                  75                  80

Leu Glu Glu Leu Lys Leu Leu Glu Asp Val Leu Ser Leu Ser Pro Ser
                85                  90                  95

Lys Asn Leu Asn Pro Lys Glu Ile Lys Asp Ser Met Asp Glu Ile Lys
                100                 105                 110

Asp Leu Met Asp Asn Ile Lys Arg Ile Val Leu Glu Leu Gln Gly Ser
            115                 120                 125

Glu Thr Ser Phe Lys Cys Glu Tyr Asp Ala Ala Thr Val Lys Ala Val
        130                 135                 140

Glu Phe Leu Asn Lys Trp Ile Thr Phe Cys Gln Arg Ile Tyr Ser Thr
145                 150                 155                 160

Met Thr

<210> SEQ ID NO 30
<211> LENGTH: 155
<212> TYPE: PRT
<213> ORGANISM: Capra hircus

<400> SEQUENCE: 30

Met Tyr Lys Ile Gln Leu Leu Ser Cys Ile Ala Leu Thr Leu Ala Leu
1               5                   10                  15

Val Ala Asn Gly Ala Pro Thr Ser Ser Ser Thr Gly Asn Thr Met Lys
                20                  25                  30

Glu Val Lys Ser Leu Leu Leu Asp Leu Gln Leu Leu Leu Glu Lys Val
            35                  40                  45

Lys Asn Pro Glu Asn Leu Lys Leu Ser Arg Met His Thr Phe Asn Phe
        50                  55                  60

Tyr Met Pro Lys Val Asn Ala Thr Glu Leu Lys His Leu Lys Cys Leu
65                  70                  75                  80

Leu Glu Glu Leu Lys Leu Leu Glu Glu Val Leu Asp Leu Ala Pro Ser
                85                  90                  95

Lys Asn Leu Asn Thr Arg Glu Ile Lys Asp Ser Met Asp Asn Ile Lys
                100                 105                 110

Arg Ile Val Leu Glu Leu Gln Gly Ser Glu Thr Arg Phe Thr Cys Glu
            115                 120                 125

Tyr Asp Asp Ala Thr Val Lys Ala Val Glu Phe Leu Asn Lys Trp Ile
        130                 135                 140

Thr Phe Cys Gln Ser Ile Tyr Ser Thr Met Thr
145                 150                 155

<210> SEQ ID NO 31
<211> LENGTH: 154
<212> TYPE: PRT
<213> ORGANISM: Delphinapterus leucas
```

```
<400> SEQUENCE: 31

Met Tyr Lys Met Gln Leu Leu Ser Cys Ile Ala Leu Thr Leu Ala Leu
1               5                   10                  15

Val Ala Asn Gly Ala Pro Thr Ser Ser Ser Thr Glu Asn Thr Lys Lys
                20                  25                  30

Gln Val Gln Ser Leu Leu Gln Asp Leu His Leu Leu Leu Lys Glu Ile
            35                  40                  45

Asn Asn Tyr Glu Asn Leu Lys Leu Phe Arg Met Leu Thr Phe Lys Phe
        50                  55                  60

Tyr Met Pro Lys Lys Ala Thr Glu Leu Lys His Leu Gln Cys Leu Ala
65                  70                  75                  80

Glu Glu Leu Lys Pro Leu Glu Asp Val Leu Asn Val Ala Gln Ser Lys
                85                  90                  95

Thr Gln Asn Ser Ile Asp Ile Lys Asp Leu Met Asp Asn Ile Asn Arg
            100                 105                 110

Ile Val Leu Thr Leu Lys Gly Ser Glu Thr Arg Phe Thr Cys Glu Tyr
        115                 120                 125

Asp Asp Glu Thr Val Thr Ala Val Glu Phe Leu Asn Lys Trp Ile Thr
    130                 135                 140

Phe Cys Gln Ser Ile Tyr Ser Thr Met Thr
145                 150

<210> SEQ ID NO 32
<211> LENGTH: 154
<212> TYPE: PRT
<213> ORGANISM: Orcinus orca

<400> SEQUENCE: 32

Met Tyr Lys Met Gln Leu Leu Ser Cys Ile Ala Leu Thr Leu Ala Leu
1               5                   10                  15

Val Ala Asn Gly Ala Pro Thr Ser Ser Ser Thr Glu Asn Thr Lys Lys
                20                  25                  30

Gln Val Gln Ser Leu Leu Gln Asp Leu His Leu Leu Leu Lys Glu Ile
            35                  40                  45

Asn Asn Tyr Glu Asn Leu Lys Leu Phe Arg Met Leu Thr Phe Lys Phe
        50                  55                  60

Tyr Met Pro Lys Lys Ala Thr Glu Leu Lys His Leu Gln Cys Leu Ala
65                  70                  75                  80

Glu Glu Leu Lys Pro Leu Glu Asp Val Leu Asn Val Ala Gln Ser Lys
                85                  90                  95

Thr Gln Asn Ser Ile Asp Ile Lys Asp Leu Met Asp Asn Ile Asn Arg
            100                 105                 110

Ile Val Leu Thr Leu Lys Gly Ser Glu Thr Arg Phe Thr Cys Glu Tyr
        115                 120                 125

Asp Asp Glu Thr Val Thr Ala Val Glu Leu Leu Asn Lys Trp Ile Thr
    130                 135                 140

Phe Cys Gln Ser Ile Tyr Ser Thr Met Thr
145                 150

<210> SEQ ID NO 33
<211> LENGTH: 155
<212> TYPE: PRT
<213> ORGANISM: Sus scrofa

<400> SEQUENCE: 33

Met Tyr Lys Met Gln Leu Leu Cys Cys Ile Ala Leu Thr Leu Ala Leu
```

-continued

```
1              5              10             15

Met Ala Asn Gly Ala Pro Thr Ser Ser Ser Thr Lys Asn Thr Lys Lys
            20             25             30

Gln Leu Glu Pro Leu Leu Leu Asp Leu Gln Leu Leu Leu Lys Glu Val
            35             40             45

Lys Asn Tyr Glu Asn Ala Asp Leu Ser Arg Met Leu Thr Phe Lys Phe
        50             55             60

Tyr Met Pro Lys Gln Ala Thr Glu Leu Lys His Leu Gln Cys Leu Val
65             70             75             80

Glu Glu Leu Lys Ala Leu Glu Gly Val Leu Asn Leu Gly Gln Ser Lys
            85             90             95

Asn Ser Asp Ser Ala Asn Ile Lys Glu Ser Met Asn Asn Ile Asn Val
            100            105            110

Thr Val Leu Glu Leu Lys Val Arg Tyr Tyr Phe Ile Cys Ser Pro Gly
            115            120            125

Asn Lys Ile Asn Gly Arg Ala Phe Gln Gly Gly Ile Lys Phe Leu Val
        130            135            140

Phe Val Lys Tyr Ser Cys Ile Leu Ser Ala Leu
145            150            155
```

```
<210> SEQ ID NO 34
<211> LENGTH: 149
<212> TYPE: PRT
<213> ORGANISM: Equus caballus

<400> SEQUENCE: 34

Met Tyr Lys Met Gln Leu Leu Ala Cys Ile Ala Leu Thr Leu Ala Val
1              5              10             15

Leu Ala Asn Ser Ala Pro Thr Ser Ser Ser Lys Arg Glu Thr Gln Gln
            20             25             30

Gln Leu Lys Gln Leu Gln Met Asp Leu Lys Leu Leu Leu Glu Gly Val
            35             40             45

Asn Asn Asn Lys Asn Pro Lys Leu Ser Lys Met Leu Thr Phe Lys Ile
        50             55             60

Asn Met Pro Lys Lys Ala Thr Glu Leu Lys His Leu Gln Cys Leu Glu
65             70             75             80

Glu Glu Leu Lys Pro Leu Glu Glu Met Leu Lys Asn Phe Leu Ser Lys
            85             90             95

Asp Ile Lys Glu Leu Met Ser Asn Ile Asn Val Thr Val Leu Gly Leu
            100            105            110

Lys Gly Ser Glu Thr Arg Phe Thr Cys Glu Tyr Asp Asp Glu Thr Gly
        115            120            125

Thr Ile Val Glu Phe Leu Asn Lys Trp Ile Thr Phe Cys Gln Ser Ile
        130            135            140

Phe Ser Thr Met Thr
145
```

```
<210> SEQ ID NO 35
<211> LENGTH: 154
<212> TYPE: PRT
<213> ORGANISM: Felis catus

<400> SEQUENCE: 35

Met Tyr Lys Ile Gln Leu Leu Ser Cys Ile Ala Leu Thr Leu Ile Leu
1              5              10             15

Val Thr Asn Ser Ala Pro Ala Ser Ser Ser Thr Lys Glu Thr Gln Gln
```

-continued

```
            20              25              30

Gln Leu Glu Gln Leu Leu Leu Asp Leu Arg Leu Leu Leu Asn Gly Val
        35              40              45

Asn Asn Pro Glu Asn Pro Lys Leu Ser Arg Met Leu Thr Phe Lys Phe
    50              55              60

Tyr Val Pro Lys Lys Ala Thr Glu Leu Thr His Leu Gln Cys Leu Val
65              70              75              80

Glu Glu Leu Lys Pro Leu Glu Glu Val Leu Tyr Leu Ala Gln Ser Lys
                85              90              95

Asn Phe His Leu Asn His Ile Lys Glu Leu Met Ser Asn Ile Asn Val
            100             105             110

Thr Val Leu Lys Leu Lys Gly Ser Glu Thr Arg Phe Thr Cys Asn Tyr
        115             120             125

Asp Asp Glu Thr Ala Thr Ile Val Glu Phe Leu Asn Lys Trp Ile Thr
    130             135             140

Phe Cys Gln Ser Ile Phe Ser Thr Leu Thr
145             150
```

<210> SEQ ID NO 36
<211> LENGTH: 155
<212> TYPE: PRT
<213> ORGANISM: Canis lupus

<400> SEQUENCE: 36

```
Met Tyr Lys Ile Gln Leu Leu Ser Cys Ile Ala Leu Thr Leu Val Leu
1               5               10              15

Val Ala Asn Ser Ala Pro Ile Thr Ser Ser Ser Thr Lys Glu Thr Glu
            20              25              30

Gln Gln Met Glu Arg Leu Leu Leu Asp Leu Gln Leu Leu Leu Asn Gly
        35              40              45

Val Asn Asn Tyr Glu Asn Pro Gln Leu Ser Arg Met Leu Thr Phe Lys
    50              55              60

Phe Tyr Thr Pro Lys Lys Ala Thr Glu Phe Thr His Leu Gln Cys Leu
65              70              75              80

Ala Glu Glu Leu Lys Asn Leu Glu Glu Val Leu Gly Leu Pro Gln Ser
                85              90              95

Lys Asn Val His Leu Thr Asp Thr Lys Glu Leu Ile Ser Asn Met Asn
            100             105             110

Val Thr Leu Leu Lys Leu Lys Gly Ser Glu Thr Ser Tyr Asn Cys Glu
        115             120             125

Tyr Asp Asp Glu Thr Ala Thr Ile Thr Glu Phe Leu Asn Lys Trp Ile
    130             135             140

Thr Phe Cys Gln Ser Ile Tyr Ser Thr Met Thr
145             150             155
```

<210> SEQ ID NO 37
<211> LENGTH: 154
<212> TYPE: PRT
<213> ORGANISM: Halichoerus grypus

<400> SEQUENCE: 37

```
Met Tyr Lys Met Gln Leu Leu Ser Cys Ile Ala Leu Thr Leu Val Leu
1               5               10              15

Val Ala Asn Ser Ala Pro Thr Thr Ser Ser Ser Thr Lys Glu Thr Gln
            20              25              30

Gln Gln Leu Glu Gln Leu Leu Leu Asp Leu Arg Leu Leu Leu Asn Gly
```

```
            35              40              45

Val Asn Asn Tyr Glu Asn Pro Gln Leu Ser Arg Met Leu Thr Phe Lys
    50              55              60

Phe Tyr Thr Pro Lys Lys Ala Thr Glu Leu Thr His Leu Gln Cys Leu
65              70              75              80

Pro Glu Glu Leu Lys Leu Leu Glu Glu Val Leu Tyr Leu Ala Pro Asn
                85              90              95

Lys Asn Phe His Leu Thr Asp Ile Lys Glu Leu Met Ser Asn Ile Asn
                100             105             110

Val Thr Leu Leu Lys Leu Lys Gly Ser Glu Thr Arg Phe Lys Cys Glu
                115             120             125

Tyr Asp Asp Glu Thr Ala Thr Ile Thr Glu Phe Leu Asn Lys Trp Ile
    130             135             140

Thr Phe Cys Ser Ile Phe Ser Thr Leu Thr
145             150
```

<210> SEQ ID NO 38
<211> LENGTH: 154
<212> TYPE: PRT
<213> ORGANISM: Mirounga angustirostris

<400> SEQUENCE: 38

```
Met Cys Lys Met Gln Leu Leu Ser Cys Ile Ala Leu Ser Leu Val Leu
1               5               10              15

Val Ala Asn Ser Ala Pro Thr Thr Ser Ser Thr Lys Glu Thr Gln Gln
                20              25              30

Gln Leu Glu Gln Leu Leu Leu Asp Leu Arg Leu Leu Leu Asn Gly Val
                35              40              45

Asn Asn Tyr Glu Asp Pro Lys Leu Ser Arg Met Leu Thr Phe Lys Phe
    50              55              60

Tyr Thr Pro Lys Lys Ala Thr Glu Leu Thr His Leu Gln Cys Leu Ala
65              70              75              80

Glu Glu Leu Lys Pro Leu Glu Glu Val Leu Tyr Leu Ala Gln Ser Lys
                85              90              95

Asn Phe His Leu Thr Asp Ile Lys Glu Leu Met Ser Asn Ile Asn Val
                100             105             110

Thr Leu Leu Lys Leu Lys Gly Ser Glu Thr Arg Phe Lys Cys Glu Tyr
                115             120             125

Asp Asp Glu Thr Ala Thr Ile Thr Glu Phe Leu Asn Lys Trp Ile Thr
    130             135             140

Phe Cys Gln Ser Ile Phe Ser Thr Leu Thr
145             150
```

<210> SEQ ID NO 39
<211> LENGTH: 143
<212> TYPE: PRT
<213> ORGANISM: Gallus gallus

<400> SEQUENCE: 39

```
Met Met Cys Lys Val Leu Ile Phe Gly Cys Ile Ser Val Ala Met Leu
1               5               10              15

Met Thr Thr Ala Tyr Gly Ala Ser Leu Ser Ser Ala Lys Arg Lys Pro
                20              25              30

Leu Gln Thr Leu Ile Lys Asp Leu Glu Ile Leu Glu Asn Ile Lys Asn
    35              40              45

Lys Ile His Leu Glu Leu Tyr Thr Pro Thr Glu Thr Gln Glu Cys Thr
```

-continued

```
     50                55                60

Gln Gln Thr Leu Gln Cys Tyr Leu Gly Glu Val Val Thr Leu Lys Lys
65                70                75                80

Glu Thr Glu Asp Asp Thr Glu Ile Lys Glu Glu Phe Val Thr Ala Ile
              85                90                95

Gln Asn Ile Glu Lys Asn Leu Lys Ser Leu Thr Gly Leu Asn His Thr
            100               105               110

Gly Ser Glu Cys Lys Ile Cys Glu Ala Asn Asn Lys Lys Lys Phe Pro
         115               120               125

Asp Phe Leu His Glu Leu Thr Asn Phe Val Arg Tyr Leu Gln Lys
    130               135               140
```

INTERLEUKIN-2 VARIANTS WITH MODIFIED BIOLOGICAL ACTIVITY

SEQUENCE LISTING SUBMISSION VIA EFS-WEB

A computer readable text file, entitled "SequenceListing.txt" created on Oct. 10, 2021 with a file size of 52,495 bytes contains the sequence listing for this application and is hereby incorporated by reference in its entirety.

FIELD OF THE INVENTION

The invention relates to Interleukin-2 (IL-2) variants for the prevention or treatment of immune disorders, such as with no limitations, acute or chronic inflammatory, allergic, autoimmune or infectious diseases, graft-versus-host disease, graft-rejection, and cancer. The invention also relates to the use of said IL-2 variants for the screening of anti-IL-2 antibodies with pro-T-effector cell or pro-T-regulatory cell activity.

BACKGROUND OF THE INVENTION

Interleukin-2 (IL-2) is a key cytokine of the immune response which promotes the activation, proliferation and survival of T and B lymphocytes (T and B cells). IL-2 receptor (IL-2R) is a heterotrimeric protein complex composed of an alpha (IL-2-RA or CD25), a beta (IL-2RB or CD122) and a gamma (IL-2RG or Gamma c or CD132) chain. The alpha chain binds IL-2 with low affinity and does not participate in signaling. The combination of the beta and gamma chains forms an intermediate affinity receptor expressed on the effector T cells (conventional T cells (Tconv; CD4+Foxp3−), CD8+ and NK cells responsible for the cell-mediated immune responses; and all three receptor chains form a high affinity receptor expressed constitutively on regulatory T cells (T-regulatory cells or Tregs; CD4+ Foxp3+) which have immunosuppressive function, and shortly or transiently by activated effector T cells and NK cells.

Indeed, IL-2 is a cytokine with both immune stimulating and suppressive function. Consequently, it has been used in the clinic at high doses to stimulate the immune response against cancer, and more recently at low doses to block the immune response in various physiopathological conditions including autoimmune diseases such as type 1 diabetes (T1D), autoimmune vasculitis, inflammatory diseases such as Parkinson disease and parasitic infection such as *Trypanosoma cruzi* infection; and graft rejection including graft-versus-host disease (GVHD) (Rosenberg et al., Sci. Transl. Med., 2012, 4, 127-; Grinberg-Bleyer, Y. et al., J. Exp. Med., 2010, 207, 1871-1878; Tang et al., Immunity, 2008, 28, 687-697; Pilon et al., Am. J. Transplant., 2014, 14, 2874-2882; Saadoun et al., N. Engl. J. Med., 2011, 365, 2067-2077; Koreth et al., N. Engl. J. Med., 2011, 365, 2055-2066; Kennedy-Nasser et al., Clin. Cancer Res. Off. J. Am. Assoc. Cancer Res., 2014, 20, 2215-2225; Baeyens et al., Diabetes, 2013, 62, 3120-3131; Gonzalez et al., Brain. Behay. Immun., 2015, 45, 219-232; Pérol et al., Immunol. Lett., 2014, 162, 173-184).

However, high-doses of IL-2 in cancer therapy can be very toxic and its efficacy is not optimal (5-20% of responders) due to the unwanted effect of IL-2 on Tregs.

In humans, low doses of IL-2 have been successfully administered to boost Tregs and dampen inflammation in autoimmune vasculitis patients and in graft-versus-host disease (Saadoun et al.; Koreth, J. et al.; Kennedy-Nasser et al.). However, improvements need to be done as IL-2 has a very short half-life and needs repeated administration.

Interestingly, when IL-2 is complexed with an anti-IL-2 antibody (Ab), IL-2 pharmacodynamics is improved, its toxicity is lowered, and depending on the Ab, this complex can re-direct IL-2 action to effector (pro-Teff anti-IL-2 Ab) or to regulatory (pro-Treg anti-IL-2 Ab) immune cells, solving the main problems associated with IL-2-based therapies (Boyman et al., Science, 2006, 311, 1924-1927. Letourneau et al., Proc. Natl. Acad. Sci., 2010, 107, 2171-2176). Concerning the mechanism of action, it was shown that the formation of a complex with pro-Teff anti-IL-2 antibody blocks directly the interaction of IL-2 with CD25 (Levin et al., Nature, 2012, 484, 529-533; Rojas, G. in Monoclonal Antibodies (eds. Ossipow, V. & Fischer, N.) 1131, 447-476 (Humana Press, 2014)).

Treg-directed IL-2/anti-IL-2 complexes gave impressive results in different mouse models of inflammation: T1D, asthma, EAE, atherosclerosis, chronic nephropathy and transplantation, including solid organ transplantation (Webster et al., J. Exp. Med., 2009, 206, 751-760; Dinh, T. N. et al., Circulation, 2012, 126, 1256-1266; Polhill, T. et al. J. Am. Soc. Nephrol. JASN, 2012, 23, 1303-1308; Satake et al., PLoS ONE, 2014, 9, e92888; Vokaer et al., Transplant. Proc., 2012, 44, 2840-2844; Goldstein et al., Front. Immunol., 2013, 4, 155).

Another strategy to fine-tune IL-2 biological activity consists in performing punctual mutations in the IL-2 molecule to generate an IL-2 variant or mutant IL-2. A mutant IL-2 protein (IL-2 superkine) comprising five punctual mutations which confer a 300-fold higher affinity for CD122 compared to wild type IL-2 has been disclosed (Levin et al., Nature, 2012, 484, 529-533). Immunosuppressive IL-2 variants with greater affinity for IL-2RA (CD25) and/or altered signaling through IL-2RBG have also been disclosed (WO 2010/085495 and US 2014/0286898).

To improve IL-2 based immunotherapy, there is a need for IL-2 variants for the prevention or treatment of immune disorders.

SUMMARY OF THE INVENTION

The inventors have engineered resurfaced variants of human IL-2 and identified IL-2 variants which are capable of preferentially stimulating T-regulatory (Treg) cells or antagonizing IL-2.

Figure 10:
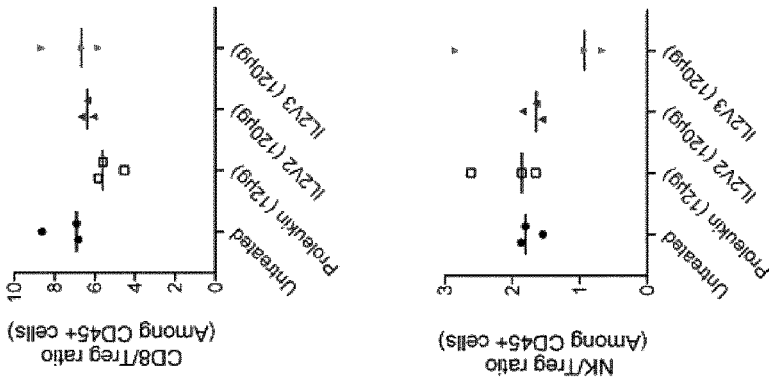
Figure 10:
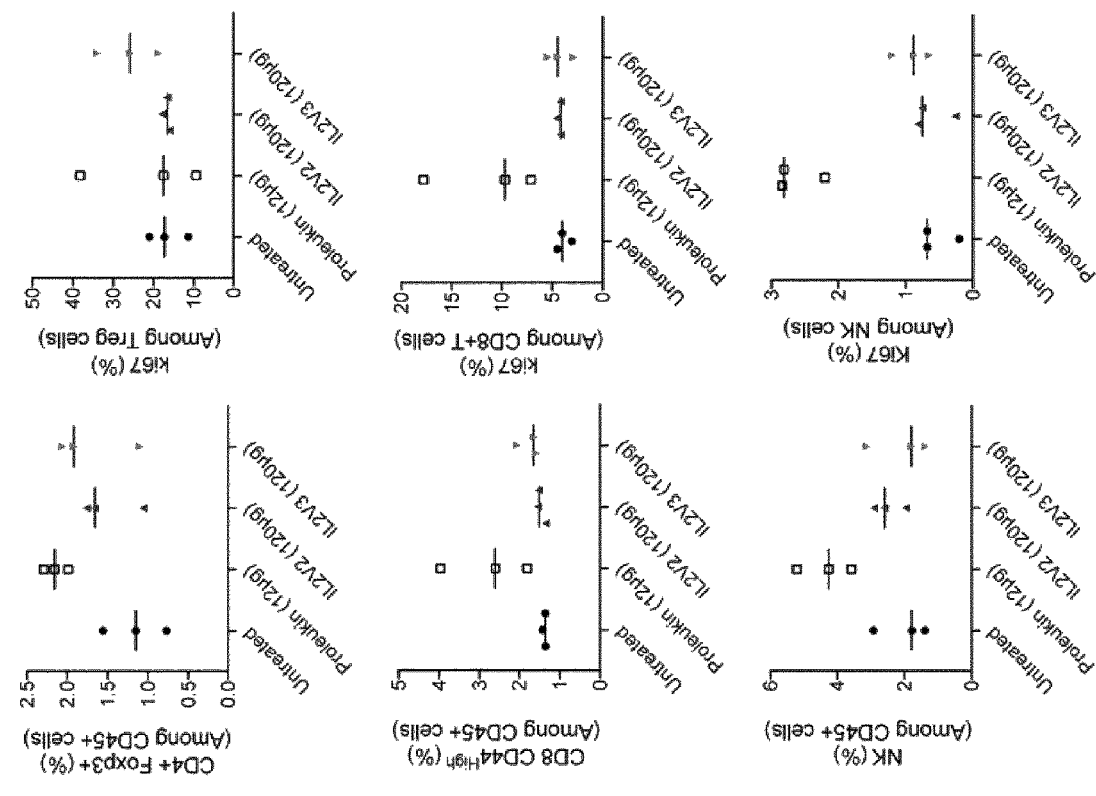

The examples of the present application show resurfaced variants of human IL-2 (Treg-agonist variants) which preferentially stimulate Tregs in vitro (FIG. 6) and increase circulating Treg cells in mice in vivo (FIG. 10). The Treg-agonist variants are useful for reducing immune activation indirectly, by preferentially activating Tregs that in turn inhibit the immune effector cells. The Treg-agonist variants of the invention are thus useful for treating diseases where immunomodulation or immunosuppression is beneficial such as with no limitations, allergic and autoimmune diseases, and diseases comprising overactivity of the immune system including in particular, chronic or acute inflammatory diseases, graft-versus-host disease (GVHD) and graft rejection.

Figure 9:
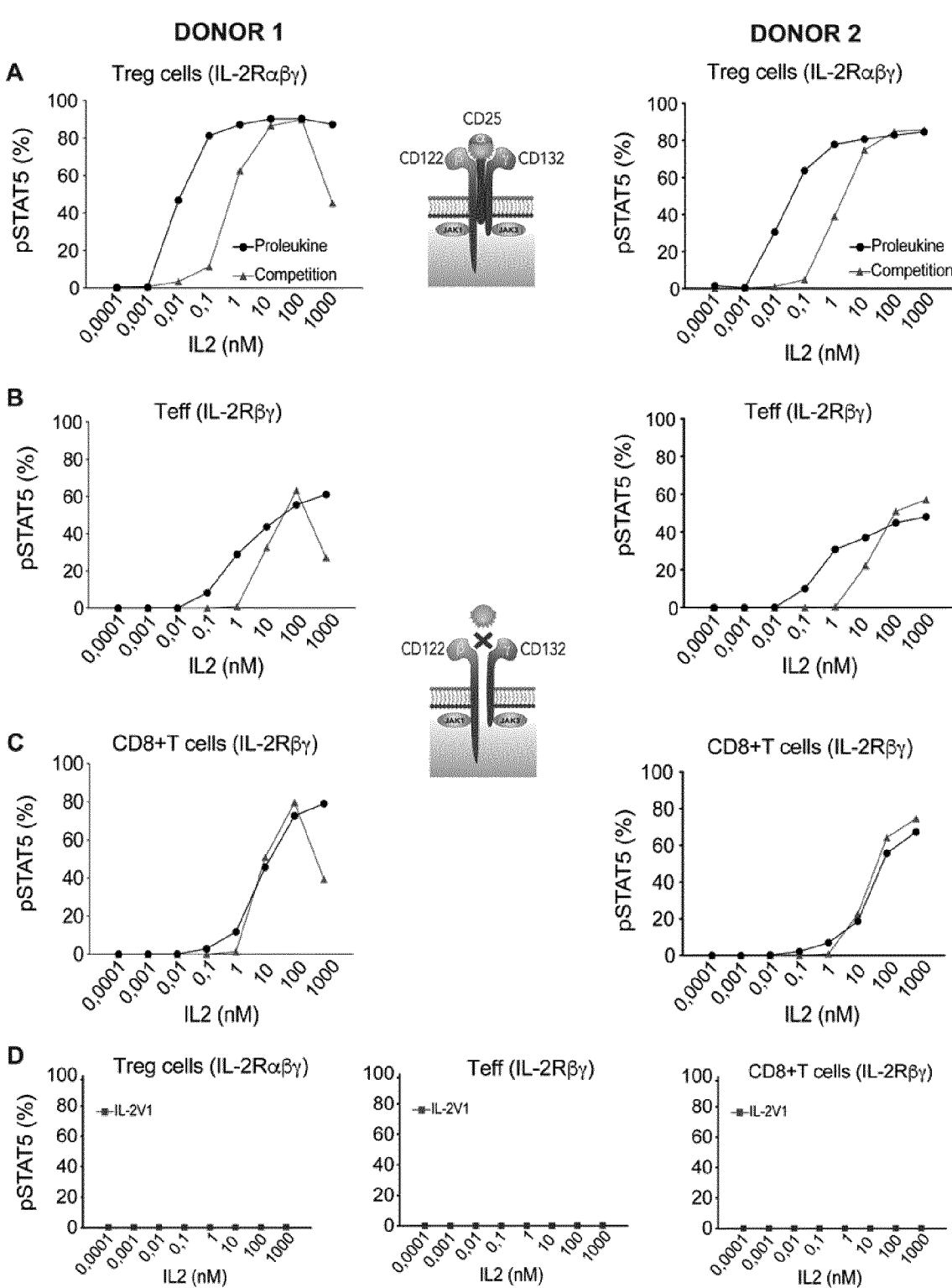

The examples of the present application also show that some of the resurfaced variants of human IL-2 are IL-2 antagonists (FIG. 9).

In the context of diseases comprising overactivity of the immune system associated with overproduction of IL-2 including in particular chronic or acute inflammatory diseases, graft-versus-host disease (GVHD) and graft rejection, the IL-2-antagonist variants according to the invention reduce immune activation directly by competing with endogenous IL-2 and thereby blocks IL-2-mediated overactivation of the immune system.

Figure 7:
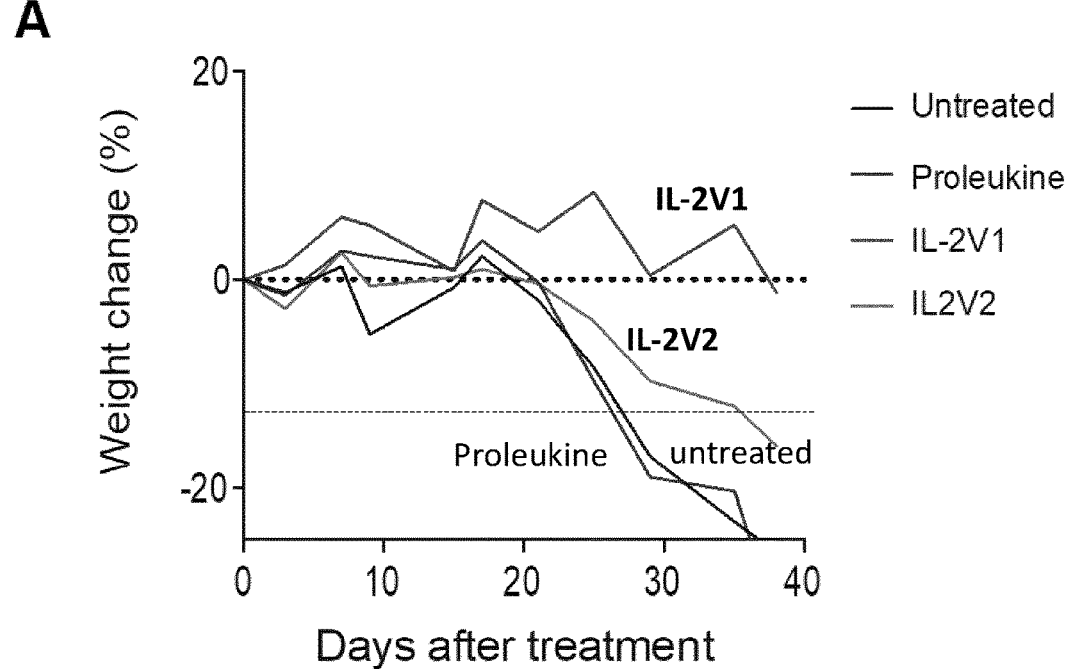
Figure 7:
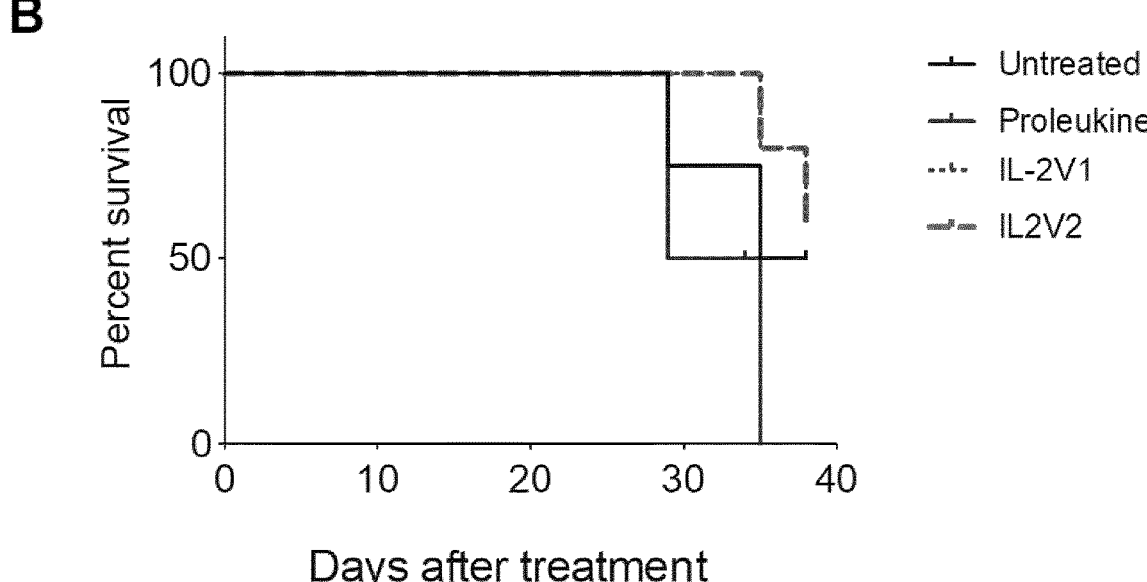

In a murine model of acute GVHD, the IL-2 variants of the invention, whether Treg agonists or IL-2 antagonists, can control GVHD and delay clinical GVHD development. The tested IL-2-antagonist variant was more effective in stopping weight loss and preferentially increasing circulating human Treg cells than the tested Treg-agonist variant (FIG. 7 and FIG. 8).

Furthermore, IL-2 variants that are IL-2 antagonists inhibit Treg division in vitro by depriving them from wild-type IL-2 signaling (similar to a blocking anti-IL-2 antibody; FIG. 12). In vivo, it is expected that inhibition of Tregs with the IL-2 antagonist variants of the invention will reduce tumor growth as previously shown with other IL-2 antagonists (Carmenate et al., The Journal of Immunology, 2018, 200, 3475-3484). Treg inhibition by the IL-2 antagonist variants according to the invention will consequently promote immune responses (lymphocytes (B, NK, CD4+ or CD8+ T cells); dendritic cells (DC); macrophages and others) by unleashing immune cells from Treg suppression. In addition, CD8+ T cell function is preserved or moderately impacted, depending on the used dose of IL-2 antagonist variant (FIG. 9; FIG. 12). Therefore, the IL-2 antagonist variants further allow the direct stimulation of a CD8+ T cell immune response, for example against a tumor, a pathogen or a vaccine. For all these reasons, better immune responses to cancer, infectious agents and vaccines are expected with the IL-2-antagonist variants of the invention.

Altogether the results presented in the application suggest that the effect of the IL-2 antagonist variant in vivo may vary depending on the immune context since it reduces immune activation (by neutralizing excess endogenous IL-2) when the immune system is overactive and produces excess IL-2 while it increases immune activation (by Treg inhibition and CD8+ T cells activation) in different immune contexts. For these reasons, the IL-2 antagonist variants are useful for treating diseases comprising overactivity of the immune system associated with overproduction of IL-2 such as with no limitations, chronic or acute inflammatory diseases, graft-versus-host disease (GVHD) and graft rejection, and also for treating cancer and infectious diseases and increasing immune responses to vaccines.

The inventors have also solved the crystal structure of some of the variants which gave some insight on their mechanism of action. The inventors have observed that the Y31P substitution (IL2-V4) stabilizes the IL-2 in a conformation similar to the one observed in the complex with IL2-R alpha subunit, hereafter the "alpha induced conformation". Indeed, there is some recent evidence from the murine IL-2 suggesting that conformational changes in the loop AB, where the Tyr31 is located, impact allosterically the interaction with the IL-2R beta and gamma subunits (De Paula et al., P.N.A.S., doi/10.1073; Mar. 17, 2020 and Spangler et al., Immunity, 2015, 42, 815-825). Therefore, it is tempting to speculate that the molecular mechanism underlying the IL2-V4 activity takes advantage of this allosteric circuit. Indeed, the inventors have also obtained the structure of the IL2-V1, with the same activity of IL2-V4. In spite none of the mutations present in this variant are located in the AB loop, it also displays the same "alpha induced conformation".

Without being bound by theory, the inventors believe that the substitutions which have been introduced in the IL-2 antagonist variants of the invention stabilize the bound form and induce conformational changes which impact allosterically the interaction with the IL-2R beta and gamma subunits.

These results show the potential of these human IL-2 variants for the treatment of immune disorders and for increasing immune responses against vaccines. Immune disorders include in particular inflammatory, allergic, infectious and autoimmune diseases, graft-versus-host disease (GVHD), graft rejection, and cancer. Vaccines may be directed to cancer or infectious diseases.

The inventors have also shown that the resurfaced variants of IL-2 can also be used to screen for anti-IL-2 antibodies with pro-Teff or pro-Treg activity.

Therefore, the invention relates to an interleukin-2 (IL-2) variant capable of preferentially stimulating T-regulatory cells or antagonizing IL-2, which comprises at least one amino acid substitution at a surface position of IL-2 outside the region contacting the α receptor.

In some embodiments, the interleukin-2 variant according to the invention comprises at least one amino acid substitution at a position selected from the group consisting of: 9, 12, 16, 19, 23, 26, 31, 87, 91 and 95, wherein:

the amino acids at positions 9 and 12 are substituted by D or E; preferably E;

the amino acids at positions 16, 19, 26, 91 and 95 are substituted by K or R; preferably the amino acids at positions 16 and 19 are substituted by R, and the amino acid at positions 26, 91 and 95 are substituted by K;

the amino acid at position 23 is substituted by E, Q, T, N, G, A, V, L or I; preferably L;

the amino acid at position 31 is substituted by P or N, preferably P;

the amino acid at position 87 is substituted by M, V, E, D, T, C, N or Q; preferably N; and wherein when said substitution is at position 91, then said variant comprises at least another substitution at position 9, 12, 16, 19, 23, 26, 31, 49, 52, 81, 84, 87, 95, 119, 123, 127, 131 or 132, and the indicated positions being determined by alignment with SEQ ID NO: 1.

In some preferred embodiments, the variant according to the invention comprises one or more amino acid substitutions at position(s) selected from the group consisting of: 9, 12, 16, 19, 23, 26, 87, 91 and 95, and preferably comprises at least one additional substitution at a position selected from the group consisting of: 31, 49, 52, 81, 84, 119, 123, 127, 131 and 132, wherein:

the amino acid at position 31 is substituted by P or N, preferably P and, the amino acids at position 49, 52, 84 and 132 are substituted by another amino acid chosen from M, V, E, D, S, T, C, N and Q; preferably the amino acid at position 49 is substituted by Q; the amino acids at positions 52 and 132 are substituted by S; and the amino acid at position 84 is substituted by N;

the amino acid at positions 81 is substituted by D or E; preferably E;

the amino acids at positions 119, 127 and 131 are substituted by K or R; preferably the amino acid at position 127 is substituted by K and the amino acid at position 131 is substituted by R; and the amino acid at position 123 is substituted by E, Q, N, M, G, A, V, L or I; more preferably A.

In some other preferred embodiments, the variant according to the invention comprises one substitution at position 31 and does not comprise any substitution at positions 9, 12, 16, 19, 23, 26, 49, 52, 81, 84, 87, 91, 95, 119, 123, 127, 131 and 132.

In some embodiments, the variant according to the invention is a human IL-2 variant, preferably selected from the group consisting of:

a variant comprising the substitutions K9E, L12E, H16R, L19R, M23L, N26K, S87N, V91K, E95K, N119K, T123A, and S127K;

a variant comprising the substitutions K9E, L12E, H16R, L19R, M23L, N26K, S87N, V91K, E95K, Y31P, K49Q, E52S, R81E, D84N, N119K, T123A, T131R and L132S;

a variant comprising the substitution Y31P, wherein the variant does not comprise any substitution at positions 9, 12, 16, 19, 23, 26, 49, 52, 81, 84, 87, 91, 95, 119, 123, 127, 131 and 132;

a variant comprising the substitutions K9E, L12E, H16R, L19R, M23L, N26K, S87N, V91K, E95K, Y31P, K49Q, E52S, R81E, D84N, T131R and L132S;

a variant comprising the substitutions K9E, L12E, H16R, L19R, M23L, N26K, S87N, V91K, E95K, Y31P, N119K, T123A, and S127K; and a variant comprising the substitutions K9E, L12E, H16R, L19R, M23L, N26K, S87N, V91K, E95K, K49Q, E52S, R81E, D84N, N119K, T123A, T131R and L132S.

In some embodiments, the variant according to the invention has at least 70% amino acid identity with any one of SEQ ID NO: 1 and 3 to 8, and preferably which does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133.

In some embodiments, the variant according to the invention preferentially stimulates T regulatory cells.

In some other embodiments, the variant according to the invention is an IL-2 antagonist, preferably wherein the IL-2 antagonist inhibits T regulatory cells and consequently stimulate immune responses, in particular CD8+ T-cell responses.

In some embodiments, the variant according to the invention is associated with an agent of interest, such as in the form of a molecular complex, a particle; a conjugate or a fusion protein. In some preferred embodiments, the IL-2 variant is complexed with an anti-IL-2 antibody, preferably an anti-IL-2 antibody with Pro-T-regulatory cell or Pro-T-effector cell activity. In some preferred embodiments, the IL-2 variant is fused to an antibody against a surface molecule specific for Tregs or a functional fragment thereof comprising at least the antigen binding site. The antibody against the surface molecule specific for Tregs is preferably selected from the group comprising anti-CTLA-4, anti-CD25, anti-CCR8, anti-ICOS, anti-IKZF2, anti-CD70, anti-GARP, anti-IL1R1, anti-CD39, anti-CCR4 and anti-CD177 antibody.

The invention relates to a polynucleotide encoding said variant in expressible form, a vector comprising the polynucleotide, preferably an expression vector, and a host cell comprising the polynucleotide or vector.

The invention relates to a pharmaceutical composition comprising, as active substance, an IL-2 variant, eventually associated with an agent of interest as disclosed in the invention, a polynucleotide, vector, and/or cell according to the invention, and at least one pharmaceutically acceptable vehicle and/or carrier.

The invention relates to the use of the IL-2 variant, polynucleotide, vector, and/or cell according to the invention for treating immune disorders.

In some embodiments, the IL-2 variant which preferentially stimulates Tregs (Treg-agonist variant), polynucleotide, vector, and/or cell according to the invention is used to expand Tregs ex vivo or in vivo for treating diseases where immunomodulation or immunosuppression is beneficial such as with no limitations, allergic and autoimmune diseases, and diseases comprising overactivity of the immune system, including in particular chronic or acute inflammatory diseases, graft-versus-host disease (GVHD), and graft rejection.

In some embodiments the IL-2-antagonist variant, polynucleotide, vector, and/or cell according to the invention is used to block IL-2-mediated overactivation of the immune system for treating diseases comprising overactivity of the immune system associated with overproduction of IL-2, in particular chronic or acute inflammatory diseases, graft-versus-host disease (GVHD) and graft rejection.

In some embodiments the IL-2-antagonist variant, polynucleotide, vector, and/or cell according to the invention is used to inhibit Tregs and, consequently, stimulate immune responses including B, NK, CD4+ or CD8+ T cells, DC, macrophages and others, in particular CD8+ T-cell immune response, for treating cancer or infectious diseases or increasing the immune response against vaccines, in particular vaccines for cancer or infectious diseases.

In some embodiments the IL-2-antagonist variant, polynucleotide, vector, and/or cell according to the invention is used in combination with Chimeric Antigen Receptor T-cell therapy, immunomodulatory monoclonal antibody therapy, or therapy with anticancer or anti-infectious agents including therapeutic agents and vaccines against cancer and infectious diseases. In some preferred embodiments the IL-2-antagonist variant, polynucleotide, vector, and/or cell according to the invention is used in combination with at least an additional cancer therapy selected from the group comprising: targeted therapy, immunotherapy such as immune checkpoint therapy and immune checkpoint inhibitor, co-stimulatory antibodies, chemotherapy and/or radiotherapy.

The invention relates also to the use of the IL-2 variant according to the invention for the screening of anti-IL-2 antibodies with pro-T-effector cell or pro-T-regulatory cell activity.

DETAILED DESCRIPTION OF THE INVENTION

IL-2 Variant

The invention relates to an interleukin-2 (IL-2) variant capable of preferentially stimulating T-regulatory cells or antagonizing IL-2, which comprises at least one amino acid substitution at a surface position of IL-2 outside the region contacting the α receptor.

The term interleukin-2 or IL-2, also known as TCGF or lymphokine, refers to a protein encoded by the IL-2 gene in a mammalian genome. IL-2 is expressed as a precursor containing a N-terminal signal peptide (20 amino acids) which is cleaved to yield the mature protein (IL-2). Representative examples of IL-2 are shown in FIG. 1 and include without limitation, human (Gene ID: 3558), rat (Gene ID: 116562), cat (Gene ID: 751114), and mouse (Gene ID 16183) forms. As used herein, IL-2, refers to wild-type IL-2. Human IL-2 precursor has the 153 amino acid sequence UniProtKB/Swiss-Prot: P60568.1. Mature IL-2 has the 133 amino acid sequence from positions 21 to 153 of the precursor and corresponds to SEQ ID NO: 1.

In the following description, the residues are designated by the standard one letter amino acid code and the indicated positions are determined by alignment with SEQ ID NO: 1. For example, K9 is the lysine residue at position 9 of SEQ ID NO: 1. Substitutions are designated herein by the one letter amino acid code followed by the substituting residue in one letter amino acid code; K9E is a substitution of the lysine (K) residue at position 9 of SEQ ID NO: 1 with a Glutamic acid (E) residue.

"a", "an", and "the" include plural referents, unless the context clearly indicates otherwise. As such, the term "a" (or "an"), "one or more" or "at least one" can be used interchangeably herein; unless specified otherwise, "or" means "and/or".

The invention provides interleukin-2 (IL-2) variants capable of preferentially stimulating T-regulatory cells (Tregs) or antagonizing IL-2 that are useful for the treatment of immune disorders.

As used herein "immune disorders" refer to diseases involving an immune dysfunction or immune dysregulation. Immune dysfunction may comprise inhibition, dysfunction or overactivity of the immune system. Immune disorders include diseases that can be prevented or treated by immunomodulation using immunomodulatory, immunosuppressive, and/or immunostimulatory agents. Immunomodulation may comprise preferentially stimulating Tregs or inhibiting Tregs. Immunosuppression may comprise preferentially stimulating Tregs which in turn inhibit the immune effector cells or inhibiting immune effector cells directly. Likewise, immunostimulation may comprise inhibiting Tregs which in turn unleash immune cells from immunosuppression or stimulating effector immune cells directly. Immunomodulatory agents which inhibit Tregs and immunostimulatory agents are useful for preventing or treating diseases where inhibition of Tregs and/or stimulation of immune responses is beneficial such as with no limitations, infectious diseases and cancer, including the treatment of infectious diseases and cancer and the increase of immune response against vaccines. Vaccines are in particular vaccines directed to cancer or infectious diseases. Immunomodulatory agents which stimulate Tregs and immunosuppressive agents are useful for treating diseases involving an immune dysfunction such as with no limitations allergic and autoimmune diseases and diseases associated with overactivity of the immune system, such as with no limitations, chronic or acute inflammatory diseases, graft-versus-host disease (GVHD) including acute GVHD and graft rejection.

The IL-2 variants according to the invention which preferentially stimulate T-regulatory cells (Treg-agonist variants) are useful for expanding Tregs ex vivo or in vivo. The IL-2 variants according to the invention which antagonize IL-2 (IL-2-antagonist variants) are useful for blocking IL-2-mediated overactivation of the immune system, or for inhibiting Tregs by depriving them from IL-2 signaling and consequently, stimulating immune responses including B, NK, CD4+ or CD8+ T cells, DC, macrophages and others, in particular CD8+ T cell immune response in vivo, such as anti-tumoral immune responses or immune responses against vaccines or pathogens. As used herein "preferentially stimulate T-regulatory cells" means that the IL-2 variant promotes the proliferation or activation of T-regulatory cells over non-regulatory T cells. As used herein "T-regulatory cells", "Treg" or "Tregs" refer to CD3+CD4+ Foxp3+ T cells including CD3+CD4+Foxp3+CD25+ and CD3+CD4+Foxp3+CD25− cells. As used herein, "T-effector cells", "Teff" or "Teffs" refer to one or more of Tconv cells (CD3+CD4+Foxp3−); CD8+ T cells (CD3+CD8+) and NK cells (CD3−CD16+). As used herein "inhibit Tregs" means that the IL-2 variant is capable of inhibiting the proliferation, the activation, or the suppressive function of Tregs cells by depriving them from IL-2 signaling. The inhibition of Tregs include the inhibition of Treg function or loss of Treg function, in particular Treg immunosuppressive function and the elimination of Tregs. The ability of the IL-2 variant of the invention to preferentially stimulate T-regulatory cells can be measured by standard assays that are well-known in the art and disclosed in the examples of the present application, including with no limitation STAT5 phosphorylation assay or flow cytometry analysis on a population of T cells from a subject treated in vivo or a peripheral blood sample treated in vitro. The ability of IL-2 variant to antagonize IL-2 can be determined by standard assays that are well-known in the art and disclosed in the examples of the present application, such as STAT5 phosphorylation assay in competition with Proleukine on a peripheral blood sample treated in vitro or quantification of proliferation using a CellTrace Violet (CTV) dilution assay.

The Treg-agonist variants are useful for reducing immune activation indirectly, by preferentially activating Tregs that in turn inhibit the immune effector cells. The Treg-agonist variants of the invention are thus useful for treating diseases where immunomodulation or immunosuppression is beneficial such as with no limitations, allergic and autoimmune diseases, and diseases comprising overactivity of the immune system including with no limitations chronic or acute inflammatory diseases, graft-versus-host disease (GVHD) and graft rejection.

The IL-2 variants according to the invention which are IL-2 antagonist are useful for inhibiting Tregs and consequently stimulating immune responses (B, NK, CD4+ or CD8+ T cells, DC, macrophages and others). The IL-2-antagonist variants according to the invention are useful for stimulating anti-tumoral immune response(s) or immune response(s) against a pathogen or a vaccine including a vaccine against cancer or infectious disease, in particular anti-tumoral CD8+ T-cell response and anti-CD8+ T-cell response against a pathogen or vaccine. In addition, since the results of the application suggest that the effect of the IL-2 antagonist in vivo may vary depending on the immune context, the IL-2 antagonist is also useful for reducing immune activation by blocking excess IL-2 present in the patient in the context of diseases comprising overactivity of the immune system associated with overproduction of IL-2, such as with no limitations, chronic or acute inflammatory diseases, graft-versus-host disease (GVHD) and graft rejection.

The invention provides an interleukin-2 (IL-2) variant, which comprises at least one amino acid substitution at a surface position of IL-2 outside the region contacting the α receptor. Residues contacting the α receptor are defined as those residues of IL-2 with at least one atom at a distance of 8 Å or less from any atom of the α receptor. Surface residues are defined as those with >50% side-chain surface area exposed, as determined according standard methods that are well-known in the art (Fraczkiewicz et al., J. Comp. Chem, 1998. 19, 319-333).

In some embodiments, the IL-2 variant comprises at least one amino acid substitution at a position selected from the group consisting of: 9, 12, 16, 19, 23, 26, 31, 87, 91 and 95, the indicated positions being determined by alignment with SEQ ID NO: 1.

By "comprises at least one substitution", it is meant that the IL-2 variant has one or more amino acid substitutions as indicated with respect to the amino acid sequence SEQ ID NO: 1, but may have other modifications, including with no limitation substitutions, deletions or additions of amino acid residues. The IL-2 variant can comprise 1, 2, 3, 4, 5, 6, 7, 8, 9 or all of the substitutions listed above. All of these possible combinations are specifically contemplated.

In some embodiments, the IL-2 variant comprises one or more amino acid substitutions at position(s) selected from the group consisting of: 9, 12, 16, 19, 23, 26, 87, 91 and 95. The IL-2 variant can comprise 1, 2, 3, 4, 5, 6, 7, 8 or all of the substitutions listed above. All of these possible combinations are specifically contemplated.

In some preferred embodiments, the IL-2 variant comprises at least one additional substitution at a position selected from the group consisting of: 31, 49, 52, 81, 84, 119, 123, 127, 131 and 132, the indicated positions being determined by alignment with SEQ ID NO: 1. The IL-2 variant can comprise 1, 2, 3, 4, 5, 6, 7, 8, 9 or all of the additional substitutions listed above. All of these possible combinations are specifically contemplated.

In some more preferred embodiments, said variant comprises additional substitutions at positions 119, 123 and 127; 31, 119, 123 and 127; 31, 49, 52, 81, 84, 119, 123, 131 and 132; 31, 49, 52, 81, 84, 131 and 132; or 49, 52, 81, 84, 119, 123, 131 and 132.

In some preferred embodiments, when said substitution is at position 91, then said variant comprises at least another substitution at position 9, 12, 16, 19, 23, 26, 31, 49, 52, 81, 84, 87, 95, 119, 123, 127, 131 or 132. The IL-2 variant can comprise 1, 2, 3, 4, 5, 6, 7, 8, 9, 10, 11, 12, 13, 14, 15, 16, 17, 18 or all of the additional substitutions listed above. All of these possible combinations are specifically contemplated. Preferably, the variant comprises substitutions at positions 9, 12, 16, 19, 23, 26, 87, 91 and 95, and eventually also at least one additional substitution at a position selected from the group consisting of: 31, 49, 52, 81, 84, 119, 123, 127, 131 and 132. The IL-2 variant can comprise 1, 2, 3, 4, 5, 6, 7, 8, 9 or all of the additional substitutions listed above. All of these possible combinations are specifically contemplated. In some more preferred embodiments, the IL-2 variant comprises additional substitutions at positions 119, 123 and 127; 31, 119, 123 and 127; 31, 49, 52, 81, 84, 119, 123, 131 and 132; 31, 49, 52, 81, 84, 131 and 132; or 49, 52, 81, 84, 119, 123, 131 and 132.

In some other embodiments, the IL-2 variant comprises one substitution at position 31; the IL-2 variant comprises only one of said substitutions, which means that the IL-2 variant does not comprise any substitution at the other indicated positions (9, 12, 16, 19, 23, 26, 87, 91, 95 and 49, 52, 81, 84, 119, 123, 127, 131 and 132).

In some preferred embodiments, the amino acids at positions 9, 12 and 81 are substituted by D or E; preferably E.

In some preferred embodiments, the amino acids at positions 16, 19, 26, 91, 95, 119, 127 and 131 are substituted by K or R; preferably the amino acids at positions 16, 19 and 131 are substituted by R, and the amino acid at positions 26, 91, 95 and 127 are substituted by K.

In some preferred embodiments, the amino acid at positions 23 and 123 are substituted by another amino acid chosen from E, Q, T, N, G, A, V, L, I and M; more preferably the amino acid at position 23 is substituted by L and the amino acid at position 123 is substituted by A.

In some preferred embodiments, the amino acid at position 31 is substituted by N or P; preferably P.

In some preferred embodiments, the amino acid at positions 49, 52, 84, 87 and 132 are substituted by another amino acid chosen from: M, V, E, D, S, T, C, N and Q; preferably the amino acids at positions 87 and 84 are substituted by N; the amino acid at position 49 is substituted by Q and the amino acids at positions 52 and 132 are substituted by S.

The IL-2 variant can comprise 1, 2, 3, 4, 5, 6, 7, 8, 9, 10, 11, 12, 13, 14, 15, 16, 17, 18 or all of the substitutions listed above. All of these possible combinations are specifically contemplated.

In some preferred embodiments, said IL-2 variant comprises at least one or more (i.e., 1, 2, 3, 4, 5, 6, 7, 8 or 9) substitutions chosen from the substitutions K9E or K9D, L12E or L12D, H16R or H16K, L19R or L19K, M23L, N26K or N26R, S87N, V91K or V91R, E95K or E95R; preferably one or more (i.e., 1, 2, 3, 4, 5, 6, 7, 8 or 9) substitutions chosen from K9E, L12E, H16R, L19R, M23L, N26K, S87N, V91K and E95K. Preferably, said IL-2 variant comprises all the above listed substitutions. In some preferred embodiments, the IL-2 variant comprises additional substitutions selected from the group consisting of N119K or N119R, T123A, and S127K or S127R; Y31P, N119K or N119R, T123A, and S127K or S127R; Y31P, K49Q, E52S, R81E or R81D, D84N, N119K or N119R, T123A, T131R or T131K and L132S; Y31P, K49Q, E52S, R81E or R81D, D84N, T131R or T131K and L132S; or K49Q, E52S, R81E or R81D, D84N, N119K or N119R, T123A, T131R or T131K and L132S. Preferably selected from the group consisting of: N119K, T123A, and S127K; Y31P, N119K, T123A, and S127K; Y31P, K49Q, E52S, R81E, D84N, N119K, T123A, T131R and L132S; Y31P, K49Q, E52S, R81E, D84N, T131R and L132S; or K49Q, E52S, R81E, D84N, N119K, T123A, T131R and L132S.

In some preferred embodiments, said IL-2 variant is a human IL-2 variant.

According to said preferred embodiments, said IL-2 variant, preferably a human IL-2 variant, comprises:
  a) the substitutions K9E or K9D, L12E or L12D, H16R or H16K, L19R or L19K, M23L, N26K or N26R, S87N, V91K or V91R, E95K or E95R; preferably the substitutions K9E, L12E, H16R, L19R, M23L, N26K, S87N, V91K and E95K; and additional substitutions selected from the group consisting of:
  $a_1$) N119K or N119R, T123A, and S127K or S127R; preferably N119K, T123A, and S127K;
  $a_2$) Y31P, N119K or N119R, T123A, and S127K or S127R; preferably Y31P, N119K, T123A, and S127K;
  $a_3$) Y31P, K49Q, E52S, R81E or R81D, D84N, N119K or N119R, T123A, T131R or T131K and L132S; preferably Y31P, K49Q, E52S, R81E, D84N, N119K, T123A, T131R and L132S;
  $a_4$) K49Q, E52S, R81E or R81D, D84N, N119K or N119R, T123A, T131R or T131K and L132S; preferably K49Q, E52S, R81E, D84N, N119K, T123A, T131R and L132S; and
  $a_5$) Y31P, K49Q, E52S, R81E or R81D, D84N, T131R or T131K and L132S; preferably Y31P, K49Q, E52S, R81E, D84N, T131R and L132S; or
  b) the substitution Y31P or Y31N; preferably Y31P;
and the indicated positions being determined by alignment with SEQ ID NO: 1.

According to the invention, the IL-2 variants having the substitutions in a) and the additional substitutions in $a_3$) or $a_5$) are capable of preferentially stimulating T-regulatory cells (Treg-agonist variants), whereas the IL-2 variants having the substitutions in a) and the additional substitutions in $a_1$), $a_2$) or $a_4$), and the IL-2 variants having the substitution in b) are capable of antagonizing IL-2 (IL-2 antagonist variants).

In some more preferred embodiments, the human IL-2 variant is selected from the group consisting of:

a variant comprising the substitutions K9E, L12E, H16R, L19R, M23L, N26K, S87N, V91K, E95K, N119K, T123A, and S127K; this variant is named IL2-v1 (IL2V1, IL2-V1, IL-2V1, IL-2-V1 or IL-2 V1) in the examples;

a variant comprising the substitutions K9E, L12E, H16R, L19R, M23L, N26K, S87N, V91K, E95K, Y31P, K49Q, E52S, R81E, D84N, N119K, T123A, T131R and L132S; this variant is named IL2-v2 (IL2V2, IL2-V2, IL-2V2, IL-2-V2 or IL-2 V2) in the examples;

a variant comprising the substitutions K9E, L12E, H16R, L19R, M23L, N26K, S87N, V91K, E95K, Y31P, K49Q, E52S, R81E, D84N, T131R and L132S; this variant is named IL2-v3 (IL2V3, IL2-V3, IL-2V3, IL-2-V3 or IL-2 V3) in the examples;

a variant comprising the substitution Y31P, wherein the variant does not comprise any substitution at the other indicated positions (9, 12, 16, 19, 23, 26, 87, 91, 95 and 49, 52, 81, 84, 119, 123, 127, 131 and 132); this variant is named IL2-v4 (IL2V4, IL2-V4, IL-2V4, IL-2-V4 or IL-2 V4) in the examples;

a variant comprising the substitutions K9E, L12E, H16R, L19R, M23L, N26K, S87N, V91K, E95K, Y31P, N119K, T123A, and S127K; this variant is named IL2-v5 (IL2V5, IL2-V5, IL-2V5, IL-2-V5 or IL-2 V5) in the examples; and a variant comprising the substitutions K9E, L12E, H16R, L19R, M23L, N26K, S87N, V91K, E95K, K49Q, E52S, R81E, D84N, N119K, T123A, T131R and L132S; this variant is named IL2-v6 (IL2V6, IL2-V6, IL-2V6, IL-2-V6 or IL-2 V6) in the examples.

In the various embodiments, the IL-2 variant (Treg-agonist variant or IL-2 antagonist) may comprise at least one additional amino acid mutation (insertion, deletion, substitution) or not. In some embodiments, the IL-2 variant does not comprise additional amino acid mutations. In some other embodiments, the IL-2 variant comprises at least one additional amino acid mutation (insertion, deletion, substitution). The IL-2 variant comprises preferably at least one amino acid deletion, more preferably at a position selected from S4, S5 or S6, the indicated positions being determined by alignment with SEQ ID NO: 1. The IL-2 variant can comprise 1, 2 or all of the deletions listed above in combination with the above listed substitutions. All of these possible combinations are specifically contemplated.

In the various embodiments, the IL-2 variant may be derived from wild-type IL-2 or a wild-type IL-2 construct. In some embodiments, the IL-2 variant is derived from a wild-type human IL-2 construct of SEQ ID NO: 2. In some preferred embodiments, the IL-2 variant comprises or consists of any one of SEQ ID NO: 3 to 8.

The IL-2 variant is at least 125 amino acids in size. Preferably, the IL-2 variant is at least 130 or more amino acids in size.

In some preferred embodiments, the IL-2 variant has at least 70% amino acid identity with SEQ ID NO: 1. Preferably, said IL-2 variant has at least 75%, 80%, 85%, 86%, 87%, 88%, 89%, 90%, 91%, 92%, 93%, 94%, 95%, 96%, 97%, 98% or 99% identity with said sequence. More preferably, said IL-2 variant sequence has at least 85%, 86%, 87%, 88%, 89%, 90%, 91%, 92%, 93%, 94%, 95%, 96%, 97%, 98% or 99% identity with said sequence, even more preferably at least 95%, 96%, 97%, 98% or 99% 98% or 99% identity with said sequence.

The percent amino acid sequence identity is defined as the percent of amino acid residues in a Compared Sequence that are identical to the Reference Sequence after aligning the sequences and introducing gaps if necessary, to achieve the maximum sequence identity and not considering any conservative substitutions as part of the sequence identity. Sequence identity is calculated over the entire length of the Reference Sequence. Alignment for purposes of determining percent amino acid sequence identity can be achieved in various ways known to a person of skill in the art, for instance using publicly available computer software such as BLAST (Altschul et al., J. Mol. Biol., 1990, 215, 403-). When using such software, the default parameters, e.g., for gap penalty and extension penalty, are preferably used. The BLASTP program uses as default a word length (W) of 3 and an expectation (E) of 10.

In some preferred embodiments, the IL-2 variant does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133 or at positions 4, 8, 10, 11, 13, 15, 18, 20, 22, 29, 30, 35, 37, 38, 42, 45, 48, 62, 67, 68, 69, 71, 74, 75, 76, 80, 85, 86, 88, 90, 92, 110, 125, 126, 128, 129, 130 and 133.

In some preferred embodiments, the IL-2 variant is selected from the group consisting of the sequences SEQ ID NO: 3 to 8 and the sequences having at least 70% amino acid identity with said sequences. Preferably, said IL-2 variant has at least 75%, 80%, 85%, 86%, 87%, 88%, 89%, 90%, 91%, 92%, 93%, 94%, 95%, 96%, 97%, 98% or 99% identity with said sequences. More preferably, said IL-2 variant has at least 85%, 86%, 87%, 88%, 89%, 90%, 91%, 92%, 93%, 94%, 95%, 96%, 97%, 98% or 99% identity with said sequences, even more preferably at least 95%, 96%, 97%, 98% or 99% 98% or 99% identity with said sequences; more preferably, said IL-2 variant does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133 or at positions 4, 8, 10, 11, 13, 15, 18, 20, 22, 29, 30, 35, 37, 38, 42, 45, 48, 62, 67, 68, 69, 71, 74, 75, 76, 80, 85, 86, 88, 90, 92, 110, 125, 126, 128, 129, 130 and 133.

In some embodiments, the IL-2 variant is capable of preferentially stimulating T-regulatory cells (Tregs). Non-limiting examples of such variants include the variants IL-2V2 and IL-2V3 as defined above. In some preferred embodiments, said IL-2 variant is selected from the group consisting of the sequences SEQ ID NO: 4 and 5, and the sequences having at least 70% amino acid identity with said sequences, as defined above; more preferably, said IL-2 variant does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133 or at positions 4, 8, 10, 11, 13, 15, 18, 20, 22, 29, 30, 35, 37, 38, 42, 45, 48, 62, 67, 68, 69, 71, 74, 75, 76, 80, 85, 86, 88, 90, 92, 110, 125, 126, 128, 129, 130 and 133. The IL-2 variants capable of preferentially stimulating Tregs (Treg-agonists) of the invention are useful for treating diseases where immunomodulation or immunosuppression is beneficial such as with no limitations, allergic and autoimmune diseases, and diseases comprising overactivity of the immune system including with no limitations chronic or acute inflammatory diseases, graft-versus-host disease (GVHD) and graft rejection.

In some embodiments, the IL-2 variant is an IL-2 antagonist. Non-limiting examples of such variants include the variants IL-2V1, IL-2V4, IL-2V5 and IL-2V6 as defined above, preferably IL-2V1 or IL-2V4; more preferably IL-2V4. In some preferred embodiments, said IL-2 variant is selected from the group consisting of the sequences SEQ ID NO: 3, 6, 7 and 8 and the sequences having at least 70% amino acid identity with said sequences, as defined above; preferably SEQ ID NO: 3 or a sequence having at least 70% amino acid identity with said sequence; more preferably said IL-2 variant does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133 or at positions 4, 8, 10, 11, 13, 15, 18, 20, 22, 29, 30, 35, 37, 38, 42, 45, 48, 62, 67, 68, 69, 71, 74, 75, 76, 80, 85, 86, 88, 90, 92, 110, 125, 126, 128, 129, 130 and 133. The IL-2 antagonist according to the invention may be used either to suppress harmful immune responses in vivo or to stimulate beneficial immune responses in vivo. Therefore, the IL-2 antagonist according to the invention is useful for treating diseases comprising overactivity of the immune system associated with overproduction of IL-2, such as with no limitations, chronic or acute inflammatory diseases, graft-versus-host disease (GVHD) and graft rejection. The IL-2 antagonist is also useful for inhibiting Tregs by depriving Tregs from endogenous wild-type IL-2 signaling and consequently stimulating immune responses (B, NK, CD4+ or CD8+ T cells, DC, macrophages and others), in particular CD8+ T-cell immune response. Therefore, the IL-2 antagonist variant is also useful for preventing or treating immune disorders where Treg inhibition and/or stimulation of immune responses, in particular CD8+ T-cell immune response, is beneficial, such as with no limitations cancer, infectious diseases and vaccination.

The invention encompasses IL-2 variants having one or more modifications into one or more amino acid residues, peptide bonds, N- and/or C-terminal ends, as long as the modified variant is functional (i.e., capable of preferentially stimulating Tregs or antagonizing IL-2). Preferred modifications are those which increase the stability or the bioavailability of the IL-2 variant according to the invention, in particular which increase its half-life in vivo; decrease its immunogenicity; or facilitate its purification, detection or targeting to a specific cell type or tissue. These modifications which are introduced into the variant by the conventional methods known to those skilled in the art, include, in a non-limiting manner: mutation (insertion, deletion, substitution) of one or more amino acids in the amino acid sequence; fusion to an amino acid moiety of interest (protein of interest for a therapeutic use or tag for the purification, the detection (antibody epitope or label) or coupling to a molecule or agent of interest; substitution of a natural amino acid with a non-proteinogenic amino acid (D amino acid or amino acid analog); modification of the peptide bond, in particular with a bond of the retro or retro-inverso type or a bond different from the peptide bond; the cyclization, and the addition of a chemical group to the amino acid side chain or the N- and/or C-terminal end(s) of the variant, in particular for coupling to a molecule or agent of interest to the variant. The modifications include in a non-limiting manner, esterification, glycosylation, acylation such as acetylation or linking myristic acid, amidation, phosphorylation, biotinylation, PEGylation, coupling of farnesyl and similar modifications which are well-known in the art. Modifications can be introduced at the N-terminus (acetylation), the C-terminus (amidation) of the IL-2 variant or if deemed suitable, also to any amino acid other than the terminal amino acids (e.g. farnesyl coupling to a cysteine side chain). Conversion of the acid function on the C-terminus into an aldehyde and alkylation of the thiol function of a cysteine residue are used for chemoselective ligation or the formation of reduced peptide bonds.

In particular, the invention encompasses IL-2 variants comprising or consisting of a chain of natural amino acids (20 gene-encoded amino acids (A, R, N, D, C, Q, E, G, H, I, L, K, M, F, P, S, T, W, X and Y) in a L- and/or D-configuration) linked via a peptide bond and furthermore comprises peptidomimetics of such variants where the amino acid(s), peptide bond(s) N- and/or C-terminal ends have been replaced by functional analogues. Such functional analogues of amino acids include all known amino acids other than said 20 gene-encoded amino acids.

In some embodiments the IL-2 variant is provided in a form where it is associated with at least an agent of interest, for example in the form of a complex such as a molecular complex or a particle; a conjugate or a fusion protein. The agent of interest includes with no limitation any therapeutic agent including a cell such as patient's Chimeric Antigen Receptor (CAR) T-cell, any agent that increases the stability or the bioavailability of the IL-2 variant according to the invention, in particular that increases its half-life in vivo; any agent that decreases its immunogenicity; or any agent that facilitates its purification, detection or its targeting to a specific cell type or tissue. The agent of interest can be a small or large chemical compound, a macromolecule or a particle. Particles include with no limitation liposomes, micelles and nanoparticles including liposomes, micelles and nanoparticles carrying an active agent such as nanocarriers. For example, the IL-2 variant, and eventually other agent(s) of interest can be encapsulated into the particles or grafted onto said particles by means well-known in the art. In a preferred embodiment, the agent of interest is selected from the group consisting of: peptides; proteins including antibodies; bioactive substances like drugs for the treatment of human, or animal diseases; labels, tags and particles.

In some more preferred embodiments, the agent of interest is an anti-IL-2 antibody, preferably an anti-IL-2 antibody with pro-Treg or pro-T-effector function or a functional fragment thereof comprising at least the antigen binding site; more preferably a human or humanized anti-IL-2 antibody. Anti-IL-2 antibodies with pro-Treg function or fragment thereof are useful for the treatment of diseases associated with overactivity of the immune system, such as with no limitations, chronic or acute inflammatory diseases, graft-versus-host disease (GVHD) and graft rejection. Anti-IL-2 antibodies with pro-T-effector function or fragment thereof are useful for preventing or treating immune disorders where Treg inhibition and/or stimulation of a CD8+ T-cell response is beneficial such as with no limitations cancer, infectious diseases and vaccination. In some embodiments, the anti-IL-2 antibody, preferably an anti-IL-2 antibody with pro-Treg or pro-T-effector function, is a whole antibody molecule.

In some more preferred embodiments, the agent of interest comprises or consists of a ligand of a surface molecule specific for Tregs. Surface molecules specific for Tregs are known in the art and disclosed for example in Bhairavabhotla et al., Human Immunol., 2016, 77, 201-13; van der Veeken et al., Cold Spring Harb. Symp. Quant Biol., 2013, 78, 215-22; Pfoertner et al., Genome Biol., 2006, 7, R54; Sugimoto et al., Int. Immunol., 2006, 18, 1197-. Non-limiting examples of surface molecules specific for Tregs that can be used in the invention include CD25, CTLA-4, CCR8, ICOS, IKZF2, CD70, GARP, IL1R1, CD39, CCR4, and CD177.

The agent of interest is preferably an antibody against said surface molecule specific for Tregs or a functional fragment thereof comprising at least the antigen binding site; preferably an anti-CTLA-4, anti-CD25, anti-CCR8, anti-ICOS, anti-IKZF2, anti-CD70, anti-GARP, anti-IL1R1, anti-CD39, anti-CCR4 or anti-CD177 antibody; more preferably a human or humanized antibody. In some embodiments, the antibody against the Treg specific surface molecule is a whole antibody molecule, preferably whole human or humanized antibody molecule.

In some more preferred embodiments, the agent of interest is selected from the group comprising: whole antibody or antibody Fc region, preferably whole human antibody or human Fc region; multi-specific antigen binding protein such as bispecific antibody; Ankyrin and Designed Ankyrin Repeat Protein (DARPin); MHC-peptide multimer such as class I or class II MHC-peptide tetramer, in particular MHC-peptide multimer. The peptide in the MHC-peptide multimer may be derived from an antigen capable of inducing auto-immune or allo-immune response(s) such as a self-antigen or from a foreign antigen such as an antigen from a pathogen or a tumor, in particular a vaccine antigen against a pathogen or a tumor.

It is within the present invention that the complex, conjugate or fusion protein comprises more than one IL-2 variant according to the present invention, i.e., a plurality of such variants, whereby the plurality of the variants may comprise a plurality of the same or of different variants. Also, the complex, conjugate or fusion protein according to the present invention may also comprise more than one agent of interest, whereby the plurality of the agents may comprise a plurality of the same or of different agents.

The agent of interest is covalently or non-covalently linked to the IL-2 variant of the invention. The agent of interest may be coupled to the IL-2 variant, directly or indirectly. Indirect coupling of the agent of interest to the IL-2 variant may be through a linker that is attached to the IL-2 variant of the invention. Linkers, also named spacers, that can be used to physically separate the IL-2 variant of the invention to the agent of interest agent are known in the art and include a peptide bond, an amino acid, a peptide of appropriate length or a different molecule providing the desired feature. The linker may be attached to the N-terminus, the C-terminus of the IL-2 variant or if deemed suitable, also to any amino acid other than the terminal amino acids. The IL-2 variant of the invention can be chemically linked to the agent of interest by covalent bonds using standard conjugation techniques. The agent of interest can be linked to the N-terminus, the C-terminus of the IL-2 variant, or if applicable, to any amino acid other than the terminal amino acids. Functional groups, modifications also called derivatizations or a linker may also be introduced into the IL-2 variant for conjugating the IL-2 variant to the agent of interest. Such covalent bonds are preferably formed between, either a suitable reactive group of the IL-2 variant and the agent of interest, and more preferably between a terminus of the IL-2 variant according to the present invention and the agent of interest. Depending on the chemical nature of the agent of interest, the moiety, group or radical with which such covalent bond is formed varies and it is within the skills of a person of the art to create such bond. Chemical linkage may be via a disulphide bond, thioether, thiol-maleimide or amide linkage. Other ways of linking the IL-2 variant to the cargo include use of a C-terminal aldehyde to form an oxime, use of a click reaction or formation of a morpholino linkage with a basic amino acid on the peptide.

When the agent of interest is a peptide or a protein including an antibody or functional fragment thereof, the IL-2 variant is advantageously provided as a chimeric fusion protein comprising the heterologous agent of interest (different from IL-2 or IL-2 fragment) fused to the N-terminus or the C-terminus or inserted into the amino acid sequence of the IL-2 variant of the invention, directly or via a peptide spacer as described above. The fusion protein is expressed from a chimeric construct in which a nucleotide sequence encoding the IL-2 variant of the invention is fused in frame to a nucleotide sequence encoding the peptide/protein of interest, using standard recombinant DNA techniques. The resulting fusion protein/peptide is of heterologous origin, i.e., it is different from naturally occurring peptides or proteins such as IL-2 or other cytokines of the same family.

The IL-2 variant can also be linked to the agent of interest (molecule or particle carrying the molecule) via non-covalent bounds such as ionic bonds, hydrogen bonds or hydrophobic interactions or a combination of such bonds. Non-limitative examples include antigen-antibody interaction between the IL-2 variant and an anti-IL-2 antibody; streptavidin-biotin interactions between a biotinylated IL-2 variant and an agent of interest (for example nanoparticles like Quantum dots) that is conjugated to streptavidin or a biotinylated agent and an IL-2 variant that is conjugated to streptavidin.

In preferred embodiments, the IL-2 variant is provided as a chimeric fusion protein comprising a heterologous protein or peptide of interest fused to the N-terminus or the C-terminus or inserted into the amino acid sequence of the IL-2 variant of the invention, directly or via a peptide spacer. The protein or peptide of interest is preferably selected from the group comprising: whole antibody or antibody Fc region, preferably whole human antibody or human Fc region; multi-specific antigen binding protein such as bispecific antibody; Ankyrin and Designed Ankyrin Repeat Protein (DARPin); MHC-peptide multimer such as class I or class II MHC-peptide tetramer, in particular MHC-peptide multimer wherein the peptide is derived from an antigen capable of inducing auto-immune or allo-immune response(s) such as a self-antigen. In some more preferred embodiments, the antibody is an antibody against a surface molecule specific for Tregs or a functional fragment thereof comprising at least the antigen binding site, preferably an anti-CTLA-4, anti-CD25, anti-CCR8, anti-ICOS, anti-IKZF2, anti-CD70, anti-GARP, anti-IL1R1, anti-CD39, anti-CCR4 or anti-CD177 antibody; more preferably human or humanized antibody or whole antibody molecule, still more preferably whole human or humanized antibody molecule.

The protein or peptide of interest is advantageously fused to the N-terminus or the C-terminus of the IL-2 variant of the invention, directly or via a peptide spacer.

In preferred embodiments, the IL-2 variant or derived fusion protein as disclosed above, is complexed with an anti-IL-2 antibody. In some more preferred embodiments the anti-IL-2 antibody is an IL-2 antibody with pro-Treg function, i.e., which blocks IL-2RB/IL-2 interaction and induces structure modification on IL-2. Such antibodies are well-known in the art and include for example clone JES6-1A12 (rat IgG2A anti-mouse IL-2) and clone 5344.111 (mouse IgG1 anti-human IL-2). These Abs have shown in vivo capacity to expand Tregs in pre-clinical models of diabetes (Tang Q et al, Immunity, 2008, 28, 687-97; Grinberg-Bleyer Y et al, J Exp Med, 2010, 207, 1871-8), allergy (Smaldini P L et al, Allergy, 2018, 73, 885-895), multiple sclerosis (Webster K. E. et al, J Exp Med, 2009, 206, 751-60), rheumatoid arthritis (Lee-S Y, et al, Immunology, 2012, 137, 305-16) and transplantation (Vokaer B, et al, Transplant Proc., 2012, 44, 2840-4). In some other more preferred embodiments the anti-IL-2 antibody is an IL-2 antibody with pro-Teff function. Such antibodies are well-known in the art and include for example, clone S4B6 (rat IgG2A anti-mouse IL-2) and clone Mab602 (mouse IgG2a anti-human IL-2). These Abs have shown in vivo better capacity than IL-2 to control tumor growth in melanoma (as single treatment or combined) (Boyman O et al, Science 2006, 311, 1921-27, Krieg et al, PNAS, 2010, 107, 11906-11, Caudana T et al, 2019, Cancer Immunol Res, 7, 443-457) and lymphoma (Newman R G et al, Blood, 2014, 123, 3045-55). The anti-IL-2 antibody is advantageously a human or humanized anti-IL-2 antibody, including humanized antibodies derived from the above mouse or rat monoclonal antibodies.

In preferred embodiments, the IL-2 variant or derived fusion protein as disclosed above, is complexed with an antibody against a Treg specific surface molecule as defined above, preferably a whole antibody, more preferable a whole human antibody.

In preferred embodiments, the IL-2 variant is linked to a CAR T-cell, in particular a patient's CAR T-cell.

The term "IL-2 variant" as used herein encompasses the different forms of IL-2 variant disclosed herein, such as an IL-2 variant, modified or not, associated or not with at least an agent of interest in the form of a complex, conjugate or fusion protein as disclosed above.

The IL-2 variant according to the invention can be made by routine techniques in the art, in particular by expression of a recombinant DNA in a suitable cell system (eukaryotic or prokaryotic) and screened for activity (i.e. capable of preferentially stimulating T-regulatory cells) using the assays described herein or other similar assays.

Polynucleotide, Vector and Host Cell

The invention relates also to an isolated polynucleotide encoding the IL-2 variant in expressible form.

The polynucleotide encoding the IL-2 variant in expressible form refers to a nucleic acid molecule which, upon expression in a cell or a cell-free system, results in a functional protein.

The polynucleotide, either synthetic or recombinant, may be DNA, RNA or combination thereof, either single- and/or double-stranded. The polynucleotide is operably linked to at least one transcriptional regulatory sequence and, optionally to at least one translational regulatory sequence. Preferably the polynucleotide comprises a coding sequence which is optimized for the host in which the IL-2 variant is expressed; more preferably, said polynucleotide sequence is selected from the group consisting of: SEQ ID NO: 9 to 14, which encode the IL-2-variant of SEQ ID NO: 3 to 8, respectively.

The polynucleotide according to the invention is prepared by the conventional methods known in the art. For example, it is produced by amplification of a nucleic sequence by PCR or RT-PCR, by screening genomic DNA libraries by hybridization with a homologous probe, or else by total or partial chemical synthesis.

Another aspect of the invention is a recombinant vector comprising said polynucleotide. The recombinant vector is advantageously an expression vector capable of expressing said polynucleotide when delivered into a host cell such as prokaryotic or eukaryotic cell, for example mammalian or bacterial cell. Recombinant vectors include usual vectors used in genetic engineering and gene therapy including for example plasmids and viral vectors.

The recombinant vectors are constructed and introduced into host cells by the conventional recombinant DNA, genetic engineering and gene therapy techniques, which are known in the art.

Thus, a further aspect of the invention provides a host cell comprising said polynucleotide or recombinant vector.

In some embodiments, the host cell is a patient cell such as T cell, NK cell or CAR T-cell, which is modified by the polynucleotide or vector according to the invention, for use for adoptive T cell therapy.

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5377 (IL2-V1).

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5378 (IL2-V2).

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5379 (IL2-V3).

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5380 (IL2-V4).

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5381 (IL2-V5).

In some embodiments, the host cell of the invention is the host cell deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5382 (IL2-V6).

The polynucleotide, vector, cell of the invention are useful for the production of the variants of the invention using well-known recombinant DNA techniques.

Pharmaceutical Composition and Therapeutic Use

The IL-2 variant, polynucleotide, vector and/or cell according to the invention are used for treating immune disorders.

As used herein, the terms "treatment" or "treat" refer to both prophylactic or preventive treatment as well as curative or disease modifying treatment, including treatment of patients at risk of contracting the disease or suspected to have contracted the disease as well as patients who are ill or have been diagnosed as suffering from a disease or medical condition, and include suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment.

In some embodiments, the IL-2 variant, polynucleotide, vector and/or cell according to the invention are used to expand Tregs ex vivo or in vivo or to block IL-2-mediated overactivation of the immune system, for treating diseases associated with immune dysregulation where immunomodulation or immunosuppression is beneficial, including diseases associated with dysfunction or overactivity of the immune system. In particular, the IL-2 variants capable of preferentially stimulating T-regulatory cells (Treg agonists) are used for treating immune disorders associated with dysfunction of the immune system such as allergic and auto-immune diseases and immune disorders associated with overactivity of the immune system such as acute or chronic inflammatory diseases, GVHD and graft-rejection. The IL-2-antagonist variants are used for treating diseases associated with overactivity of the immune system including an overproduction of IL-2 like GVHD, in particular acute GVHD and others like acute or chronic inflammatory diseases and graft-rejection.

For ex vivo therapy, a peripheral blood sample is collected from the patient; T cells are expanded in vitro using the IL-2 variant, polynucleotide and/or vector according to the invention, and the expanded Tregs are then re-injected into the patient. For in vivo therapy, the IL-2 variant, polynucleotide and/or vector according to the invention are administered to the patient and the Tregs are expanded in vivo in the patient. Alternatively or additionally, IL-2 already present in the patient is antagonized by the IL-2 variant.

In some embodiments, the IL-2-antagonist variant, polynucleotide, vector and/or cell according to the invention are used to inhibit Tregs by depriving them from IL-2 and thus allowing the stimulation of immune responses including B, NK, CD4+ or CD8+ T cells, DC, macrophages and others, for treating cancer or infectious diseases or increasing the immune response against vaccines, in particular vaccines for cancer or infectious diseases. In some preferred embodiments, the IL-2-antagonist variant, polynucleotide, vector and/or cell according to the invention are used to stimulate an anti-tumoral CD8+ T-cell response or a CD8+ T-cell response against a pathogen or a vaccine including a vaccine against cancer or infectious disease.

For in vivo therapy, the IL-2-antagonist variant, polynucleotide and/or vector according to the invention are administered to the patient and the Tregs are inhibited or eliminated in vivo in the patient, unleashing immune cells (B, NK, CD4+ or CD8+ T cells; DC; macrophages and others) from Treg suppression.

The present invention relates to a pharmaceutical composition comprising, as active substance, an IL-2 variant, polynucleotide, vector, and/or cell, according to the invention, and at least one pharmaceutically acceptable vehicle and/or carrier.

The pharmaceutical composition is formulated for administration by a number of routes, including but not limited to oral, parenteral and local. The pharmaceutical vehicles are those appropriate to the planned route of administration, which are well known in the art.

The pharmaceutical composition may further comprise a carrier. Non-limitative examples of carriers suitable for use in the composition of the invention include uni- or multi-lamellar liposomes, ISCOMS, virosomes, viral pseudopar-ticles, saponin micelles, saccharides (poly(lactide-co-gly-colide)) or gold microspheres, and nanoparticles.

The pharmaceutical composition comprises a therapeutically effective amount of the IL-2 variant, polynucleotide, vector and/or cell sufficient to show a positive medical response in the individual to whom it is administered. A positive medical response refers to the reduction of subsequent (preventive treatment) or established (therapeutic treatment) disease symptoms. The positive medical response comprises a partial or total inhibition of the symptoms of the disease. A positive medical response can be determined by measuring various objective parameters or criteria such as objective clinical signs of the disease and/or the increase of survival. A medical response to the composition according to the invention can be readily verified in appropriate animal models of the disease which are well-known in the art and illustrated in the examples of the present application.

The pharmaceutically effective dose depends upon the composition used, the route of administration, the type of mammal (human or animal) being treated, the physical characteristics of the specific mammal under consideration, concurrent medication, and other factors, that those skilled in the medical arts will recognize.

By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the pharmaceutical composition comprises another active agent wherein said active agent is a pharmaceutical agent or therapeutic capable of preventing, treating or ameliorating a disease in humans or animals. The active agent may be a protein including an antibody, an oligonucleotide including an antisense oligonucleotide, peptide nucleic acid (PNA), small interfering RNA, locked nucleic acids (LNA), phosphorodiamidate morpholino oligonucleotides (PMO) and decoy DNA molecule, a plasmid, an aptamer including DNA, RNA or peptide aptamer, a small or large chemical drug, or mixtures thereof. In particular, the active agent may be an anti-inflammatory or immunomodulatory agent such as for example rapamycin or corticoids. The active agent may also be an anticancer or anti-infectious agent or an antigen such as a tumor antigen or an antigen of a pathogen.

The invention provides also an IL-2 variant, polynucleotide, vector, cell or pharmaceutical composition according to the invention for use as a medicament.

The invention provides also an IL-2 variant, polynucleotide, vector, cell, or pharmaceutical composition according to the invention for use in the prevention or treatment of immune disorders.

In some embodiments, the disease associated with immune dysfunction or dysregulation is a disease where immunosuppression is beneficial such as with no limitations an allergic disease, an autoimmune disease, and diseases associated with overactivity of the immune system, such as with no limitations a chronic or acute inflammatory disease, graft-versus-host disease (GVHD) or graft rejection. Non-limiting examples of autoimmune diseases include: type 1 diabetes, rheumatoid arthritis, psoriasis and psoriatic arthritis, multiple sclerosis, Systemic lupus erythematosus (lupus), Inflammatory bowel disease such as Crohn's disease and ulcerative colitis, Addison's disease, Grave's disease, Sjögren's disease, alopecia areata, autoimmune thyroid disease such as Hashimoto's thyroiditis, myasthenia gravis, vasculitis including HCV-related vasculitis and systemic vasculitis, uveitis, myositis, pernicious anemia, celiac disease, Guillain-Barre Syndrome, chronic inflammatory demyelinating polyneuropathy, scleroderma, hemolytic anemia, glomerulonephritis, autoimmune encephalitis, fibromyalgia, aplastic anemia and others. Non-limiting examples of inflammatory and allergic diseases include: neuro-degenerative disorders such as Parkinson disease, chronic infections such as parasitic infection or disease like *Trypanosoma cruzi* infection, allergy such as asthma, atherosclerosis, chronic nephropathy, and others. The disease may be allograft rejection including transplant-rejection, graft-versus-host disease (GVHD) and spontaneous abortion In some embodiments, the disease associated with immune dysregulation or dysfunction is a disease where inhibition of Tregs and/or stimulation of immune responses, in particular CD8+ T-cell immune responses, is beneficial such as with no limitations cancers and infectious diseases. The invention includes the treatment of infectious diseases and cancer and the increase of the immune response against vaccines, in particular vaccines for cancer or infectious diseases.

As used herein, the term "cancer" refers to any member of a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. The term cancer according to the present invention also comprises cancer metastases and relapse of cancer. Cancers are classified by the type of cell that the tumor resembles and, therefore, the tissue presumed to be the origin of the tumor. For example, carcinomas are malignant tumors derived from epithelial cells. This group represents the most common cancers, including the common forms of breast, prostate, lung, and colon cancer. Lymphomas and leukemias include malignant tumors derived from blood and bone marrow cells. Sarcomas are malignant tumors derived from connective tissue or mesenchymal cells. Mesotheliomas are tumors derived from the mesothelial cells lining the peritoneum and the pleura. Gliomas are tumors derived from glia, the most common type of brain cell. Germinomas are tumors derived from germ cells, normally found in the testicle and ovary. Choriocarcinomas are malignant tumors derived from the placenta.

As used herein, the term "cancer" refers to any cancer that may affect any one of the following tissues or organs: breast; liver; kidney; heart, mediastinum, pleura; floor of mouth; lip; salivary glands; tongue; gums; oral cavity; palate; tonsil; larynx; trachea; bronchus, lung; pharynx, hypopharynx, oropharynx, nasopharynx; esophagus; digestive organs such as stomach, intrahepatic bile ducts, biliary tract, pancreas, small intestine, colon; rectum; urinary organs such as bladder, gallbladder, ureter; rectosigmoid junction; anus, anal canal; skin; bone; joints, articular cartilage of limbs; eye and adnexa; brain; peripheral nerves, autonomic nervous system; spinal cord, cranial nerves, meninges; and various parts of the central nervous system; connective, subcutaneous and other soft tissues; retroperitoneum, peritoneum; adrenal gland; thyroid gland; endocrine glands and related structures; female genital organs such as ovary, uterus, cervix uteri; corpus uteri, vagina, vulva; male genital organs such as penis, testis and prostate gland; hematopoietic and reticuloendothelial systems; blood; lymph nodes; thymus.

The term "cancer" according to the invention comprises leukemias, seminomas, melanomas, teratomas, lymphomas, non-Hodgkin lymphoma, neuroblastomas, gliomas, adeno-carcinoma, mesothelioma (including pleural mesothelioma, peritoneal mesothelioma, pericardial mesothelioma and end stage mesothelioma), rectal cancer, endometrial cancer, thyroid cancer (including papillary thyroid carcinoma, follicular thyroid carcinoma, medullary thyroid carcinoma, undifferentiated thyroid cancer, multiple endocrine neoplasia type 2A, multiple endocrine neoplasia type 2B, familial medullary thyroid cancer, pheochromocytoma and paraganglioma), skin cancer (including malignant melanoma, basal cell carcinoma, squamous cell carcinoma, Kaposi's sarcoma, keratoacanthoma, moles, dysplastic nevi, lipoma, angioma and dermatofibroma), nervous system cancer, brain cancer (including astrocytoma, medulloblastoma, glioma, lower grade glioma, ependymoma, germinoma (pinealoma), glioblastoma multiform, oligodendroglioma, schwannoma, retinoblastoma, congenital tumors, spinal cord neurofibroma, glioma or sarcoma), skull cancer (including osteoma, hemangioma, granuloma, xanthoma or osteitis deformans), meninges cancer (including meningioma, meningiosarcoma or gliomatosis), head and neck cancer (including head and neck squamous cell carcinoma and oral cancer (such as, e.g., buccal cavity cancer, lip cancer, tongue cancer, mouth cancer or pharynx cancer)), lymph node cancer, gastrointestinal cancer, liver cancer (including hepatoma, hepatocellular carcinoma, cholangiocarcinoma, hepatoblastoma, angiosarcoma, hepatocellular adenoma and hemangioma), colon cancer, stomach or gastric cancer, esophageal cancer (including squamous cell carcinoma, larynx, adenocarcinoma, leiomyosarcoma or lymphoma), colorectal cancer, intestinal cancer, small bowel or small intestines cancer (such as, e.g., adenocarcinoma lymphoma, carcinoid tumors, Kaposi's sarcoma, leiomyoma, hemangioma, lipoma, neurofibroma or fibroma), large bowel or large intestines cancer (such as, e.g., adenocarcinoma, tubular adenoma, villous adenoma, hamartoma or leiomyoma), pancreatic cancer (including ductal adenocarcinoma, insulinoma, glucagonoma, gastrinoma, carcinoid tumors or vipoma), ear, nose and throat (ENT) cancer, breast cancer (including HER2-enriched breast cancer, luminal A breast cancer, luminal B breast cancer and triple negative breast cancer), cancer of the uterus (including endometrial cancer such as endometrial carcinomas, endometrial stromal sarcomas and malignant mixed Müllerian tumors, uterine sarcomas, leiomyosarcomas and gestational trophoblastic disease), ovarian cancer (including dysgerminoma, granulosa-theca cell tumors and Sertoli-Leydig cell tumors), cervical cancer, vaginal cancer (including squamous-cell vaginal carcinoma, vaginal adenocarcinoma, clear cell vaginal adenocarcinoma, vaginal germ cell tumors, vaginal sarcoma botryoides and vaginal melanoma), vulvar cancer (including squamous cell vulvar carcinoma, verrucous vulvar carcinoma, vulvar melanoma, basal cell vulvar carcinoma, Bartholin gland carcinoma, vulvar adenocarcinoma and erythroplasia of Queyrat), genitourinary tract cancer, kidney cancer (including clear renal cell carcinoma, chromophobe renal cell carcinoma, papillary renal cell carcinoma, adenocarcinoma, Wilms tumor, nephroblastoma, lymphoma or leukemia), adrenal cancer, bladder cancer, urethra cancer (such as, e.g., squamous cell carcinoma, transitional cell carcinoma or adenocarcinoma), prostate cancer (such as, e.g., adenocarcinoma or sarcoma) and testis cancer (such as, e.g., seminoma, teratoma, embryonal carcinoma, teratocarcinoma, choriocarcinoma, sarcoma, interstitial cell carcinoma, fibroma, fibroadenoma, adenomatoid tumors or lipoma), lung cancer (including small cell lung carcinoma (SCLC), non-small cell lung carcinoma (NSCLC) including squamous cell lung carcinoma, lung adenocarcinoma (LUAD), and large cell lung carcinoma, bronchogenic carcinoma, alveolar carcinoma, bronchiolar carcinoma, bronchial adenoma, lung sarcoma, chondromatous hamartoma and pleural mesothelioma), sarcomas (including Askin's tumor, sarcoma botryoides, chondrosarcoma, Ewing's sarcoma, malignant hemangioendothelioma, malignant schwannoma, osteosarcoma and soft tissue sarcomas), soft tissue sarcomas (including alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, plexiform fibrohistiocytic tumor, rhabdomyosarcoma, synovial sarcoma and undifferentiated pleomorphic sarcoma, cardiac cancer (including sarcoma such as, e.g., angiosarcoma, fibrosarcoma, rhabdomyosarcoma or liposarcoma, myxoma, rhabdomyoma, fibroma, lipoma and teratoma), bone cancer (including osteogenic sarcoma, osteosarcoma, fibrosarcoma, malignant fibrous histiocytoma, chondrosarcoma, Ewing's sarcoma, malignant lymphoma and reticulum cell sarcoma, multiple myeloma, malignant giant cell tumor chordoma, osteochronfroma, osteocartilaginous exostoses, benign chondroma, chondroblastoma, chondromyxoid fibroma, osteoid osteoma and giant cell tumors), hematologic and lymphoid cancer, blood cancer (including acute myeloid leukemia, chronic myeloid leukemia, acute lymphoblastic leukemia, chronic lymphocytic leukemia, myeloproliferative diseases, multiple myeloma and myelodysplasia syndrome), Hodgkin's disease, non-Hodgkin's lymphoma and hairy cell and lymphoid disorders, and the metastases thereof.

Infectious diseases, include viral, bacterial, fungal and parasitic diseases such as for example HIV/AIDS, viral hepatitis such as Hepatitis A, Hepatitis B, Hepatitis C, measles, malaria, and Chagas disease.

The invention provides also a method for treating a disease associated with immune dysfunction or dysregulation, comprising: administering a therapeutically effective amount of the pharmaceutical composition according to the invention to the patient.

The pharmaceutical composition of the present invention is generally administered according to known procedures, at dosages and for periods of time effective to induce a beneficial effect in the individual. The administration may be by injection or by oral, sublingual, intranasal, rectal or vaginal administration, inhalation, or transdermal application. The injection may be subcutaneous, intramuscular, intravenous, intraperitoneal, intradermal or else.

The pharmaceutical composition of the invention is advantageously used in combination with another therapy, in particular immunotherapy such as CAR-T cell therapy; therapy with an immunomodulatory agent, in particular an immunomodulatory monoclonal antibody or functional derivative thereof; therapy with anticancer or anti-infectious agents including therapeutic agents and vaccines against cancer and infectious diseases. The combined therapies may be separate, simultaneous, and/or sequential.

In some embodiments, the pharmaceutical composition is used for the prevention or treatment of humans.

In some embodiments, the pharmaceutical composition is used for the treatment of animals.

In some embodiments, the IL-2 variant, polynucleotide, vector, cell, and/or pharmaceutical composition according to the invention is administered in combination with additional cancer therapies. In particular, IL-2 variant, polynucleotide, vector, cell and/or pharmaceutical composition of the invention may be administered in combination with targeted therapy, immunotherapy such as immune checkpoint therapy and immune checkpoint inhibitor, co-stimulatory antibodies, chemotherapy and/or radiotherapy.

Immune checkpoint therapy such as checkpoint inhibitors include, but are not limited to programmed death-1 (PD-1) inhibitors, programmed death ligand-1 (PD-L1) inhibitors, programmed death ligand-2 (PD-L2) inhibitors, lymphocyte-activation gene 3 (LAG-3) inhibitors, T-cell immunoglobulin and mucin-domain containing protein 3 (TIM-3) inhibitors, T cell immunoreceptor with Ig and ITIM domains (TIGIT) inhibitors, B- and T-lymphocyte attenuator (BTLA) inhibitors, V-domain Ig suppressor of T-cell activation (VISTA) inhibitors, cytotoxic T-lymphocyte-associated protein 4 (CTLA-4) inhibitors, Indoleamine 2,3-dioxygenase (IDO) inhibitors, killer immunoglobulin-like receptors (KIR) inhibitors, KIR2L3 inhibitors, KIR3DL2 inhibitors and carcinoembryonic antigen-related cell adhesion molecule 1 (CEACAM-1) inhibitors. In particular, checkpoint inhibitors include antibodies anti-PD1, anti-PD-L1, anti-CTLA-4, anti-TIM-3, anti-LAG3. Co-stimulatory antibodies deliver positive signals through immune-regulatory receptors including but not limited to ICOS, CD137, CD27, OX-40 and GITR.

Examples of anti-PD1 antibodies include, but are not limited to, nivolumab, cemiplimab (REGN2810 or REGN-2810), tislelizumab (BGB-A317), spartalizumab (PDR001 or PDR-001), ABBV-181, JNJ-63723283, BI 754091, MAG012, TSR-042, AGEN2034, pidilizumab, nivolumab (ONO-4538, BMS-936558, MDX1106, GTPL7335 or Opdivo), pembrolizumab (MK-3475, MK03475, lambrolizumab, SCH-900475 or Keytruda) and antibodies described in International patent applications WO2004004771, WO2004056875, WO2006121168, WO2008156712, WO2009014708, WO2009114335, WO2013043569 and WO2014047350.

Examples of anti-PD-L1 antibodies include, but are not limited to, LY3300054, atezolizumab, durvalumab and avelumab.

Examples of anti-CTLA-4 antibodies include, but are not limited to, ipilimumab (see, e.g., U.S. Pat. Nos. 6,984,720 and 8,017,114), tremelimumab (see, e.g., U.S. Pat. Nos. 7,109,003 and 8,143,379), single chain anti-CTLA4 antibodies (see, e.g., International patent applications WO1997020574 and WO2007123737) and antibodies described in U.S. Pat. No. 8,491,895.

Example of anti-VISTA antibodies are described in US patent application US20130177557.

Example of inhibitors of the LAG3 receptor are described in U.S. Pat. No. 5,773,578.

Example of KIR inhibitor is IPH4102 targeting KIR3DL2.

Targeted therapy, are drugs designed to interfere with specific molecules necessary for tumor growth and progression. For example, therapeutic monoclonal antibodies target specific antigens found on the cell surface, such as transmembrane receptors or extracellular growth factors. In some cases, monoclonal antibodies are conjugated to radio-isotopes or toxins to allow specific delivery of these cytotoxic agents to the intended cancer cell target. Small molecules can penetrate the cell membrane to interact with targets inside a cell. Small molecules are usually designed to interfere with the enzymatic activity of the target protein such as for example proteasome inhibitor, tyrosine kinase or cyclin-dependent kinase inhibitor, histone deacetylase inhibitor. Targeted therapy may also use cytokines. Examples of such targeted therapy include with no limitations: Ado-trastuzumab emtansine (HER2), Afatinib (EGFR (HER1/ERBB1), HER2), Aldesleukin (Proleukin), alectinib (ALK), Alemtuzumab (CD52), axitinib (kit, PDGFRbeta, VEGFR1/2/3), Belimumab (BAFF), Belinostat (HDAC), Bevacizumab (VEGF ligand), Blinatumomab (CD19/CD3), bortezomib (proteasome), Brentuximab vedotin (CD30), bosutinib (ABL), brigatinib (ALK), cabozantinib (FLT3, KIT, MET, RET, VEGFR2), Canakinumab (IL-1 beta), carfilzomib (proteasome), ceritinib (ALK), Cetuximab (EGFR), cofimetinib (MEK), Crizotinib (ALK, MET, ROS1), Dabrafenib (BRAF), Daratumumab (CD38), Dasatinib (ABL), Denosumab (RANKL), Dinutuximab (B4GALNT1 (GD2)), Elotuzumab (SLAMF7), Enasidenib (IDH2), Erlotinib (EGFR), Everolimus (mTOR), Gefitinib (EGFR), Ibritumomab tiuxetan (CD20), Sonidegib (Smoothened), Sipuleucel-T, Siltuximab (IL-6), Sorafenib (VEGFR, PDGFR, KIT, RAF), (Tocilizumab (IL-6R), Temsirolimus (mTOR), Tofacitinib (JAK3), Trametinib (MEK), Tositumomab (CD20), Trastuzumab (HER2), Vandetanib (EGFR), Vemurafenib (BRAF), Venetoclax (BCL2), Vismodegib (PTCH, Smoothened), Vorinostat (HDAC), Ziv-aflibercept (PIGF, VEGFA/B).

In some embodiments, the IL-2 variant, polynucleotide, vector, cell and/or pharmaceutical composition of the invention is administered to the patient in combination with chemotherapy. As used herein, the term "chemotherapy" has its general meaning in the art and refers to the treatment that consists in administering to the patient a chemotherapeutic agent. Chemotherapeutic agents include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietyle-nephosphoramide, triethiylenethiophosphoramide and trim-ethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; methylhydrazine derivatives including N-methylhydrazine (MIH) and procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylomithine (DMFO); retinoids such as retinoic acid; capecitabine; anthracyclines, nitrosoureas, antimetabolites, epipodophylotoxins, enzymes such as L-asparaginase; anthracenediones; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide; and pharmaceutically acceptable salts, acids or derivatives of any of the above.

In some embodiments, the IL-2 variant, polynucleotide, vector, cell and/or pharmaceutical composition of the invention is administered to the patient in combination with radiotherapy. Suitable examples of radiation therapies include, but are not limited to external beam radiotherapy (such as superficial X-rays therapy, orthovoltage X-rays therapy, megavoltage X-rays therapy, radiosurgery, stereotactic radiation therapy, Fractionated stereotactic radiation therapy, cobalt therapy, electron therapy, fast neutron therapy, neutron-capture therapy, proton therapy, intensity modulated radiation therapy (IMRT), 3-dimensional confor-
mal radiation therapy (3D-CRT) and the like);
brachytherapy; unsealed source radiotherapy; tomotherapy;
and the like. Gamma rays are another form of photons used
in radiotherapy. Gamma rays are produced spontaneously as
certain elements (such as radium, uranium, and cobalt 60)
release radiation as they decompose, or decay. In some
embodiments, radiotherapy may be proton radiotherapy or
proton minibeam radiation therapy. Proton radiotherapy is
an ultra-precise form of radiotherapy that uses proton beams
(Prezado Y, Jouvion G, Guardiola C, Gonzalez W, Juchaux
M, Bergs J, Nauraye C, Labiod D, De Marzi L, Pouzoulet F,
Patriarca A, Dendale R. Tumor Control in RG2 Glioma-
Bearing Rats: A Comparison Between Proton Minibeam
Therapy and Standard Proton Therapy. Int J Radiat Oncol
Biol Phys. 2019 Jun. 1; 104(2):266-271. doi: 10.1016/
j.ijrobp.2019.01.080; Prezado Y, Jouvion G, Patriarca A,
Nauraye C, Guardiola C, Juchaux M, Lamirault C, Labiod
D, Jourdain L, Sebrie C, Dendale R, Gonzalez W, Pouzoulet
F. Proton minibeam radiation therapy widens the therapeutic
index for high-grade gliomas. Sci Rep. 2018 Nov. 7; 8(1):
16479. doi: 10.1038/s41598-018-34796-8). Radiotherapy
may also be FLASH radiotherapy (FLASH-RT) or FLASH
proton irradiation. FLASH radiotherapy involves the ultra-
fast delivery of radiation treatment at dose rates several
orders of magnitude greater than those currently in routine
clinical practice (ultra-high dose rate) (Favaudon V, Fouil-
lade C, Vozenin M C. The radiotherapy FLASH to save
healthy tissues. Med Sci (Paris) 2015; 31: 121-123. DOI:
10.1051/medsci/20153102002); Patriarca A., Fouillade C.
M., Martin F., Pouzoulet F., Nauraye C., et al. Experimental
set-up for FLASH proton irradiation of small animals using
a clinical system. Int J Radiat Oncol Biol Phys, 102 (2018),
pp. 619-626. doi: 10.1016/j.ijrobp.2018.06.403. Epub 2018
Jul. 11).

Use for Antibody Screening

The IL-2 variant according to the invention can be used
for the screening of anti-IL-2 antibodies with pro-Teff or
pro-Treg, activity using standard immunoassays that are
well-known in the art.

In this connection, the invention relates to a method of
screening anti-IL-2 antibodies with pro-Teff or pro-Treg,
activity, comprising at least the steps of:

a) contacting an anti-IL-2 antibody with a variant accord-
     ing to the invention, and b) measuring the level of bound antibody from step a),
     wherein if the level of bound antibody is more than
     70% (preferably 80%, 90%, or more) of the reference
     value, then the anti-IL-2 antibody is likely to have
     pro-Teff activity; and wherein if the level of bound
     antibody is less than 50% (preferably 40%, 30%, 20%,
     10% or less) than the reference value, then the anti-IL-2
     antibody is likely to have pro-Treg activity.

Antibodies with pro-Teff activity are in particular anti-
bodies having CD25 mimotope binding.

The reference value is usually determined by contacting
the antibody with wild-type IL-2 in the same conditions.
Step a) is advantageously performed using IL-2 variant
immobilized on a solid surface (plate, beads). Step b) is
performed using labeled primary or secondary antibodies.
The assay may be ELISA, Fluoroimmnoassay (FIA) or
Chemiluminescenceimmunoassay (CLIA) depending upon
the label that is used. The assay may be a high throughput
assay, for example using microfluidic devises.

The invention relates also to a kit for performing the
screening method of the invention, comprising the IL-2
variant according to the invention.

In the various embodiments, the kit may further comprise
instructions for use, and/or a labelled antibody.

The practice of the present invention will employ, unless
otherwise indicated, conventional techniques which are
within the skill of the art. Such techniques are explained
fully in the literature.

The invention will now be exemplified with the following
examples, which are not limitative, with reference to the
attached drawings in which:

FIGURE LEGENDS

FIG. 1: Multiple sequence alignment of IL-2 from differ-
ent species used in the evolutive filter. *Homo sapiens* (SEQ
ID NO: 1); Hylobates lar (SEQ ID NO: 15); *Macaca* mulatta
(SEQ ID NO: 16); *Macaca nemestrina* (SEQ ID NO: 17);
*Macaca fascicularis* (SEQ ID NO: 18); *Cercocebus torqua-
tus* (SEQ ID NO: 19); *Aotus vociferans* (SEQ ID NO: 20);
*Papio hamadryas* (SEQ ID NO: 21); *Mus musculus* (SEQ ID
NO: 22); *Rattus norvegicus*(SEQ ID NO: 23); *Meriones
unguiculatus* (SEQ ID NO: 24; *Cavia porcellus* (SEQ ID
NO: 25); *Oryctolagus cuniculus* (SEQ ID NO: 26); *Bos
taurus* (SEQ ID NO: 27); *Ovis aries* (SEQ ID NO: 28);
*Cervus elaphus* hippelaphus (SEQ ID NO: 29); *Capra hircus*
(SEQ ID NO: 30); *Delphinapterus leucas* (SEQ ID NO: 31);
*Orcinus orca* (SEQ ID NO: 32); *Sus scrofa* (SEQ ID NO: 33;
*Equus caballus* (SEQ ID NO: 34); *Felis catus* (SEQ ID NO:
35); *Canis lupus familiaris* (SEQ ID NO: 36); *Halichoerus
grypus* ((SEQ ID NO: 37); *Mirounga angustirostris* (SEQ
ID NO: 38) and *Gallus gallus* (SEQ ID NO: 39).

Figure 2:
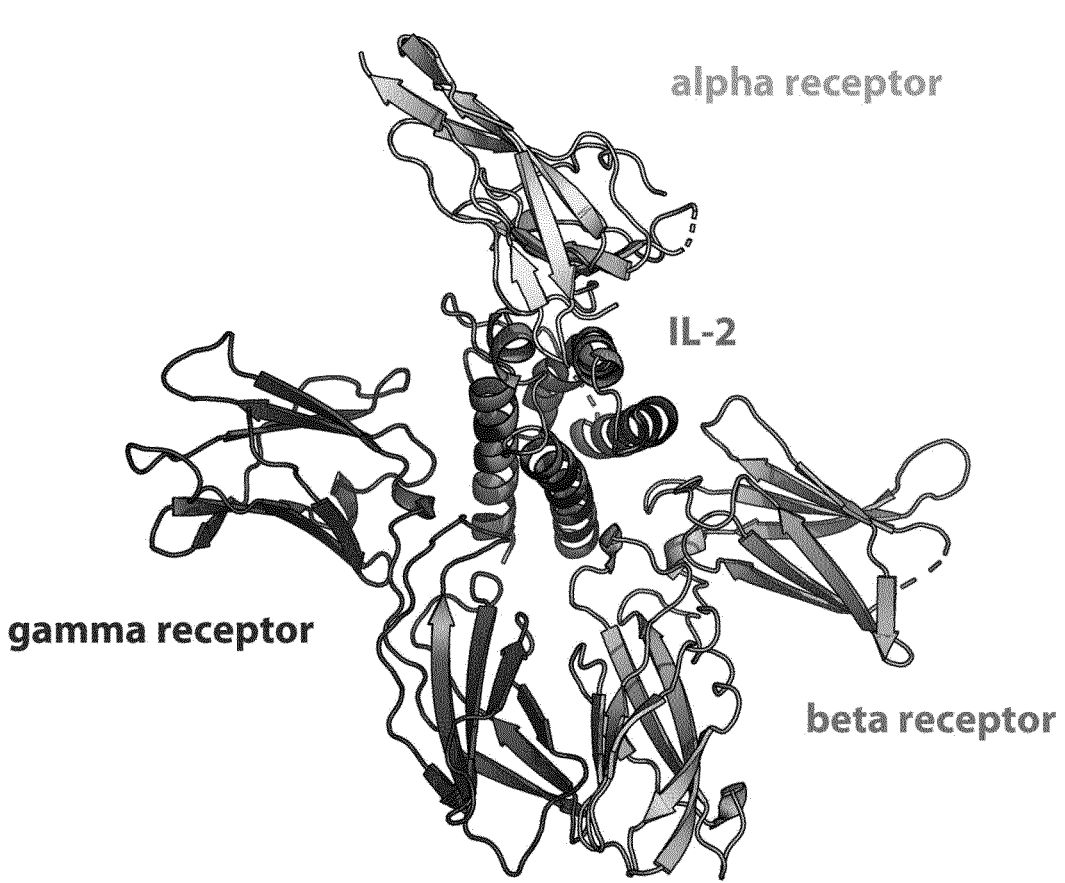

FIG. 2: Structure of the quaternary complex IL-2 with its
α (CD25), β (CD122), and γC (CD132) receptors as indi-
cated.

The resurfaced positions in the IL-2-V2 are indicated.

Figure 3:
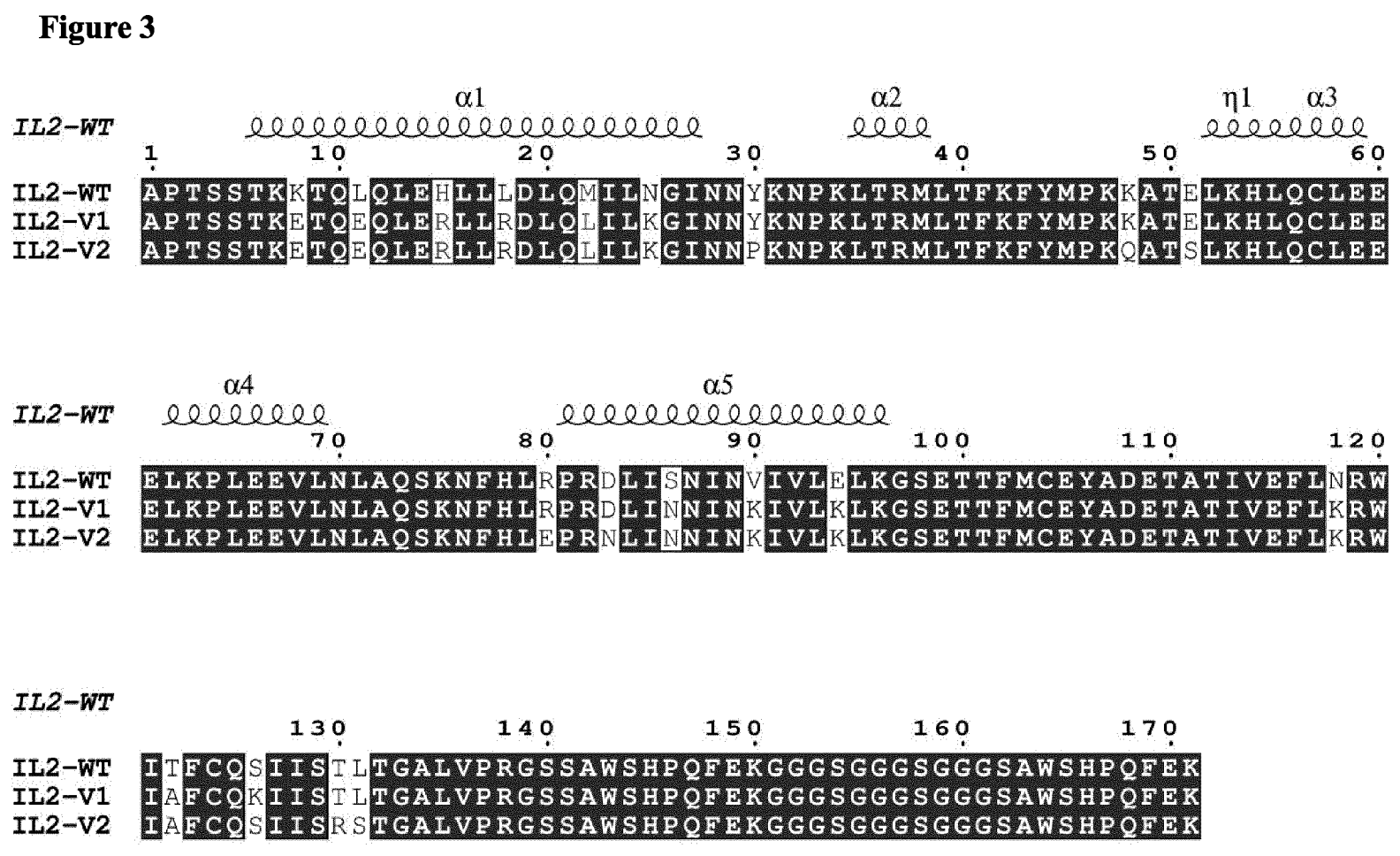

FIG. 3: Sequence alignment of IL-2-WT construct and the
resurfaced variants IL-2-V1 and IL-2-V2.

IL-2-WT construct (SEQ ID NO: 2). IL-2-V1 (SEQ ID NO:
3). IL-2-V2 (SEQ ID NO: 4).

Figure 4:
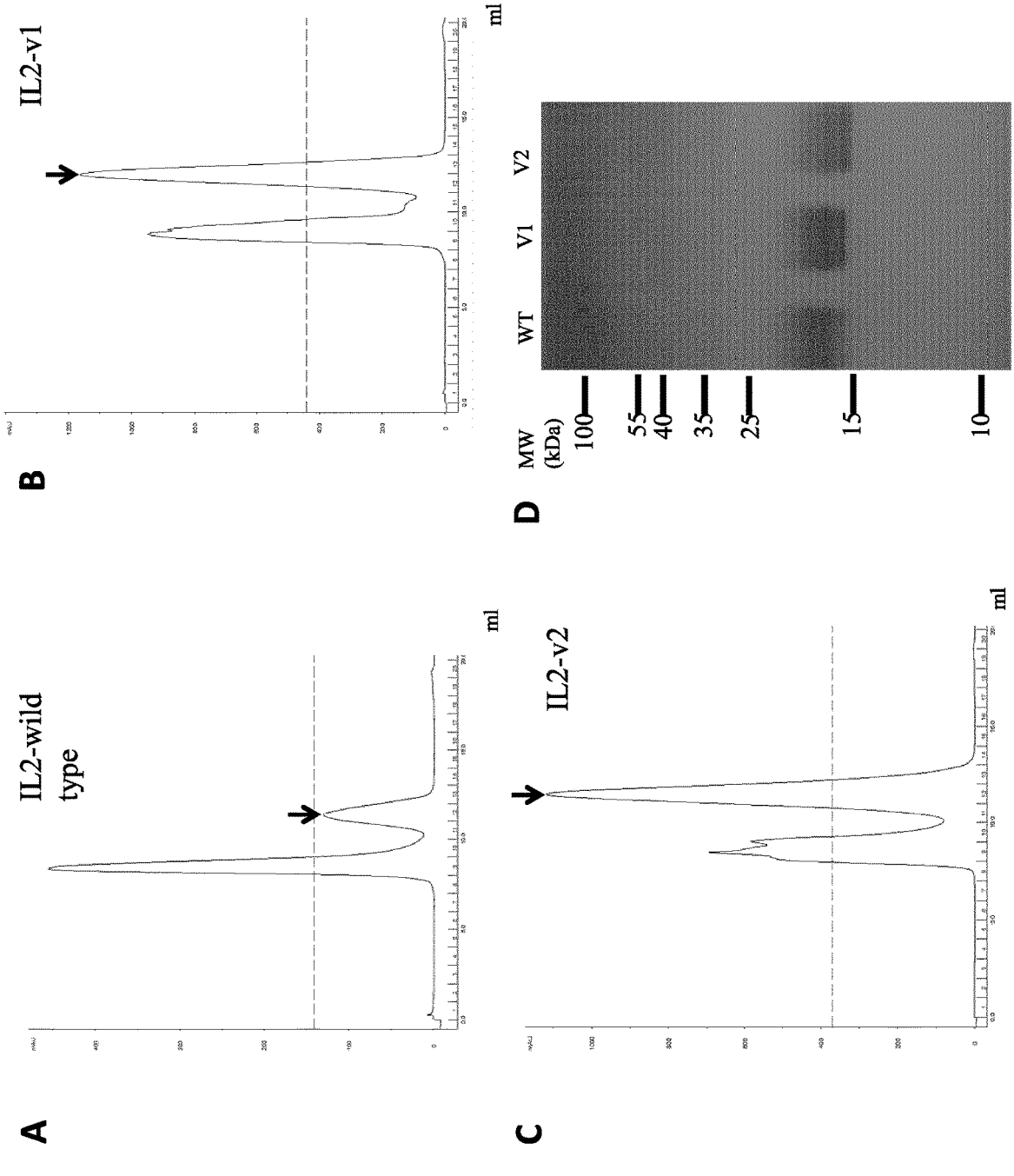

FIG. 4: Size-exclusion chromatography and SDS-PAGE
analysis of recombinant wild type and resurfaced variants of
IL-2

A. IL-2 wild-type. B. IL-2-V1. C. IL-2-V2. The peak used
     for experimental tests is indicated with an arrowhead.
     D. SDS-PAGE analysis of IL-2 wild-type (WT); IL-2-
     V1 (V1) and IL-2-V2 (V2). Gel: Laemli, 15% acryl-
     amide. Samples: WT: 3.4 µg. V1: 3.6 µg. V2: 2-2.9 µg.
     The samples were denatured under reducing conditions
     (DTT).

Figure 5:
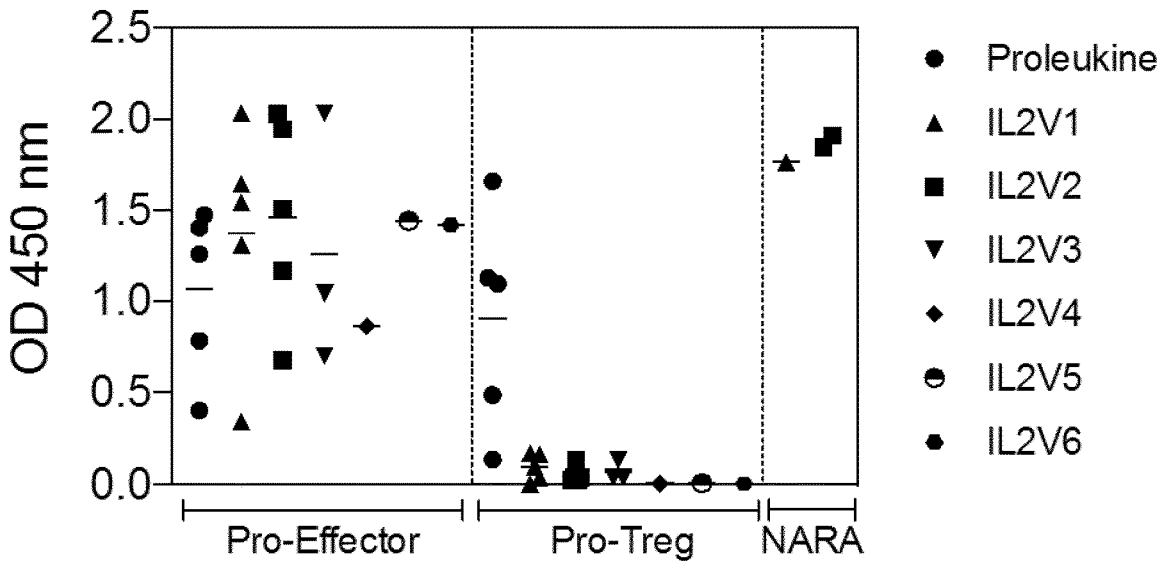

FIG. 5: ELISA to evaluate the specific binding of different
anti-IL-2 antibodies to the different IL-2 variants.

An ELISA test was used to evaluate the selectivity of the
IL-2Vs to antibodies (Ab) with pro-T-effector or pro-Treg
function. For that, a typical ELISA test was performed by
coating the plate with Proleukine, IL-2V1, IL-2V2, IL-2V3,
IL-2V4, IL-2V5 or IL-2V6 (all at 6 ug/mL). The evaluated
Abs were: MAB605 (mouse anti-human IL-2 Ab with Pro-T
effector activity in vivo), 5344 (mouse anti-human IL-2 Ab
with Pro-Treg activity in vivo) and NARA (scFV antibody
with Pro-T-effector activity in vivo, derived from Arenas-
Ramirez et all, Sci. Transl. Med., 2016, 8, 367ra166). To
detect the anti-IL-2 Abs, an anti-mouse IgG-HRP Ab or an
anti-M13-HRP Ab for NARA were used, and the absorbance
was read at 450 nm. Shown are OD values from which
absorbance of control wells (uncoated wells incubated with
the corresponding anti-IL-2Ab plus anti-mouse IgG-HRP
Ab) were subtracted.

Figure 6:
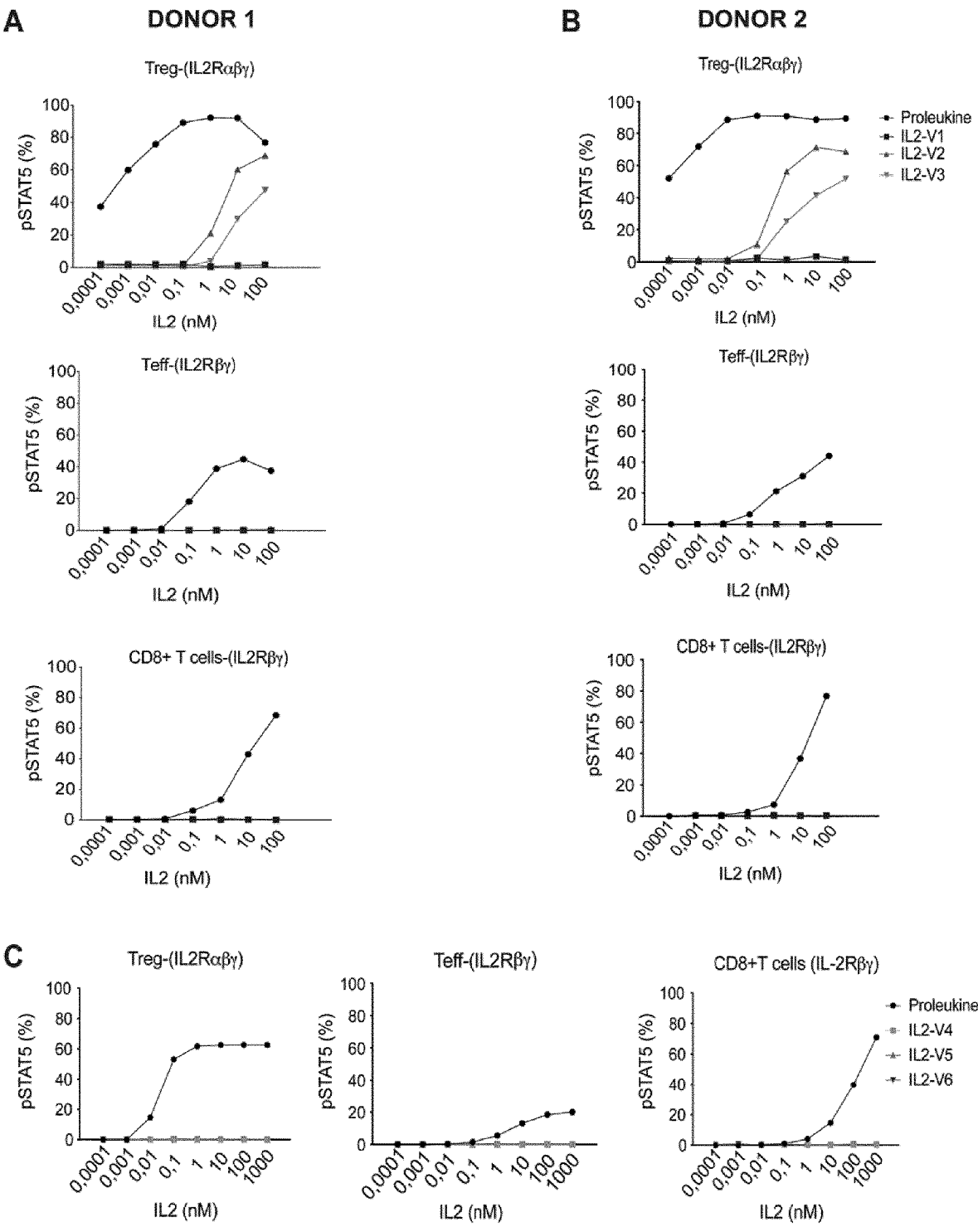

FIG. 6: Human IL-2V2 and IL-2V3, but not IL-2V1, IL-2V4, IL-2V5 and IL-2V6, selectively induce STAT-5 phosphorylation in Treg cells.

CD3+ cells were purified from human PBMCs and incubated with different concentrations of Proleukine, IL-2V1, IL-2V2, IL-2V3, IL-2V4, IL-2V5 or IL-2V6 (from 0,0001 nM to 1000 nM). Phosphorylation of STAT5 (STAT5-P) in human Treg cells (IL-2Rαβγ), CD4+ Teff cells (IL-2Rβγ) and CD8+ T cells (IL-2Rβγ) was measured by flow cytometry. (A-B) Frequency of STAT5-P+ cells among different T cell populations in two different healthy donors using Proleukine, IL-2V1, IL-2V2 and IL-2V3. (C) Frequency of STAT5-P+ cells among different T cell populations from one healthy donor using Proleukine, IL-2V4, IL-2V5 and IL-2V6. Shown are results obtained in two independent experiments.

FIG. 7: hIL-2Vs delay clinical GVHD development

NSG-SGM mice received by i.v. route human PBMCs containing 6×10^6 CD3+ T cells and were treated for 5 consecutive days with 6 ug/dose of Proleukine, IL-2V1 and IL-2V2 by i.p. route. (A) Mean of body weight change evolution expressed as percentage (%) of the initial body weight of the different treatment groups, and (B) Kaplan-Meier survival curves of the grafted mice. Untreated n=4; Proleukine, n=4; IL-2V1 n=5; IL-2V2, n=5.

FIG. 8: hIL-2Vs preferentially increase circulating human Treg cells in a murine model of acute GVHD NSG-SGM mice received by i.v. route human PBMCs containing 6×10^6 CD3+ T cells and were treated for 5 consecutive days with 6 ug/dose of Proleukine, IL-2V1 and IL-2V2 by i.p. route. Blood samples were taken at day 5, 10 and 21 after PBMCs injection. Frequency of (A) human CD8+ T cells; (B) human CD4+Tconv cells (CD4+ Foxp3− T-effector cells) and human Tregs (CD4+ CD45RA− Foxp3^{High}) (C) and CD25+ Tregs (CD4+Foxp3+CD25^{High}) (D). Squares: donor 1. Circles: donor 2. Untreated, n=4; Proleukine, n=4; IL-2V1 n=5; IL-2V2, n=5.

FIG. 9: Human IL-2V1 competes with Proleukine to stimulate T cells. CD3+ cells were purified from human PBMCs and were incubated with different concentrations of Proleukine alone (from 0.0001 nM to 1000 nM; black curves), human IL-2V1 alone (from 0,0001 nM to 1000 nM; blue curve) or Proleukine (from 0,0001 nM to 1000 nM) in the presence of a fixed concentration of IL-2V1 (1000 nM, competition curve, red curve). Phosphorylation of STAT-5 (STAT5-P) was measured by flow cytometry. (A) Frequency of STAT5-P cells among Treg cells (IL-2Rαβγ). (B) Frequency of STAT5-P cells among CD4+Foxp3− T cells (IL-2Rβγ). (C) Frequency of STAT5-P cells among CD8+ T cells (IL-2Rβγ). (D) Frequency of STAT5-P+ cells among Treg, CD4+ Teff and CD8+ T cells induced by IL-2V1. A schematic representation of the high affinity (upper part) and intermediate affinity (middle) IL-2R interacting with the IL-2V1 is shown.

FIG. 10: IL-2V2 and IL-2V3 preferentially increase the frequency of Treg cells over Effector cells in vivo. C57BL/6 healthy mice were treated by i.p. injection of Proleukine (4 μM), IL-2V2 (40 μM), or IL-2V3 (40 μM). A group of mice were left untreated. n=3 mice per group of treated or untreated mice. Blood samples were taken after mice received 4 doses of Proleukine or IL-2Vs for FACS analysis.

(A) Frequency of: Tregs (CD4+ Foxp3+); Effector Memory CD8+ T cells (CD8+CD44^{high}) and NK cells, among CD45+ cells; Proliferating (Ki67+) Tregs, Effector Memory CD8+ T cells (CD44^{high} Ki67+) and NK cells, among CD45+ cells; (B) Ratio of Effector Memory CD8+ T cells (CD8+ CD44^{high}) to Tregs; Ratio of NK cells to Tregs.

Figure 11:
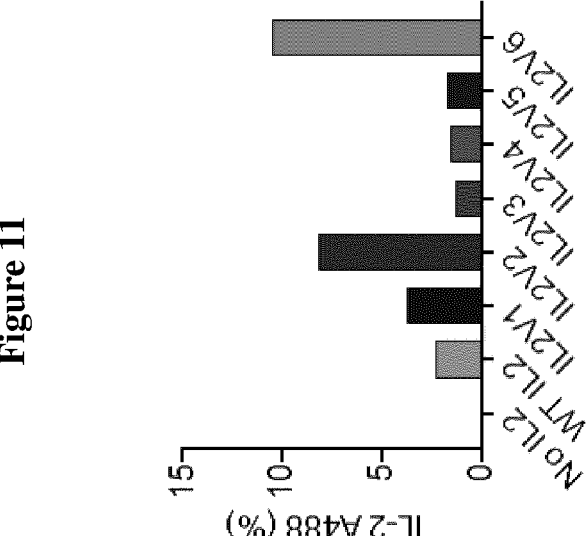

FIG. 11: IL-2 variants bind to the IL-2Rαβγ. Binding assay on IL-2-dependent human cell line Kit225 that constitutively expresses IL-2Rαβγ. Kit225 cells deprived of IL-2 for 2 days were incubated alone or with 10 μM of IL-2 wt, IL-2V1, V2, V3, V4, V5 and V6 produced with a Streptavidine Tag. After incubation, cells were stained with anti-Strep-Tag antibody (A-488) and analysed by flow cytometry.

FIG. 12: IL-2V antagonists compete with IL-2 for CD4+ T cell activation leaving active signaling in CD8+ T cells. CTV-labelled human PBMCs and CD25+ T cells (mixed at 50:50 ratio) were incubated for 96 h with anti-CD3/anti-CD28 beads (1:5 bead:cell ratio)+IL-2V1, 4, 6, anti-hIL-2mAb (Mab602) or PBS (endogenous IL-2 control). CTV dilution of CD4+Tconvs, Tregs and CD8+ T cells was measured by flow cytometry. Shown is the percentage (%) of CTV^{Low} cells (as a measure of divided cells) relative to PBS condition (max).

EXAMPLES

Example 1. Computational Design of Resurfaced Variants of IL-2

The atomic structure of the quaternary complex of IL-2 with its α (also known as CD25), β (CD122), and γ_c (CD132) receptors (PDB code 2B5I) were used to guide the computational design of new IL-2 variants that maintain the residues contacting the α receptor but modify the surface outside this region (FIG. 2). The general pipeline of the resurfacing design was the following: First, residues contacting the α receptor were defined as those residues of IL-2 with at least one atom at a distance of 8 Å or less from any atom of the α receptor. Once the amino acids in contact with CD25 were discarded, the set of candidate positions to be mutated were identified using an accessibility criterion and only those residues with >50% side-chain surface area exposed were selected (Fraczkiewicz et al., J. Comp. Chem, 1998. 19, 319-333).

Using this procedure, 28 candidate positions were identified on IL-2 surface. Next, to decide which set of mutations are allowed at each position, ortholog sequence analysis was combined with solubility criteria. To include evolutionary information, a multiple sequence alignment of IL-2 sequences from 26 different species was done (FIG. 1) and only mutation to residues present in any of the orthologs at a given position were allowed. This original set of mutations was further filtered by using solubility considerations, such that when possible, the presence of hydrophobic residues was discarded and all the polar and the native residues of IL-2 were allowed. Finally, the Rosetta "fixed backbone design application" was used to select low energy sequences, maintaining the native rotamer in all non-exposed residues (Kuhlman et al., Science, 2003. 302, 1364-8). The lowest energy design for a particular combination of resurfacing positions was selected for experimental testing. Using this procedure, different variants, termed IL-2-V1 to IL-2-V6 were designed (Table I). A C-terminal Strep-tag was added to the constructs for ease of purification. The wild-type human IL-2 construct with the C-terminal Strep-tag and derived IL-2 variants (IL-2-V1 to IL-2-V6) have a 171 amino acid sequence (SEQ ID NO: 2 to 8;

31

FIG. 3).

TABLE I

| | | | IL-2-variants | | | | | |
|---|---|---|---|---|---|---|---|---|
| Position | wt | Variant | V1 | V2 | V3 | V4 | V5 | V6 |
| 9 | K | E | ± | ± | ± | | ± | ± |
| 12 | L | E | ± | ± | ± | | ± | ± |
| 16 | H | R | ± | ± | ± | | ± | ± |
| 19 | L | R | ± | ± | ± | | ± | ± |
| 23 | M | L | ± | ± | ± | | ± | ± |
| 26 | N | K | ± | ± | ± | | ± | ± |
| 31 | Y | P | − | + | + | ± | + | − |
| 49 | K | Q | − | + | + | | − | + |
| 52 | E | S | − | + | + | | − | + |
| 81 | R | E | − | + | + | | − | + |
| 84 | D | N | − | + | + | | − | + |
| 87 | S | N | ± | ± | ± | | ± | ± |
| 91 | V | K | ± | ± | ± | | ± | ± |
| 95 | E | K | ± | ± | ± | | ± | ± |
| 119 | N | R | − | − | − | | − | − |
| 119 | N | K | + | + | − | | + | + |
| 123 | T | A | + | + | − | | + | + |
| 127 | S | K | + | − | − | | + | − |
| 131 | T | R | − | + | + | | − | + |
| 132 | L | S | − | + | + | | − | + |
| Number of mutations | | | 12 | 18 | 16 | 1 | 13 | 17 |

Example 2. Protein Expression and Purification

Genes encoding human IL-2, and IL-2 variants were codon optimized for expression in mammalian cells and synthesized with a C-terminal Strep-tag by GENSCRIPT (Piscataway, NJ, USA). The corresponding DNA sequences (SEQ ID NO: 9 to 14) were then cloned between AgeI and XhoI restriction sites of plasmid pHL-sec, a mammalian expression vector suitable for protein production in high yields (Aricescu et al., Acta Crystallogr D Biol Crystallogr., 2006, 62, 1243-50). Bacteria *E. coli* Top10 transformed with the different pHL-sec recombinant plasmids encoding each of the IL-2 variants were deposited at the Collection Nationale de Cultures de Microorganismes (CNCM) at the Institut Pasteur, 25 rue du Docteur Roux, 75724 Paris, FR on Nov. 15, 2018, under the deposit number CNCM I-5377 to CNCM I-5382 (IL-2-V1 to IL-2-V6). The transformed bacteria deposited at the CNCM under the deposit number CNCM I-5377 to CNCM I-5382 (IL-2-V1 to IL-2-V6) are grown in standard conditions such as in Luria-Bertani (LB) medium supplemented with 100 µg/mL ampicillin, at 37° C. under agitation >160 rpm. The viability of the transformed bacteria can be verified by standard assay such as plating a bacterial culture onto LB-agar plates supplemented with 100 µg/mL ampicillin and detecting the presence of bacterial colonies. The transformed bacteria can be preserved under standard conditions such as by freezing at −80° C. of a mixture of 0.5 mL of bacterial culture with 0.5 mL of 50% (V/V) glycerol in 2 mL Eppendorf tube. The proteins were produced by transient transfection of HEK293 FreeStyle cells (THERMO SCIENTIFIC) maintained in serum-free medium (Free Style 293 expression medium). Culture supernatants were harvested 3 days after transfection and Tris pH8.0 was added to a final concentration of 100 mM. The proteins were first purified by Streptactin affinity chromatography using a StrepTrap column (GE HEALTHCARE, Piscataway, NJ) and the eluted fractions were further purified by gel-filtration using a Superdex75 column (GE HEALTHCARE, Piscataway, NJ), resulting in a profile with two peaks, one corresponding to a monomeric protein and the other to an oligomer, presumably a dimer (FIG. 4). The fractions containing the monomeric peak were concentrated and used for experimental tests.

Example 3. IL-2Vs is a New Tool to Specifically Select Anti-IL-2Abs with Pro-Teff or Pro-Treg Activity An ELISA test was used to evaluate the selectivity of the IL-2 variants to antibodies (Ab) with pro-T-effector or pro-Treg function. For that, a typical ELISA test was performed by coating the plate with Proleukine, IL-2V1, IL-2V2, IL-2V3, IL-2V4, IL-2V5 or IL-2V6 (all at 6 ug/mL). The evaluated Abs were: MAB605 (mouse anti-human IL-2 Ab with Pro-T-effector activity in vivo), 5344 (mouse anti-human IL-2 Ab with Pro-Treg activity in vivo) and NARA (scFV antibody with Pro-T-effector activity in vivo, derived from Arenas-Ramirez et all, Sci. Transl. Med., 2016, 8, 367ra166). To detect the anti-IL-2 Abs, an anti-mouse IgG-HRP Ab or an anti-M13-HRP Ab for NARA were used, and the absorbance was read at 450 nm. Shown are OD values from which absorbance of control wells (uncoated wells incubated with the corresponding anti-IL-2Ab plus anti-mouse IgG-HRP Ab) were subtracted.

FIG. 5 shows that the Ab with pro-Teff action, MAB605, binds to all the IL-2 forms; and the NARA one, which also has pro-Teff action also binds to IL-2V1 and IL-2V2 (in these preliminary experiments, the NARA Ab was only tested against IL-2V1 and IL-2V2). On the contrary, the Ab with pro-Treg action, 5344, shows reduced/no binding to the IL-2 variants. These results confirm that the designed IL-2Vs can be used as a powerful tool to screen for anti-IL-2 Abs with CD25 mimotope activity including Abs with pro-Teff activity as well as Abs with pro-Treg activity.

Example 4. In Vitro Evaluation of the Biological Activity of the IL-2 Variants It was evaluated whether the different IL-2 variants showed different affinities/selectivity for the T cell populations expressing either the IL-2R of intermediate affinity (present in CD4+ or CD8+ T-effector cell, or the IL-2R of high affinity (present in Treg cells).

Therefore, CD3 positive T cells were enriched from PBMCs from healthy donors according to manufacturer instructions (MILTENYI). CD3 enriched cells were cultured in 96-well plates in 75 uL/well in SVF-free RPMI medium (GIBCO, France) containing different concentrations of Proleukine (NOVARTIS) or IL-2V1, IL-2V2, IL-2V3, IL-2V4, IL-2V5 and IL-2V6 (from 0,0001 nM to 1000 nM). Phosphorylation of STAT5 (STAT5-P) in human Treg cells (IL-2Rαβγ), CD4+ Teff cells (IL-2Rβγ) and CD8+ T cells (IL-2Rβγ) was measured by flow cytometry, as follows. After 15 min of stimulation, cultures were fixed with 200 uL/well of PBS/2% paraformaldehyde for 10 min at room temperature. After washing with PBS/0.2% BSA, cells were permeabilized with 100 uL/well of ice-cold methanol for 10 min on ice. Cells were then washed with PBS/0.2% BSA and stained with anti-CD3 PE-Cy7 (clone UCHT1; 1:200; BD BIOSCIENCES), anti-CD4 PE-CF594 (clone RPA-T4 1:100; OZYME), anti-CD25 PE (clone M-A251; 1:5; BD Biosciences), anti-Foxp3 Alexa488 (clone 236A/E7; 1:20; EBIOSCIENCES) and anti-pSTAT5 Alexa647 (clone 47/Stat5 (pY694); 1:20; BD BIOSCIENCES) for 45 min at 4° C. Cells were acquired on a LSRII flow cytometer and analyzed with FlowJo software.

The results show that human IL-2V2 and IL-2V3 selectively induce STAT-5 phosphorylation in Tregs but not in T-effector cells in comparison with the commercial human IL-2 Proleukine. IL-2V1, IL-2V4, IL-2V5 and IL-2V6 do not stimulate Tregs or effector T cells at the evaluated doses (FIG. 6).

Example 5. In Vivo Evaluation of the Biological Activity of the IL-2 Variants To evaluate the in vivo effect of the IL-2Vs, a graft-versus-host disease (GVHD) model was used, in which human peripheral blood mononuclear cells are injected into an immunodeficient host mice. The human T cells, upon recognition of the mouse antigens, get activated and induce xeno-GVHD. Clinically, GVHD is evaluated by the loss of body weight of the mice. It has been previously shown that Treg cells can control GVHD (Gaidot A, Blood, 2011, 117, 2975-2983). Moreover, low-dose IL-2 administration has been reported to stimulate Tregs cells, and thus dampen inflammation and reduce disease symptoms (Shin et al., Blood, 2011, 118, 2342-2350). It was hypothesized that if IL-2Vs specifically stimulate Tregs in vivo, then, Treg cells should preferentially expand over CD4 and CD8+ T cells and reduce disease symptoms.

To induce acute GVHD, NSG-SGM3 female mice received PBMCs containing $6\times10^6$ human CD3− T cells, by the i.v. route. The same day mice were treated by i.p. injection of Proleukine (6 ug eq 100,000 IU), IL-2V1 (6 ug), or IL-2V2 (6 ug). A group of mice was left untreated. Blood samples were taken at day 5, 10 and 21 after treatment for immunomonitoring, and body weight was monitored along the experiment to detect the progress of GVHD.

Untreated mice, similar to Proleukin treated mice started to lose weight by day 20 after PBMC injection. IL-2V2 slightly delayed, and IL-2V1 stopped body weight loss at the used doses, being IL-2V1 clinical effect associated with a slightly prolonged increase in mice survival (FIG. 7). Moreover, IL-2V1 induced a sustained increase in the frequency of circulating human Treg, and also of CD4+ CD25+ Tregs, which has been described as Tregs with increased suppressive function (FIG. 8). These results show that the IL-2Vs can control GVHD; and that IL-2V1 is more effective in stopping weight loss and in increasing CD25+ Tregs in vivo.

To evaluate the in vivo effect of IL-2V2 and IL-2V3, C57BL/6 healthy mice were treated for four consecutive days by i.p. injection of Proleukine (4 µM), IL-2V2 (40 µM), or IL-2V3 (40 µM). A group of mice were left untreated. Blood samples were taken the day after the last dose of Proleukine or IL-2Vs for FACS analysis.

IL-2V2 and IL-2V3 treated mice showed an increase in frequency of circulating Tregs in comparison with untreated mice, although in a lesser extent than Proleukine-treated mice (FIG. 10). However, unlike Proleukine, IL-2V2 (40 µM) and IL-2V3 (both concentrations) did not increase the frequency of effector cells (CD8+ T cells and NK cells) neither induced the proliferation of those cells (measured by Ki67 expression). This is highlighted by the diminution of CD8 and NK cell to Treg ratio in mice treated with the IL-2-Vs compared to untreated and Proleukine treated mice. These data show that IL-2V2 and IL-2V3 also selectively stimulate Tregs in mice in vivo (conserved function across species). These data reinforce the potential of IL-2V2 and IL-2V3 as new drugs that selectively stimulate Treg cells, both, in vitro and in vivo through the selective induction of STAT-5-P on Treg cells in vitro, in comparison with Proleukine.

Example 6. IL-2V1, IL-2V4, IL-2V5 and IL-2V6 Act as IL-2 Antagonists

In view of the results observed in the GVHD model, it was hypothesized that IL-2-V1 could be acting as an IL-2 antagonist. To further investigate this hypothesis, the capacity of IL-2V1 to compete with Proleukine for the induction of STAT5 phosphorylation in T cells expressing either the intermediate affinity IL-2R (CD4+ effector cells and CD8+ T effector cells), or the high affinity IL-2R (Treg cells) was evaluated in vitro. With this aim, cells were stimulated with different concentrations of Proleukine and with a constant high concentration of IL-2V1 (1000 nM) using the above described in vitro biological assay. It can be observed in FIG. 9 that IL-2-V1 competes with WT IL-2 binding to the IL-2Rαβγ and IL-2Rβγ; underlying IL-2-V1 antagonistic function.

Binding of IL-2 variants to the IL-2Rαβγ was assayed in IL-2-dependent human cell line Kit225 cell line that constitutively expresses IL-2Rαβγ. For ease of detection, IL-2 variants were produced with a Streptavidin Tag that allows the detection of the molecules by FACS using an anti-Streptavidin-Tag antibody (a-Strep-Tag Ab). For the experiment, Kit225 cells were deprived of IL-2 for 2 days. After that, $0.2\times10^6$ cells were incubated on ice for 20 min alone or with 10 µM of IL-2 wt, IL-2V1, V2, V3, V4, V5 and V6. After wash with PBS/0.2% BSA buffer, cells were stained with an a-Strep-Tag Ab (Strep-Tactin-A488, Iba) for 20 min at 4° C. Cells were acquired on a LSRII flow cytometer and analyzed with FlowJo software. The data presented in FIG. 11 show that all the IL-2 variants bind to the IL-2Rαβγ to different degrees, and together with those shown in FIGS. 6 and 9, support the hypothesis of IL-2V1 and IL-2V4-6 are acting as IL-2 antagonist.

This hypothesis was confirmed by in vitro data showing that IL-2V antagonists compete with IL-2 for CD4+ T cells activation (Tconv and Treg cells) and inhibit Treg division in vitro by depriving them from wild-type IL-2 signaling (similar to a blocking anti-IL-2 antibody), leaving active IL-2 signaling in CD8+ T cells. Briefly, CellTrace Violet (CTV)-labelled human PBMCs and CD25+ T cells (mixed at 50:50 ratio) were incubated for 96 h with antiCD3/antiCD28 beads (1:5 bead:cell ratio)+IL-2V1, 4, 6, anti-hIL-2mAb (Mab602) or PBS (endogenous IL-2 control). CTV dilution (as a measure of T cell division) of CD4+ Tconvs, Tregs and CD8+ T cells was measured by flow cytometry. FIG. 12 shows the percentage (%) of $CTV^{Low}$ cells relative to PBS condition (max). The data show that IL-2 V1, V4 &V6 antagonize IL-2 signaling by competing with endogenous IL-2 on CD4+ T cells and inhibit Treg division in vitro by depriving them from wild-type IL-2 signaling (similar to a blocking anti-IL-2 antibody), leaving active IL-2 signaling in CD8+ T cells. These data together with those shown in FIGS. 6, 9 and 11 show that IL-2V1 and IL-2V4-6 act as IL-2 antagonists that can be used to disarm Tregs by depriving or starving Tregs from WT IL-2 signaling, and thereby inhibit Treg function, induce Treg loss of function or eliminate Tregs, while preserving effector CD8+ T cell function.

In vivo, it is expected that inhibition of Tregs with the IL-2 antagonist variants of the invention will reduce tumor growth as previously shown with other IL-2 antagonists (Carmenate et al., The Journal of Immunology, 2018, 200, 3475-3484). Therefore, it is expected that the IL-2Vs of the invention that are IL-2 antagonist will have an antitumor effect in vivo. Treg inhibition by the IL-2 antagonist variants according to the invention will consequently promote immune responses (lymphocytes (B, NK, CD4+ or CD8+ T cells); dentritic cells (DC); macrophages and others) by unleashing immune cells from Treg suppression. Furthermore, CD8+ T cell function is preserved or moderately impacted, depending on the used dose of IL-2Vs antagonist (FIG. 9; FIG. 12). Therefore, the IL-2 antagonist variants of the invention further allow the direct stimulation of a CD8+ T cell immune response, for example against a tumor, a pathogen or a vaccine. For all these reasons, better immune responses to cancer, infectious agents and vaccines are expected with the IL-2-antagonist variants of the invention.

Altogether the results presented in the application suggest that the effect of the IL-2 antagonist variant in vivo may vary depending on the immune context since it reduces immune activation (by neutralizing excess endogenous IL-2) when the immune system is overactive and produces excess IL-2 while it increases immune activation (by Treg inhibition and subsequent CD8+ T cell activation) in different immune contexts. For these reasons, the IL-2 antagonist variants are useful for treating diseases comprising overactivity of the immune system associated with overproduction of IL-2 such as chronic or acute inflammatory diseases, graft-versus-host disease (GVHD) and graft rejection, and also for treating cancer and infectious diseases and increasing immune responses to vaccines.

Example 7. Crystal Structure of the IL-2 Variants

Experimental Procedures

The IL-2 variants were cloned into a modified pMT/BiP plasmid (Invitrogen) and used to obtain stable transfectants of *Drosophila* S2 cells. The proteins were purified from the supernatant using affinity and size exclusion chromatography. Crystals of IL-2 V1 were obtained in 30% (w/v) PEG 8000, 0.1M Imidazole pH 8.0, 0.2M NaCl and those of IL-2 V4 in 15% (w/v) PEG 3350, 0.1M Hepes 7, 5 mM $NiCl_2$, and 10 mM $MgCl_2$ and flash-frozen in liquid nitrogen. The structures were solved by molecular replacement using the structure of the wild type IL-2 as a model.

Results

The inventors have also solved the crystal structure of some of the variants which gave some insight on their mechanism of action. The inventors have observed that the Y31P substitution (IL2-V4) stabilizes the IL-2 in a conformation similar to the one observed in the complex with IL2-R alpha subunit, hereafter the "alpha induced conformation". Indeed, there is some recent evidence from the murine IL-2 suggesting that conformational changes in the loop AB, where the Tyr31 is located, impact allosterically the interaction with the IL-2R beta and gamma subunits ((De Paula et al., P.N.A.S., doi/10.1073; Mar. 17, 2020 and Spangler et al., Immunity, 2015, 42, 815-825). Therefore, it is tempting to speculate that the molecular mechanism underlying the IL2-V4 activity takes advantage of this allosteric circuit. Indeed, the inventors have also obtained the structure of the IL2-V1, with the same activity of IL2-V4. In spite none of the mutations present in this variant are located in the AB loop, it also displays the same "alpha induced conformation".

Without being bound by theory, the inventors believe that the substitutions which have been introduced in the IL-2 antagonist variants of the invention stabilize the bound form and induce conformational changes which impact allosterically the interaction with the IL-2R beta and gamma subunits.

CONCLUSIONS

Overall, these results demonstrate that IL-2Vs are new drugs that selectively stimulate Treg cells or antagonize IL-2. Thus IL-2Vs could be used to expand Tregs ex vivo or in vivo or to block IL-2-mediated overactivation of the immune system and suppress harmful immune responses in vivo. In particular, IL-2Vs that selectively stimulate Treg cells in vivo are useful for treating diseases involving an immune dysfunction such as allergic diseases and autoimmune diseases and diseases associated with overactivity of the immune system such as chronic or acute inflammatory diseases, graft-versus-host disease (GVHD) and graft rejection. The IL-2-antagonist variants are useful for treating diseases associated with overactivity of the immune system including an overproduction of IL-2 like GVHD, graft rejection and chronic or acute inflammatory diseases.

IL-2Vs that are IL-2 antagonists are also useful for inhibiting Tregs and thus increase immune responses (B, NK, CD4+ or CD8+ T cells, DC, macrophages and others), in particular antitumor immune responses in cancer treatment and immune responses to vaccines or pathogens.

---

The invention claimed is:

1. A human interleukin-2 variant for the prevention or treatment of immune disorders, which is selected from the group consisting of:

a variant comprising the substitutions K9E, L12E, H16R, L19R, M23L, N26K, S87N, V91K, E95K, N119K, T123A, and S127K;

a variant comprising the substitutions K9E, L12E, H16R, L19R, M23L, N26K, S87N, V91K, E95K, Y31P, K49Q, E52S, R81E, D84N, N119K, T123A, T131R and L132S;

a variant comprising the substitution Y31P, wherein the variant does not comprise any substitution at positions 9, 12, 16, 19, 23, 26, 49, 52, 81, 84, 87, 91, 95, 119, 123, 127, 131 and 132;

a variant comprising the substitutions K9E, L12E, H16R, L19R, M23L, N26K, S87N, V91K, E95K, Y31P, K49Q, E52S, R81E, D84N, T131R and L132S;

a variant comprising the substitutions K9E, L12E, H16R, L19R, M23L, N26K, S87N, V91K, E95K, Y31P, N119K, T123A, and S127K; and a variant comprising the substitutions K9E, L12E, H16R, L19R, M23L, N26K, S87N, V91K, E95K, K49Q, E52S, R81E, D84N, N119K, T123A, T131R and L132S;

wherein the indicated positions are determined by alignment with SEQ ID NO: 1.

2. The variant according to claim 1, which has at least 70% amino acid identity with any one of SEQ ID NO: 1 and 3 to 8, and which does not comprise any substitution at positions: 11, 13, 15, 18, 20, 22, 29, 30, 35, 37, 48, 68, 69, 71, 74, 75, 76, 80, 85, 86, 88, 92, 110, 125, 126, 129, 130 and 133.

3. The variant according to claim 1, comprising the substitutions: K9E, L12E, H16R, L19R, M23L, N26K, S87N, V91K, E95K, Y31P, K49Q, E52S, R81E, D84N N119K, T123A, T131R and L132S; or K9E, L12E, H16R, L19R, M23L, N26K, S87N, V91K, E95K, Y31P, K49Q, E52S, R81E, D84N, T131R and L132S, said variant stimulating T regulatory cells.

4. The variant according to claim 1 comprising the substitutions:

K9E, L12E, H16R, L19R, M23L, N26K, S87N, V91K, E95K, N119K, T123A, and S127K;

K9E, L12E, H16R, L19R, M23L, N26K, S87N, V91K, E95K, Y31P, N119K, T123A, and S127K;

K9E, L12E, H16R, L19R, M23L, N26K, S87N, V91K, E95K, K49Q, E52S, R81E, D84N, N119K, T123A, T131R and L132S; or Y31P, wherein the variant does not comprise any substitution at positions 9, 12, 16, 19, 23, 26, 49, 52, 81, 84, 87, 91, 95, 119, 123, 127, 131 and 132, said variant being an IL-2 antagonist.

5. The variant according to claim 1, which is associated with an agent of interest, in the form of a molecular complex, a particle, a conjugate or a fusion protein.

6. The variant according to claim 5, which is complexed with an anti-IL-2 antibody with Pro-T-regulatory cell or Pro-T-effector cell activity.

7. The variant according to claim 5, which is fused to an antibody against a surface molecule specific for Tregs or a functional fragment thereof comprising at least the antigen binding site, wherein the antibody is selected from the group consisting of anti-CTLA-4, anti-CD25, anti-CCR8, anti-ICOS, anti-IKZF2, anti-CD70, anti-GARP, anti-IL1R1, anti-CD39, anti-CCR4 and anti-CD177 antibody.

8. An isolated polynucleotide encoding the variant according to claim 1 in expressible form.

9. A pharmaceutical composition comprising, as active substance, an IL-2 variant according to claim 3 which stimulates T regulatory cells, a polynucleotide encoding said variant or a cell modified with said polynucleotide, and at least one pharmaceutically acceptable vehicle and/or carrier.

10. A method of treating a disease selected from the group consisting of acute or chronic inflammatory diseases, allergic diseases, autoimmune diseases, graft-versus-host disease and graft rejection, comprising administering to a subject in need thereof a therapeutically effective amount of the pharmaceutical composition according to claim 9.

11. A pharmaceutical composition comprising, as active substance, an IL-2 variant according to claim 4 which is an IL-2 antagonist, a polynucleotide encoding said variant or a cell modified with said polynucleotide, and at least one pharmaceutically acceptable vehicle and/or carrier.

12. A method of therapeutically treating an established cancer, comprising administering to a subject in need thereof a therapeutically effective amount of the pharmaceutical composition according to claim 11.

13. A method of treating a disease comprising overactivity of the immune system associated with overproduction of IL-2 selected from the group consisting of acute or chronic inflammatory diseases, graft-versus-host disease and graft rejection, comprising administering to a subject in need thereof a therapeutically effective amount of the pharmaceutical composition according to claim 11.

14. A method for screening anti-IL-2 antibodies with pro-T-regulatory cell or pro-T-effector cell activity, comprising contacting the variant according to claim 1 with a sample and detecting binding of the variant to anti-IL-2 antibodies wherein binding indicates an anti-IL-2 antibody with pro-T-effector cell activity and lack of binding indicates an anti-IL-2 antibody with pro-T-regulatory cell activity.

\* \* \* \* \*